(12) United States Patent
Beeler et al.

(10) Patent No.: US 12,181,479 B2
(45) Date of Patent: Dec. 31, 2024

(54) BODIPY-BASED DYES FOR DIGITAL SPATIAL PROTEOMICS

(71) Applicant: TRUSTEES OF BOSTON UNIVERSITY, Boston, MA (US)

(72) Inventors: Aaron Beaty Beeler, Boston, MA (US); Andrew Emili, Needham, MA (US); Jason Michael Lenihan, Brighton, MA (US); Nathaniel Ryan Hendrick, Boston, MA (US); Ichun Anderson Chen, Framingham, MA (US)

(73) Assignee: TRUSTEES OF BOSTON UNIVERSITY, Boston, MA (US)

(*) Notice: Subject to any disclaimer, the term of this patent is extended or adjusted under 35 U.S.C. 154(b) by 0 days.

(21) Appl. No.: 18/086,923

(22) Filed: Dec. 22, 2022

(65) Prior Publication Data
US 2023/0194539 A1 Jun. 22, 2023

Related U.S. Application Data

(60) Provisional application No. 63/339,137, filed on May 6, 2022, provisional application No. 63/292,683, filed on Dec. 22, 2021.

(51) Int. Cl.
G01N 33/00 (2006.01)
C07F 5/02 (2006.01)
G01N 33/68 (2006.01)

(52) U.S. Cl.
CPC ......... G01N 33/6818 (2013.01); C07F 5/022 (2013.01)

(58) Field of Classification Search
CPC .................................................. G01N 33/6818
USPC ............................................................ 436/89
See application file for complete search history.

(56) References Cited

U.S. PATENT DOCUMENTS

| | | | |
|---|---|---|---|
| 9,566,335 B1* | 2/2017 | Emili .................... | C07K 14/245 |
| 2002/0132254 A1* | 9/2002 | Twu ...................... | C07H 21/04 |
| | | | 435/7.1 |
| 2018/0372752 A1 | 12/2018 | Emili et al. | |
| 2020/0018768 A1 | 1/2020 | Marcotte et al. | |
| 2021/0148922 A1 | 5/2021 | Dyer et al. | |

OTHER PUBLICATIONS

Ma et al. "Ratiometric fluorescence detection of cysteine and homocysteine with a BODIPY dye by mimicking the native chemical ligation" Analyst, 2015, 140, 422 (Year: 2015).*

(Continued)

*Primary Examiner* — Christine T Mui
*Assistant Examiner* — Emily R. Berkeley
(74) *Attorney, Agent, or Firm* — Nixon Peabody LLP; Ronald I. Eisenstein; Ravinderjit S. Braich

(57) ABSTRACT

The disclosure provides probes comprising dipyrromethane-BF$_2$ derivatives which exhibits different fluorescent spectral properties when conjugated to the amino acids, compositions and kits comprising same. The disclosure also provides methods for detecting/identifying amino acids and sequencing polypeptide molecules by conjugating a dipyrromethane-BF2 derivative which exhibits different fluorescent spectral properties when conjugated to the amino acids.

28 Claims, 22 Drawing Sheets

(56) References Cited

OTHER PUBLICATIONS

Belmonte-Vazquez et al. "A versatile synthetic approach to design tailor-made push-pull chromophores with intriguing and tunable photophysical signatures" Dyes and Pigments 147 (2017) 246-259 (Year: 2017).*

Bachman. "Design and synthesis of fluorophores for peptide fluorosequencing". Diss. 2019.

Belmonte-Vazquez et al. "A versatile synthetic approach to design tailor-made push-pull chromophores with intriguing and tunable photophysical signatures." Dyes and Pigments 147 (2017): 246-259.

Belmonte-Vazquez et al. "Synthetic approach to readily accessible benzofuran-fused borondipyrromethenes as red-emitting laser dyes." The Journal of Organic Chemistry 84.5 (2019): 2523-2541.

Jethava et al. "One Scaffold-Different Organelles Sensors: pH-Activable Fluorescent Probes for Targeting Live Primary Microglial Cell Organelles." bioRxiv (2021): 2021-05.

Kim et al. "Fluorescent labeling of protein using blue-emitting 8-amino-BODIPY derivatives." Journal of Fluorescence 27 (2017): 2231-2238.

Liao et al. "Synthesis, optical and electrochemical properties of novel meso-triphenylamine-BODIPY dyes with aromatic moieties at 3, 5-positions." Tetrahedron 71.31 (2015): 5078-5084.

Prusty et al. "A fluorogenic reaction based on heavy-atom removal for ultrasensitive DNA detection." Journal of the American Chemical Society 132.35 (2010): 12197-12199.

Roacho et al. "Formation of 8-RS-BODIPYs via direct substitution of 8-MeS-BODIPY by RSH (R= Et, Pr, Bu, tBu, n-C12H25, C6H5, p-MeC6H4, p-MeOC6H4, and 2, 6-Me2C6H3)." Canadian Journal of Chemistry 94.3 (2016): 234-239.

Wang et al. "meso-Alkoxy BODIPYs with a good balance between larger Stokes shifts and higher fluorescence quantum yields." RSC advances 3.7 (2013): 2203-2206.

Farinone et al. "BODIPY-amino acid conjugates-tuning the optical response with a meso-heteroatom." Organic Chemistry Frontiers 7.17: 2391-2398 (2020).

Ksenofontova et al. "Novel BODIPY-conjugated amino acids: Synthesis and spectral properties." Journal of Molecular Liquids 283: 695-703 (2019).

* cited by examiner

BODIPY-BASED DYES FOR DIGITAL SPATIAL PROTEOMICS

CROSS REFERENCE TO RELATED APPLICATIONS

This application claims benefit under 35 U.S.C. § 119(e) of U.S. Provisional Application No. 63/292,683, filed Dec. 22, 2021, and U.S. Provisional Application No. 63/339,137, filed May 6, 2022, the contents of both of which are incorporated herein by reference in their entireties.

TECHNICAL FIELD

The field of invention relates to compositions, kits and methods for detecting/identifying amino acids and sequencing polypeptide molecules.

BACKGROUND

Proteins are fundamental to cellular function, and their expression, location, and abundance are key to identification between a healthy and diseased cell. Rapid intracellular protein identification would enable a new paradigm in biomedical research, allowing scientists to determine how disease and aging affect protein networks in cells.

The invention described herein comprises novel dyes and methods of detecting and determining the concentration of proteins and amino acids in solution and in biological milieu (e.g. blood, plasma, serum, cells, tissue, etc.).

There remains a need for reagents, methods and assays for detecting/identifying amino acids and sequencing polypeptide molecules and for identification, quantification and imaging of many different proteins simultaneously in complex biological samples.

SUMMARY

In one aspect, provided herein is a method of identifying an amino acid. Generally, the method comprises conjugating a probe that exhibits different spectral properties, e.g., different fluorescent spectral properties when conjugated to different amino acids. Once the probe is conjugated to the amino acid, one or more spectral properties, e.g., fluorescent spectral properties of the probe conjugated to the amino acid are measured or detected. The amino acid is identified by comparing the fluorescent spectral properties, e.g., fluorescent spectral properties of the probe to a plurality of reference spectral properties, e.g., fluorescent spectral properties wherein each reference spectral property, e.g., fluorescent spectral properties is representative of the probe conjugated to a different amino acid.

The probe can be conjugated at any available position of the amino acid. For example, the probe can be conjugated, e.g., covalently linked to an amino, a carboxylic, a hydroxyl, or a thiol group of the amino acid. In some embodiments of any one of the aspects described herein, the probe is conjugated, e.g., covalently linked to an amino group of the amino acid. In some other embodiments of any one of the aspects described herein, the probe is conjugated, e.g., covalently linked to a carboxylic group of the amino acid.

As the probes utilized in the method for identifying or detecting the exhibit different spectral properties, e.g., different fluorescent spectral properties when conjugated to the amino acid, the method described herein can be used to detect/identify more than one amino acid simultaneously, e.g., in a multiplex format. Accordingly, in another aspect provided herein is a multiplex method for detecting or identifying a plurality of amino acids. Generally, the method comprises conjugating a plurality of probes to a plurality of amino acids, wherein the probes exhibits different spectral properties, e.g., different fluorescent spectral properties when conjugated to different amino acids. Once the probes are conjugated to the amino acids, one or more spectral properties, e.g., fluorescent spectral properties of the probes conjugated to the amino acids are detected or measured. The amino acids are identified or detected by comparing the plurality of the fluorescent spectral properties of the probes to a plurality of reference fluorescent spectral properties, wherein each reference fluorescent spectral property is representative of the probe conjugated to a different amino acid. In some embodiments, the probes in the plurality are the same.

The amino acid to be identified/detected can be part of a polypeptide. When the amino acid is part of a polypeptide, the amino acid can be present anywhere in the polypeptide. For example, the amino acid can be at the N-terminus of the polypeptide. In some other non-limiting example, the amino acid can be at the C-terminus of the polypeptide. In yet some other non-limiting example, the amino acid can be at an internal, i.e., a non-terminal positon of the polypeptide.

When the amino acid to be identified/detected is at a terminal position of polypeptide, the methods described herein can be used for identifying/detecting a terminal amino acid of polypeptide. Accordingly, in another aspect, provided herein is a method for identifying/detecting a terminal amino acid of polypeptide. Generally, the method comprises conjugating a probe to a terminal amino acid of the polypeptide, wherein the probe exhibits different spectral properties, e.g., different fluorescent spectral properties when conjugated to different amino acids. Once the probe is conjugated with terminal amino acid, one or more spectral properties, e.g., fluorescent spectral properties of the probe conjugated to the amino acid are measured or detected. The amino acid is identified by comparing the fluorescent spectral properties, e.g., fluorescent spectral properties of the probe to a plurality of reference spectral properties, e.g., fluorescent spectral properties wherein each reference spectral property, e.g., fluorescent spectral properties is representative of the probe conjugated to a different amino acid.

In some embodiments of any one of the aspects described herein, the polypeptide is immobilized on a substrate prior to conjugating the probe to an amino acid in the polypeptide.

It is noted that the terminal amino acid to be detected/identified can be at either end of the polypeptide. Accordingly, in some embodiments of any one of the aspects described herein, the terminal amino acid is at an N-terminal of polypeptide. In some embodiments of any one of the aspects described herein, the terminal amino acid is at a C-terminal of polypeptide.

The method described herein for detecting/identifying a terminal amino acid can be used to detect/identify terminal amino acid of more than one polypeptide simultaneously, e.g., in a multiplex format. Accordingly, in another aspect provided herein is a multiplex method for detecting/identifying terminal amino acids of a plurality of polypeptides. Generally, the method comprises conjugating a plurality of probes to a terminal amino acid of each of the plurality of polypeptides, where each probe in the plurality of the probes exhibits different spectral properties, e.g., different fluorescent spectral properties when conjugated to different amino acids. Once the probes are conjugated with terminal amino acids, one or more spectral properties, e.g., fluorescent spectral properties of each probe conjugated to the amino acid are measured or detected. The terminal amino acids are identified by comparing the fluorescent spectral properties, e.g., fluorescent spectral properties of the probes to a plurality of reference spectral properties, e.g., fluorescent spectral properties wherein each reference spectral property, e.g., fluorescent spectral properties, is representative of the probe conjugated to a different amino acid.

The methods described herein, the probes in the plurality of the probes can be same or different. Thus, in some embodiments of the any one of the multiplex methods described herein, the probes in the plurality of the probes are the same. In some other embodiments of the any one of the multiplex methods described herein, at least two probes in the plurality of the probes are different.

The method of identifying/detecting a terminal amino acid of polypeptide can be used for sequencing polypeptide. For example, after the terminal amino acid has been detected/identified, the terminal amino acid can be cleaved from polypeptide and new terminal amino acid can be detected. This step of cleaving the terminal amino acid after detecting/identifying and detecting/identifying the next terminal amino acid can be repeated one or more times, e.g., to determine the sequence of at least a portion of the polypeptide. This can be carried out in a multiplex form to determine the sequence of at least a portion of a plurality of polypeptides simultaneously.

Methods of cleaving a terminal amino acid of a polypeptide are well known in the art and available to one of skill in the art. Such method can include enzymatic cleavage or chemical cleavage. Accordingly, in some embodiments of any one of the aspects described herein, the step of cleaving the terminal amino acid comprises enzymatic cleavage. In some other embodiments of any one of the aspects described herein, the step of cleaving the terminal amino acid comprises chemical cleavage.

The amino acid or the polypeptide can be present in a sample. The sample can be a biological sample. For example, the sample can be a biological fluid, a tissue, an organ, and/or a cell.

It is noted that any probe capable of exhibiting different spectral properties, e.g., fluorescent spectral properties can be utilized. In some embodiments of any one of the aspects described herein, the probe is a dipyrromethane-BF2 derivative. For example, the probe is a dipyrromethane-BF2 derivative comprising a labile or reactive group. In some embodiments of any one of the aspects described herein, the probe is a dipyrromethane-BF2 derivative comprising a 4,4-difluoro-4-bora-3a,4a-diaza-s-indacene derivative. Any position of the dipyrromethane-BF2 derivative can be used for conjugation with the amino acid. For example, the probe can be conjugated via position 8 (meso position) of the 4,4-difluoro-4-bora-3a,4a-diaza-s-indacene derivative. Accordingly, in some embodiments of any one of the aspects described herein, the 4,4-difluoro-4-bora-3a,4a-diaza-s-indacene derivative comprises a labile or reactive group at position 8 (meso position).

In some embodiments of any one of the aspects described herein, the probe is a compound of Formula (I):

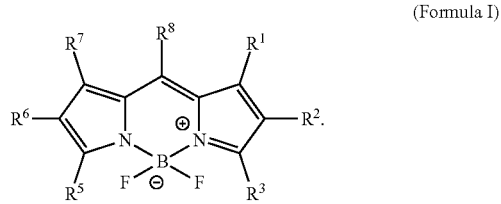

(Formula I)

In compounds of Formula (I), $R^1$, $R^2$, $R^3$, $R^4$, $R^5$, $R^6$, $R^7$ and $R^8$ are each independently selected from the group consisting of hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfonate, sulfinyl, sulfonyl, carbamoyl, isocyanato, thiocyanato, isothiocyanato, ureido, and a labile or leaving group, optionally at least one of $R^1$, $R^2$, $R^3$, $R^4$, $R^5$, $R^6$, $R^7$ and $R^8$, is a labile or leaving group. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, $R^8$ is a labile or leaving group.

A probe conjugated with an amino acid is also disclosed herein. Accordingly, in another aspect, provided herein is a compound of Formula (II):

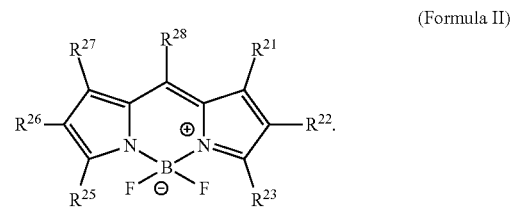

(Formula II)

In compounds of Formula (II), $R^{21}$, $R^{22}$, $R^{23}$, $R^{24}$, $R^{25}$, $R^{26}$, $R^{27}$ and $R^{28}$ are each independently selected from the group consisting of hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfonate, sulfinyl, sulfonyl, carbamoyl, isocyanato, thiocyanato, isothiocyanato, ureido, and an amino acid, optionally at least one of $R^{21}$, $R^{12}$, $R^{23}$, $R^{24}$, $R^{25}$, $R^{26}$, $R^{27}$ and $R^{28}$, is an amino acid. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, $R^{28}$ is an amino acid.

It is noted that the amino acid can be linked to rest of Formula (II) by its a amino group, the carboxyl group or a functional group in the side chain. In some preferred embodiments, the amino acid is linked to rest of Formula (II) by its a amino group.

In yet another aspect, provided herein is a kit comprising one or more compounds described herein.

DETAILED DESCRIPTION

Figure 1:
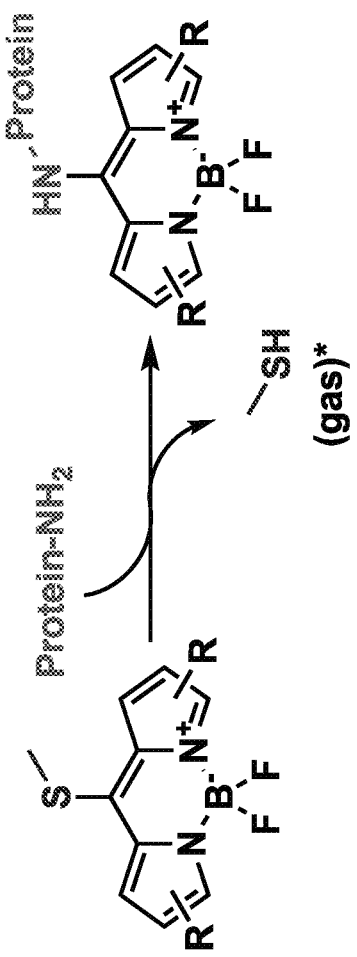
FIG. 1 is a schematic representation showing the reactivity of an exemplary 8-thioether BODIPY with the N-terminus of a protein through a SNAr reaction.

It is to be understood that both the foregoing general description and the following detailed description are exemplary and explanatory only and are not restrictive of the invention, as claimed. Further, the section headings used herein are for organizational purposes only and are not to be construed as limiting the subject matter described.

The present disclosure provides reagents, kits and methods for detecting/identifying amino acids and polypeptides. The reagents, kits and methods described herein are useful for detecting/identifying amino acids. The amino acids can be part of a polypeptide. Thus, the reagents, kits and methods described herein also are useful for sequencing single polypeptide molecules, multiple molecules of a single polypeptide, or multiple different single polypeptide molecule.

Accordingly, in one aspect provided herein is a method for detecting or identifying an amino acid. The method comprising: (a) conjugating a probe to an amino acid, wherein the probe comprises a dipyrromethane-BF2 derivative that exhibits different fluorescent spectral properties when conjugated to the amino acid; (b) detecting one or more fluorescent spectral properties of the probe conjugated to the amino acid; and (c) identifying the amino acid by comparing the fluorescent spectral properties of the probe to a plurality of reference fluorescent spectral properties, wherein each reference fluorescent spectral property is representative of the probe conjugated to a different amino acid.

The method described herein for detecting/identifying an amino acid can be used to detect/identify more than one amino acid simultaneously, e.g., in a multiplex format. Accordingly, in another aspect provided herein is a multiplex method for detecting or identifying a plurality of amino acids. The method comprises: (a) conjugating a plurality of probes to an amino, a carboxylic, a hydroxyl or a thiol group of a plurality of amino acids, wherein each probe in the plurality of the probes comprises a dipyrromethane-BF2 derivative that exhibits different fluorescent spectral properties when conjugated to different amino acids; (b) detecting one or more fluorescent spectral properties for each probe conjugated to the plurality of the amino acids; and (c) identifying the amino acid by comparing the plurality of the fluorescent spectral properties of the probes to a plurality of reference fluorescent spectral properties, wherein each reference fluorescent spectral property is representative of the probe conjugated to a different amino acid.

Probes

Embodiments of the various aspect described herein include a probe. In some embodiments of the various aspects described herein, the probe is a compound of Formula (I):

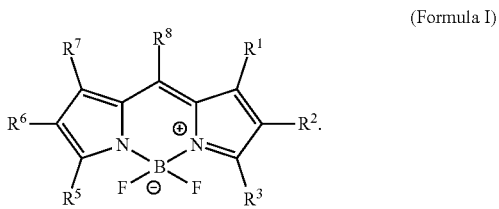

(Formula I)

In compounds of Formula (I), $R^1$, $R^2$, $R^3$, $R^4$, $R^5$, $R^6$, $R^7$ and $R^8$ are each independently selected from the group consisting of hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfonate, sulfinyl, sulfonyl, carbamoyl, isocyanato, thiocyanato, isothiocyanato, ureido, and a labile or leaving group, optionally at least one of $R^1$, $R^2$, $R^3$, $R^4$, $R^5$, $R^6$, $R^7$ and $R^8$, is a labile or leaving group. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, only one of $R^1$, $R^2$, $R^3$, $R^4$, $R^5$, $R^6$, $R^7$ and $R^8$ is a labile or leaving group.

As used herein, a "labile group" or a "leaving group" refers to a group that can be substituted by another group in a reaction, e.g., a substitution reaction such as a nucleophilic substitution reaction. Exemplary labile or leaving groups include, but are not limited to, a halide (fluoride, chloride, bromide, and iodide), azide, a sulfonate (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), succinimide-N-oxide, p-nitrophenoxide, pentafluorophenoxide, tetrafluorophenoxide, a carboxylate, an aminocarboxylate (carbamate) and an alkoxycarboxylate (carbonate). For substitutions at saturated carbon, halides and sulfonates are preferred leaving groups. For substitutions at a carbonyl carbon a halide, succinimide-N-oxide, p-nitrophenoxide, pentafluorophenoxide, tetrafluorophenoxide, a carboxylate, or an alkoxycarboxylate (carbonate) may for example be used as a leaving group.

In some embodiments of any one of the aspects described herein, the labile or leaving group is optionally substituted alkylthio, halogen, optionally substituted alkoxyl, hydxoryl, optionally substituted acyloxy, tosylate, triflate, mesylate, nitrile, azide, carbamate, disulfide, thioester, or diazonium. For example, the labile or leaving group is halogen or an alkylthio.

In some embodiments of any one of the aspects described herein, the labile or leaving group is —SR$^L$, wherein R$^L$ is optionally substituted alkyl, perhaloalkyl, optionally substituted alkenyl, optionally cycloalkyl, optionally substituted heterocyclyl, optionally substituted aryl or optionally substituted heteroaryl. For example, R$^L$ is substituted C1-C6alkyl, C1-C6perhaloalkyl optionally substituted C$_2$-C$_6$alkenyl, optionally substituted aryl or optionally substituted heteroaryl. In some embodiments of any one of the aspects described herein, R$^L$ is methyl, allyl, phenyl, 4-methoxyphenyl, 4-nitrophenyl, benzyl, or 4-methoxybenzyl. In some preferred embodiments, R$^L$ is methyl, i.e., the labile or leaving groups is —SMe.

In some embodiments of any one of the aspects described herein, R$^1$, R$^2$, R$^3$, R$^4$, R$^5$, R$^6$ and R$^7$ are each independently selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, and ureido; and R$^8$ is a labile or leaving group.

In some embodiments of any one of the aspects described herein, a compound of Formula (I) is of Formula (I-A):

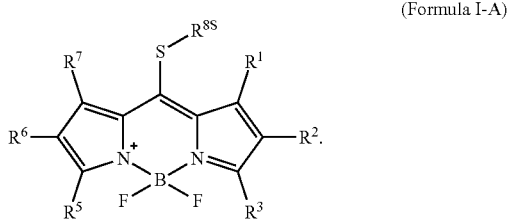

(Formula I-A)

In compounds of Formula (I-A), each of R$^1$, R$^2$, R$^3$, R$^4$, R$^5$, R$^6$, and R$^7$ can be independently selected from the group consisting of hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido; and R$^{8S}$ is optionally substituted alkyl, optionally substituted alkenyl, optionally cycloalkyl, optionally substituted heterocyclyl, optionally substituted aryl or optionally substituted heteroaryl. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, R$^{8S}$ is an optionally substituted aryl. For example, is R$^{8S}$ an optionally substituted phenyl. Accordingly, in some embodiments of any one of the aspects described herein, a compound of Formula (I), e.g., of Formula (I-A) is of Formula (I-B):

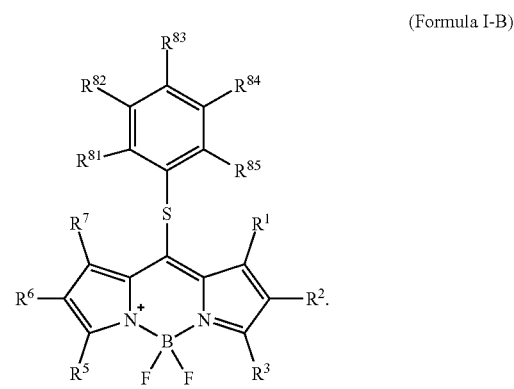

(Formula I-B)

In compounds of Formula (I-B), each of R$^1$, R$^2$, R$^3$, R$^4$, R$^5$, R$^6$, and R$^7$ can be independently selected from the group consisting of hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido; and each of R$^{81}$, R$^{82}$, R$^{83}$, R$^{84}$ and R$^{85}$ is independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, a compound of Formula (I) is of Formula (I-C) or Formula (I-D):

(Formula I-C)

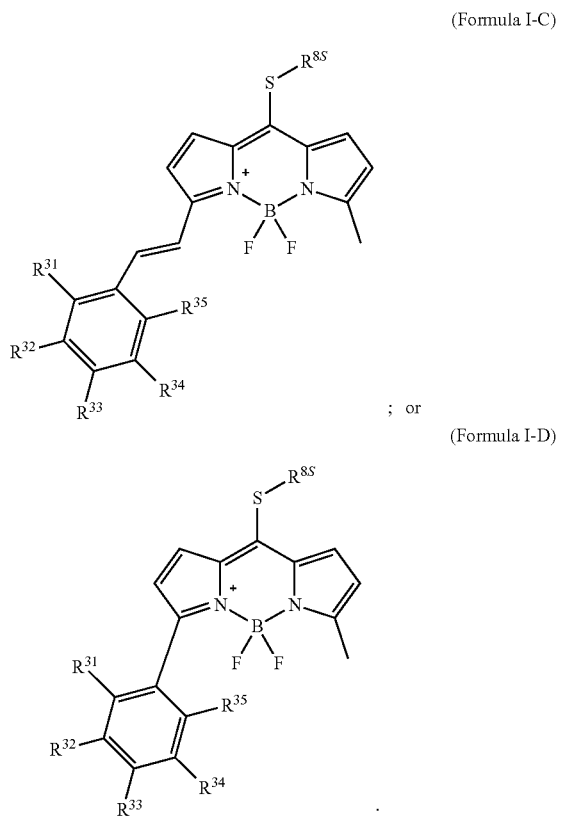

; or (Formula I-D)

(Formula I-E)

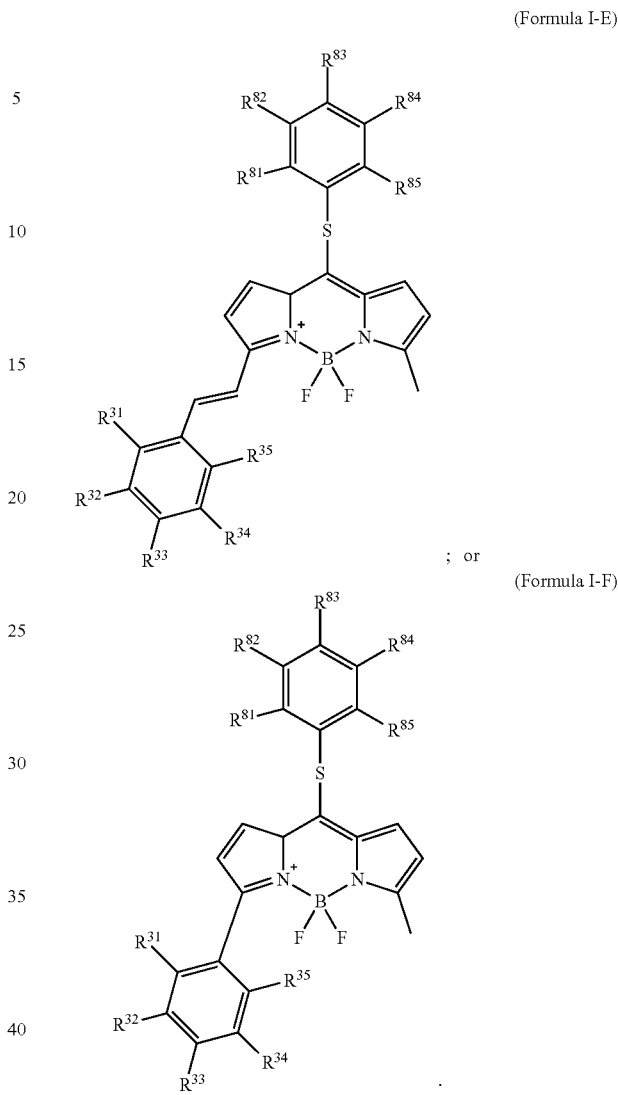

; or (Formula I-F)

In compounds of Formula (I-C) and (I-D), each of $R^{31}$, $R^{32}$, $R^{33}$, $R^{34}$ and $R^{35}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{31}$, $R^{32}$, $R^{33}$, $R^{34}$ and $R^{35}$, together with the carbon atoms they are attached to form an optionally substituted aryl; and $R^{8S}$ is optionally substituted alkyl, optionally substituted alkenyl, optionally cycloalkyl, optionally substituted heterocyclyl, optionally substituted aryl or optionally substituted heteroaryl. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, a compound of Formula (I) is of Formula (I-E) or Formula (I-F):

In compounds of Formula (I-E) and (I-F), each of $R^{31}$, $R^{32}$, $R^{33}$, $R^{34}$ and $R^{35}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{31}$, $R^{32}$, $R^{33}$, $R^{34}$ and $R^{35}$, together with the carbon atoms they are attached to form an optionally substituted aryl; and; and each of $R^{81}$, $R^{82}$, $R^{83}$, $R^{84}$ and $R^{85}$ is independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6)

independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, a compound of Formula (I) is of Formula (I-G) or Formula (I-H):

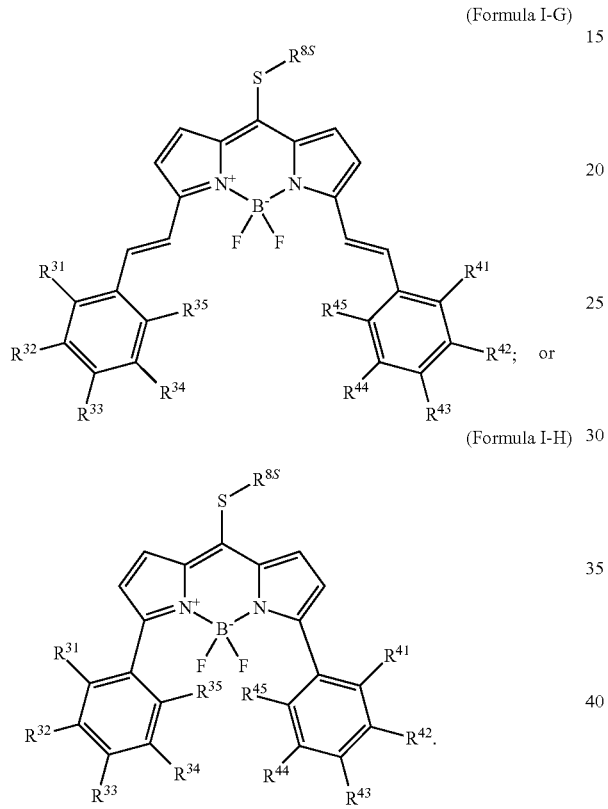

In compounds of Formula (I-G) and (I-H), each of $R^{31}$, $R^{32}$, $R^{33}$, $R^{34}$ and $R^{35}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{31}$, $R^{32}$, $R^{33}$, $R^{34}$ and $R^{35}$, together with the carbon atoms they are attached to form an optionally substituted aryl; each of $R^{41}$, $R^{42}$, $R^{34}$, $R^{44}$ and $R^{45}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{41}$, $R^{42}$, $R^{34}$, $R^{44}$ and $R^{45}$, together with the carbon atoms they are attached to form an optionally substituted aryl; and $R^{8S}$ is optionally substituted alkyl, optionally substituted alkenyl, optionally cycloalkyl, optionally substituted heterocyclyl, optionally substituted aryl or optionally substituted heteroaryl. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, a compound of Formula (I) is of Formula (I-I) or Formula (I-J):

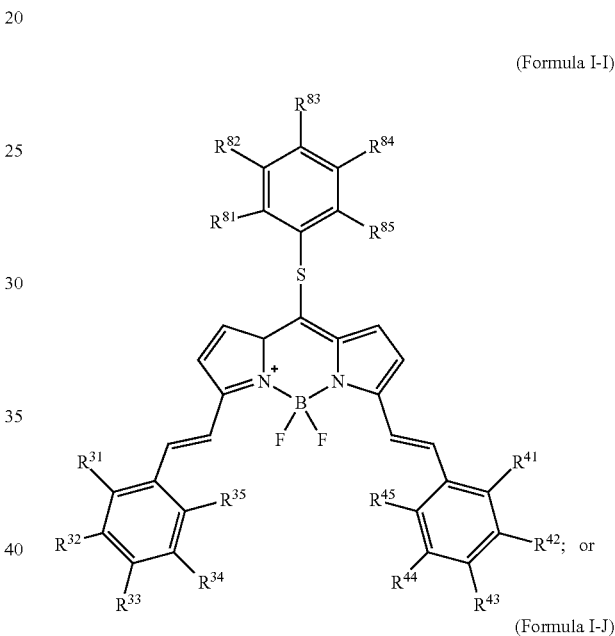

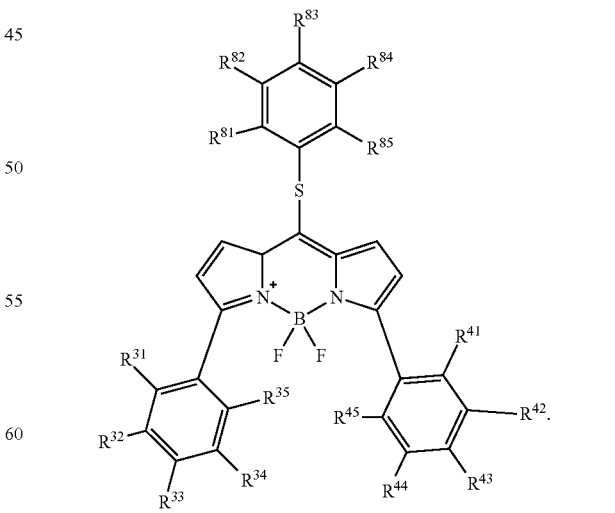

In compounds of Formula (I-I) and (I-J), each of $R^{31}$, $R^{32}$, $R^{33}$, $R^{34}$ and $R^{35}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{31}$, $R^{32}$, $R^{33}$, $R^{34}$ and $R^{35}$, together with the carbon atoms they are attached to form an optionally substituted aryl; each of $R^{41}$, $R^{42}$, $R^{34}$, $R^{44}$ and $R^{45}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{41}$, $R^{42}$, $R^{34}$, $R^{44}$ and $R^{45}$, together with the carbon atoms they are attached to form an optionally substituted aryl; and each of $R^{81}$, $R^{82}$, $R^{83}$, $R^{84}$ and $R^{85}$ is independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

$R^8$

In some embodiments of any one of the aspects described herein, $R^8$ is a labile or leaving group. For example, $R^8$ is optionally substituted alkylthio, halogen, optionally substituted alkoxyl, hydxoryl, optionally substituted acyloxy, tosylate, triflate, mesylate, nitrile, azide, carbamate, disulfide, thioester, or diazonium. In some embodiments of any one of the aspects described herein, $R^8$ is alkylthio or halogen.

In some embodiments of any one of the aspects described herein, $R^8$ is —$SR^{8S}$, wherein $R^{8S}$ is optionally substituted alkyl, perhaloalkyl, optionally substituted alkenyl, optionally cycloalkyl, optionally substituted heterocyclyl, optionally substituted aryl or optionally substituted heteroaryl. For example, $R^{8S}$ is optionally substituted C1-C6alkyl, C1-C6perhaloalkyl optionally substituted $C_2$-$C_6$alkenyl, optionally substituted aryl or optionally substituted heteroaryl.

In some embodiments of any one of the aspects described herein, $R^{8S}$ is methyl, allyl, phenyl, 4-methoxyphenyl, 4-nitrophenyl, benzyl, or 4-methoxybenzyl.

In some embodiments of any one of the aspects described herein, $R^{8S}$ is methyl. For example, $R^8$ is —SMe.

In some embodiments of any one of the aspects described herein, $R^8$ halogen. For example, $R^8$ is Cl, Br, I or F.

$R^1$

In compounds of Formula (I), $R^1$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or a labile or leaving group. For example, $R^1$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^1$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, carboxyl, hydroxyl, isocyanato, thiocyanato, isothiocyanato, sulfonate, and sulfonyl. For example, $R^1$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^1$ is H, halogen, or optionally substituted optionally substituted alkyl. For example, $R^1$ is H. In some other non-limiting examples, $R^1$ is an optionally substituted $C_1$-$C_6$alkyl. Exemplary alkyls for $R^1$ include, but are not limited to methyl, ethyl, propyl, i-propyl, n-butyl, t-butyl, n-pentyl and hexyl.

In some embodiments of any one of the aspects described herein, $R^1$ is H or methyl.

In some embodiments of any one of the aspects described herein, $R^1$ is a labile or leaving group.

$R^2$

In compounds of Formula (I), $R^2$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or a labile or leaving group. For example, $R^2$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^2$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, optionally substituted acyl, carboxyl, hydroxyl, isocyanato, thiocyanato, isothiocyanato, sulfonate, and sulfonyl. For example, $R^2$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^2$ is H, halogen, optionally substituted alkyl, perhaloalkyl, carbonyl, carboxyl, optionally substituted acyl, or sulfonyl. For example, $R^2$ can be H, halogen, optionally substituted $C_1$-$C_6$alkyl, —C(O)H, or —SO$_3$H.

In some embodiments, of any one of the aspects described herein, $R^2$ is H, Br, Cl, —C(O)H, or —SO$_3$H.

In some embodiments of any one of the aspects described herein, $R^2$ is a labile or leaving group.

$R^3$

In compounds of Formula (I), $R^3$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or a labile or leaving group. For example, $R^3$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^3$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, optionally substituted acyl, carboxyl, hydroxyl, isocyanato, thiocyanato, isothiocyanato, sulfonate, and sulfonyl. For example, $R^3$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^3$ is H, halogen, optionally substituted alkyl, perhaloalkyl, optionally substituted alkenyl, or optionally substituted aryl. For example, $R^3$ is H, halogen, optionally substituted C1-C6alkyl, C1-C6perhaloalkyl $C_1$-$C_6$ optionally substituted alkenyl, or optionally substituted aryl.

In some embodiments of any one of the aspects described herein, $R^3$ is H.

In some embodiments of any one of the aspects described herein, $R^3$ is an optionally substituted $C_1$-$C_6$alkyl. Exemplary alkyls for $R^3$ include, but are not limited to methyl, ethyl, propyl, i-propyl, n-butyl, t-butyl, n-pentyl and hexyl. For example, $R^3$ is methyl.

In some embodiments of any one of the aspects described herein, $R^3$ is an optionally substituted $C_2$-$C_6$alkenyl. For example, $R^3$ is —CH=CH—$R^{9A}$, where $R^{9A}$ is an optionally substituted aryl, optionally substituted heteroaryl, optionally substituted cycloalkyl or optionally substituted hetero cyclyl.

In some embodiments of any one of the aspects described herein, $R^3$ is —CH=CH—$R^{9A}$, where $R^{9A}$ is an optionally substituted aryl or optionally substituted heteroaryl. For example, $R^3$ is —CH=CH—$R^{9A}$, where $R^{9A}$ is an optionally substituted aryl. Exemplary aryls for the $R^{9A}$ group include, but are not limited to, phenyl, naphthyl, anthryl, phenanthryl, anthracyl, indenyl, azulenyl, and fluorenyl, each of which can be optionally substituted with one or more substituents independently selected from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, $R^3$ is —CH=CH—$R^{9A}$, where $R^{9A}$ is an optionally substituted phenyl. For example, $R^3$ is —CH=CH—$R^{9A}$, where $R^{9A}$ is phenyl or phenyl substituted with a substituent (e.g., 1, 2 or 3 substituents) selected from the group consisting of nitro, cyano, halogen, amino, alkylamino, dialkylamino, carboxyl, C1-C6alkyl, C1-C6perhaloalkyl and $C_1$-$C_6$haloalkyl. In some embodiments, $R^3$ is —CH=CH—$R^{9A}$, where $R^{9A}$ is 4-fluoropheyl, 4-trifluoromethylphenyl or 4-cyanophenyl.

In some embodiments of any one of the aspects described herein, $R^3$ is halogen. For example, $R^3$ is Br, Cl or F. In some embodiments, $R^3$ is Br or Cl.

In some embodiments of any one of the aspects described herein, $R^3$ is an optionally substituted aryl or optionally substituted heteroaryl. For example, $R^3$ is an optionally substituted aryl. Exemplary aryls for the $R^3$ group include, but are not limited to, phenyl, naphthyl, anthryl, phenanthryl, anthracyl, indenyl, azulenyl, and fluorenyl, each of which can be optionally substituted with one or more substituents independently selected from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments, $R^3$ is phenyl or naphthyl, each of which can be optionally substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl or aryl. For example, $R^3$ is phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthtyl.

In some embodiments of any one of the aspects described herein, $R^3$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthtyl.

In some embodiments of any one of the aspects described herein, $R^3$ is a labile or leaving group.

$R^5$

In compounds of Formula (I), $R^5$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or a labile or leaving group. For example, $R^5$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^5$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, optionally substituted acyl, carboxyl, hydroxyl, isocyanato, thiocyanato, isothiocyanato, sulfonate, and sulfonyl. For example, $R^5$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^5$ is H, halogen, optionally substituted alkyl, perhaloalkyl, optionally substituted alkenyl, or optionally substituted aryl. For example, $R^5$ is H, halogen, optionally substituted C1-C6alkyl, C1-C6perhaloalkyl $C_1$-$C_6$ optionally substituted alkenyl, or optionally substituted aryl.

In some embodiments of any one of the aspects described herein, $R^5$ is H.

In some embodiments of any one of the aspects described herein, $R^5$ is an optionally substituted $C_1$-$C_6$alkyl. Exemplary alkyls for $R^5$ include, but are not limited to methyl, ethyl, propyl, i-propyl, n-butyl, t-butyl, n-pentyl and hexyl. For example, $R^5$ is methyl.

In some embodiments of any one of the aspects described herein, $R^5$ is an optionally substituted $C_2$-$C_6$alkenyl. For example, $R^5$ is —CH=CH—$R^{9B}$, where $R^{9B}$ is an optionally substituted aryl, optionally substituted heteroaryl, optionally substituted cycloalkyl or optionally substituted hetero cyclyl.

In some embodiments of any one of the aspects described herein, $R^5$ is —CH=CH—$R^{9B}$, where $R^{9B}$ is an optionally substituted aryl or optionally substituted heteroaryl. For example, $R^5$ is —CH=CH—$R^{9B}$, where $R^{9B}$ is an optionally substituted aryl. Exemplary aryls for the $R^{9B}$ group include, but are not limited to, phenyl, naphthyl, anthryl, phenanthryl, anthracyl, indenyl, azulenyl, and fluorenyl, each of which can be optionally substituted with one or more substituents independently selected from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, $R^5$ is —CH=CH—$R^{9B}$, where $R^{9B}$ is an optionally substituted phenyl. For example, $R^5$ is —CH=CH—$R^{9B}$, where $R^{9B}$ is phenyl or phenyl substituted with a substituent (e.g., 1, 2 or 3 substituents) selected from the group consisting of nitro, cyano, halogen, amino, alkylamino, dialkylamino, carboxyl, C1-C6alkyl, C1-C6perhaloalkyl and $C_1$-$C_6$haloalkyl. In some embodiments, $R^5$ is —CH=CH—$R^{9B}$, where $R^{9B}$ is 4-fluoropheyl, 4-trifluoromethylphenyl or 4-cyanophenyl.

In some embodiments of any one of the aspects described herein, $R^5$ is halogen. For example, $R^5$ is Br, Cl or F. In some embodiments, $R^5$ is Br or Cl.

In some embodiments of any one of the aspects described herein, $R^5$ is an optionally substituted aryl or optionally substituted heteroaryl. For example, $R^5$ is an optionally substituted aryl. Exemplary aryls for the $R^5$ group include, but are not limited to, phenyl, naphthyl, anthryl, phenanthryl, anthracyl, indenyl, azulenyl, and fluorenyl, each of which can be optionally substituted with one or more substituents independently selected from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments, $R^5$ is phenyl or naphthyl, each of which can be optionally substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl or aryl. For example, $R^5$ is phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthtyl.

In some embodiments of any one of the aspects described herein, $R^5$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthtyl.

In some embodiments of any one of the aspects described herein, $R^3$ is a labile or leaving group.

It is noted $R^3$ and $R^5$ can be same or different. Accordingly, in some embodiments of any one of the aspects described herein, $R^3$ and $R^5$ are same. In some other embodiments of any one of the aspects described herein, $R^3$ and $R^5$ are different.

$R^6$

In compounds of Formula (I), $R^6$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or a labile or leaving group. For example, $R^6$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^6$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, optionally substituted acyl, carboxyl, hydroxyl, isocyanato, thiocyanato, isothiocyanato, sulfonate, and sulfonyl. For example, $R^6$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^6$ is H, halogen, optionally substituted alkyl, perhaloalkyl, carbonyl, carboxyl, optionally substituted acyl, sulfonate, or sulfonyl. For example, $R^6$ can be H, halogen, optionally substituted $C_1$-$C_6$ alkyl, —C(O)H, or —SO$_3$H.

In some embodiments of any one of the aspects described herein, $R^6$ is H, Br, Cl, —C(O)H, or —SO$_3$H.

In some embodiments of any one of the aspects described herein, $R^6$ is a labile or leaving group.

It is noted that $R^2$ and $R^6$ can be same or different. Accordingly, in some embodiments of any one of the aspects described herein, $R^2$ and $R^6$ are the same. In some other embodiments of any one of the aspects described herein, $R^2$ and $R^6$ are different.

$R^7$

In compounds of Formula (I), $R^7$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or a labile or leaving group. For example, $R^7$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^7$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, carboxyl, hydroxyl, isocyanato, thiocyanato, isothiocyanato, sulfonate, and sulfonyl. For example, $R^7$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^7$ is H, halogen, or optionally substituted optionally substituted alkyl. For example, $R^7$ is H. In some other non-limiting examples, $R^7$ is an optionally substituted $C_1$-$C_6$alkyl. Exemplary alkyls for $R^7$ include, but are not limited to methyl, ethyl, propyl, i-propyl, n-butyl, t-butyl, n-pentyl and hexyl.

In some embodiments of any one of the aspects described herein, $R^7$ is H or methyl.

In some embodiments of any one of the aspects described herein, $R^7$ is a labile or leaving group.

It is noted that $R^1$ and $R^7$ can be same or different. Accordingly, in some embodiments of any one of the aspects described herein, $R^1$ and $R^7$ are the same. In some other embodiments of any one of the aspects described herein, $R^1$ and $R^7$ are different.

In some embodiments of any one of the aspects described herein, at least one of $R^1$, $R^2$, $R^3$, $R^5$, $R^6$ and $R^7$ is not H. In some non-limiting examples, $R^1$ is not H. In some other non-limiting examples, $R^2$ is not H. In yet some other non-limiting examples, $R^3$ is not H. In still some other non-limiting examples, $R^5$ is not H. In yet some other none-limiting example, $R^6$ is not H. In still some other non-limiting examples, $R^7$ is not H.

In some embodiments of any one of the aspects described herein, at least one of $R^1$, $R^2$, $R^3$, $R^5$, $R^6$ and $R^7$ is an electron-withdrawing group (EWG). The term "electron-withdrawing group" is recognized in the art and denotes an atom or group that functions to withdraw electrons from neighboring atoms, i.e., the substituent is electronegative with respect to neighboring atoms. Exemplary electron-withdrawing groups include, but are not limited to halo (e.g., bromo, fluoro, chloro, and iodo), nitro, carboxy, ester, formyl, keto, azo, amidocarbonyl, amidosulfonyl, carboxamido, sulfonoxy, sulfonamide, ureido, and aryl. In some non-limiting examples, $R^1$ is an EWG. In some other non-limiting examples, $R^2$ is an EWG. In yet some other non-limiting examples, $R^3$ is an EWG. In still some other non-limiting examples, $R^5$ is an EWG. In yet some other none-limiting example, $R^6$ is an EWG. In still some other non-limiting examples, $R^7$ is an EWG.

In some embodiments of any one of the aspects described herein, at least one of $R^1$, $R^2$, $R^3$, $R^5$, $R^6$ and $R^7$ is an electron donating group (EDG). The term "electron donating group" is recognized in the art, and denotes an atom or group that functions to donate electrons to neighboring atoms by means of a difference in electronegativity with respect to the neighboring atom (inductive effect) and/or by donating of pi-electrons via conjugation (mesomeric effect). Exemplary electron donating groups include, but are not limited to hydroxyl, lower alkoxy (e.g., methoxy, ethoxy and the like), lower alkyl (such as methyl, ethyl, and the like), amino, lower alkylamino, di-lower alkylamino, aryloxy (such as phenoxy and the like), arylalkoxy (such as phenoxy and the like), aminoaryls (such as p-dimethylaminophenyl and the like), mercapto, and alkylthio. In some non-limiting examples, $R^1$ is an EDG. In some other non-limiting examples, $R^2$ is an EDG. In yet some other non-limiting examples, $R^3$ is an EDG. In still some other non-limiting examples, $R^5$ is an EDG. In yet some other none-limiting example, $R^6$ is an EDG. In still some other non-limiting examples, $R^7$ is an EDG.

In some embodiments of any one of the aspects described herein, at least two of $R^1$, $R^2$ and $R^3$ are same. For example, $R^1$ and $R^2$ are same. In some other examples, $R^1$ and $R^3$ are same. In yet some other example, $R^2$ and $R^3$ are same. In some embodiments, $R^1$, $R^2$ and $R^3$ are same.

In yet some other embodiments, $R^1$, $R^2$ and $R^3$ are different.

In some embodiments of any one of the aspects described herein, at least two of $R^5$, $R^6$ and $R^7$ are same. For example, $R^5$ and $R^6$ are same. In some other examples, $R^5$ and $R^7$ are same. In yet some other example, $R^6$ and $R^7$ are same. In some embodiments, $R^5$, $R^6$ and $R^7$ are same.

In yet some other embodiments, $R^5$, $R^6$ and $R^7$ are different.

In some embodiments of any one of the aspects described herein, $R^1$ and $R^7$ are different, or $R^2$ and $R^6$ are different, or $R^3$ and $R^5$ are different.

In some embodiments of any one of the aspects described herein, $R^1$ and $R^7$ are same, $R^2$ and $R^6$ are same, and $R^3$ and $R^5$ are same.

In some embodiments of any one of the aspects described herein, $R^1$, $R^2$, $R^3$, $R^5$, $R^6$ and $R^7$ are same. For example, $R^1$, $R^2$, $R^3$, $R^5$, $R^6$ and $R^7$ are H.

In some embodiments of the various aspects described herein, when $R^{8S}$ is methyl then: (a) $R^1$, $R^2$, $R^3$, $R^5$, $R^6$ and $R^7$ are not H; (b) $R^1$, $R^2$, $R^6$ and $R^7$ are not H, and $R^3$ and $R^5$ are not methyl, ethyl or p-nitrophenyl; (c) $R^1$, $R^3$, $R^5$ and $R^7$ are not methyl, and $R^2$ and $R^6$ are not H; (d) $R^1$ and $R^7$ are not H, and $R^2$, $R^3$, $R^5$ and $R^6$ are not Cl or Br; (e) $R^1$, $R^3$, $R^5$, $R^6$ and $R^7$ are not H, and $R^2$ is not —C(O)H; (f) $R^1$ is not p-nitrophenyl, $R^2$, $R^6$ and $R^7$ are not H, and $R^3$ and $R^5$ are not methyl; and/or (g) $R^1$, $R^2$, $R^5$, $R^6$ and $R^7$ are not H, and $R^3$ is not phenyl, p-nitrophenyl, p-iodophenyl, p-carboxylicphenyl or p-methoxyphenyl.

In some embodiments of the various aspects described herein, when $R^{8S}$ is allyl, ethyl, propyl, butyl, t-butyl, n-dodecyl, phenyl, 2,6-dimethylphenyl, p-methylphenyl, p-methoxyphenyl, p-nitrophenyl or benzyl (—CH$_2$PH) then $R^1$, $R^2$, $R^3$, $R^5$, $R^6$ and $R^7$ are not H.

In some embodiments of the various aspects described herein, when $R^8$ is Cl then: (a) $R^1$, $R^2$, $R^3$, $R^5$, $R^6$ and $R^7$ are not H; (b) $R^1$, $R^3$, $R^5$, $R^6$ and $R^7$ are not H, and $R^2$ is not Cl; (c) $R^1$, $R^3$, $R^5$ and $R^7$ are not H, and $R^2$ and $R^5$ are not Cl; (d) $R^1$, $R^5$ and $R^7$ are not H, and $R^2$, $R^3$ and $R^5$ are not Cl; and/or (e) $R^1$, $R^2$, $R^3$, $R^5$, $R^6$ and $R^7$ are not Cl.

In some embodiments of any one of the aspects described herein, the compound of Formula (I) exhibits different fluorescent spectral properties when covalently or non-covalently conjugated to an amino acid. Without being limited by theory, it is believed that the atomic interactions induced by different amino acid side-chains affect the electronic (ground or activation) states of the probe conjugated to a particular amino acid; thereby leading to different fluorescent spectral properties.

$R^{31}$

In some embodiments of any one of the aspects described herein, $R^{31}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{31}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{31}$ is hydrogen, halogen, alkoxyl, aryl, amino, alkylamino, dialkylamino, hydroxyl, carboxyl, cynao, nitro, thiol, alkylthio, or sulfonate. For example, $R^{31}$ is hydrogen, halogen, alkoxyl, aryl, amino, hydroxyl, carboxyl, cynao, nitro, or thiol. In some embodiments, $R^{31}$ is hydrogen, methyl, ethyl, trifluomethyl, cyano, hydroxyl, methoxy, or phenyl. For example, $R^{31}$ is hydrogen, methyl, ethyl, trifluomethyl, phenyl or cyano. In some embodiments, $R^{31}$ is hydrogen, methyl or ethyl.

$R^{32}$

In some embodiments of any one of the aspects described herein, $R^{32}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{32}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{32}$ is hydrogen, halogen, alkoxyl, aryl, amino, alkylamino, dialkylamino, hydroxyl, carboxyl, cynao, nitro, thiol, alkylthio, or sulfonate. For example, $R^{32}$ is hydrogen, halogen, alkoxyl, aryl, amino, hydroxyl, carboxyl, cynao, nitro, or thiol. In some embodiments, $R^{32}$ is hydrogen, methyl, ethyl, trifluomethyl, cyano, hydroxyl, methoxy, or phenyl. For example, $R^{32}$ is hydrogen, methyl, ethyl, trifluomethyl, phenyl or cyano. In some embodiments, $R^{32}$ is hydrogen or methyl.

$R^{33}$

In some embodiments of any one of the aspects described herein, $R^{33}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{33}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{33}$ is hydrogen, halogen, alkoxyl, aryl, amino, alkylamino, dialkylamino, hydroxyl, carboxyl, cynao, nitro, thiol, alkylthio, or sulfonate. For example, $R^{33}$ is hydrogen, halogen, alkoxyl, aryl, amino, hydroxyl, carboxyl, cynao, nitro, or thiol. In some embodiments, $R^{33}$ is hydrogen, F, Br, Cl, I, methyl, ethyl, trifluomethyl, cyano, hydroxyl, methoxy, or phenyl. For example, $R^{33}$ is hydrogen, F, methyl, ethyl, trifluomethyl, phenyl or cyano. In some embodiments, $R^{33}$ is hydrogen, F, methyl, trifluoromethyl or phenyl.

In some embodiments, $R^{32}$ and $R^{33}$, together with the carbon atoms they are attached to form an optionally substituted aryl.

$R^{34}$

In some embodiments of any one of the aspects described herein, $R^{34}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{34}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{34}$ is hydrogen, halogen, alkoxyl, aryl, amino, alkylamino, dialkylamino, hydroxyl, carboxyl, cynao, nitro, thiol, alkylthio, or sulfonate. For example, $R^{34}$ is hydrogen, halogen, alkoxyl, aryl, amino, hydroxyl, carboxyl, cynao, nitro, or thiol. In some embodiments, $R^{34}$ is hydrogen, methyl, ethyl, trifluomethyl, cyano, hydroxyl, methoxy, or phenyl. For example, $R^{34}$ is hydrogen, methyl, ethyl, trifluomethyl, phenyl or cyano. In some embodiments, $R^{34}$ is hydrogen or methyl.

In some embodiments, $R^{33}$ and $R^{34}$, together with the carbon atoms they are attached to form an optionally substituted aryl.

$R^{35}$

In some embodiments of any one of the aspects described herein, $R^{35}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{35}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{35}$ is hydrogen, halogen, alkoxyl, aryl, amino, alkylamino, dialkylamino, hydroxyl, carboxyl, cynao, nitro, thiol, alkylthio, or sulfonate. For example, $R^{35}$ is hydrogen, halogen, alkoxyl, aryl, amino, hydroxyl, carboxyl, cynao, nitro, or thiol. In some embodiments, $R^{35}$ is hydrogen, methyl, ethyl, trifluomethyl, cyano, hydroxyl, methoxy, or phenyl. For example, $R^{35}$ is hydrogen, methyl, ethyl, trifluomethyl, phenyl or cyano. In some embodiments, $R^{35}$ is hydrogen, methyl or ethyl.

$R^{41}$

In some embodiments of any one of the aspects described herein, $R^{41}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{41}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{41}$ is hydrogen, halogen, alkoxyl, aryl, amino, alkylamino, dialkylamino, hydroxyl, carboxyl, cynao, nitro, thiol, alkylthio, or sulfonate. For example, $R^{41}$ is hydrogen, halogen, alkoxyl, aryl, amino, hydroxyl, carboxyl, cynao, nitro, or thiol. In some embodiments, $R^{41}$ is hydrogen, methyl, ethyl, trifluomethyl, cyano, hydroxyl, methoxy, or phenyl. For example, $R^{41}$ is hydrogen, methyl, ethyl, trifluomethyl, phenyl or cyano. In some embodiments, $R^{41}$ is hydrogen, methyl or ethyl.

$R^{42}$

In some embodiments of any one of the aspects described herein, $R^{42}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{42}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{42}$ is hydrogen, halogen, alkoxyl, aryl, amino, alkylamino, dialkylamino, hydroxyl, carboxyl, cynao, nitro, thiol, alkylthio, or sulfonate. For example, $R^{42}$ is hydrogen, halogen, alkoxyl, aryl, amino, hydroxyl, carboxyl, cynao, nitro, or thiol. In some embodiments, $R^{42}$ is hydrogen, methyl, ethyl, trifluomethyl, cyano, hydroxyl, methoxy, or phenyl. For example, $R^{42}$ is hydrogen, methyl, ethyl, trifluomethyl, phenyl or cyano. In some embodiments, $R^{42}$ is hydrogen or methyl.

$R^{43}$

In some embodiments of any one of the aspects described herein, $R^{43}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{43}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{43}$ is hydrogen, halogen, alkoxyl, aryl, amino, alkylamino, dialkylamino, hydroxyl, carboxyl, cynao, nitro, thiol, alkylthio, or sulfonate. For example, $R^{43}$ is hydrogen, halogen, alkoxyl, aryl, amino, hydroxyl, carboxyl, cynao, nitro, or thiol. In some embodiments, $R^{43}$ is hydrogen, F, Br, Cl, I, methyl, ethyl, trifluomethyl, cyano, hydroxyl, methoxy, or phenyl. For example, $R^{43}$ is hydrogen, F, methyl, ethyl, trifluomethyl, phenyl or cyano. In some embodiments, $R^{43}$ is hydrogen, F, methyl, trifluoromethyl or phenyl.

In some embodiments, $R^{42}$ and $R^{43}$, together with the carbon atoms they are attached to form an optionally substituted aryl.

$R^{44}$

In some embodiments of any one of the aspects described herein, $R^{44}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{44}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{44}$ is hydrogen, halogen, alkoxyl, aryl, amino, alkylamino, dialkylamino, hydroxyl, carboxyl, cynao, nitro, thiol, alkylthio, or sulfonate. For example, $R^{44}$ is hydrogen, halogen, alkoxyl, aryl, amino, hydroxyl, carboxyl, cynao, nitro, or thiol. In some embodiments, $R^{44}$ is hydrogen, methyl, ethyl, trifluomethyl, cyano, hydroxyl, methoxy, or phenyl. For example, $R^{44}$ is hydrogen, methyl, ethyl, trifluomethyl, phenyl or cyano. In some embodiments, $R^{44}$ is hydrogen or methyl.

In some embodiments, $R^{43}$ and $R^{44}$, together with the carbon atoms they are attached to form an optionally substituted aryl.

$R^{45}$

In some embodiments of any one of the aspects described herein, $R^{45}$ is hydrogen, halogen, alkyl, perhaloalkyl, alkenyl, alkynyl, alkoxyl, aryl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{45}$ is hydrogen, halogen, alkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{45}$ is hydrogen, halogen, alkoxyl, aryl, amino, alkylamino, dialkylamino, hydroxyl, carboxyl, cynao, nitro, thiol, alkylthio, or sulfonate. For example, $R^{45}$ is hydrogen, halogen, alkoxyl, aryl, amino, hydroxyl, carboxyl, cynao, nitro, or thiol. In some embodiments, $R^{45}$ is hydrogen, methyl, ethyl, trifluomethyl, cyano, hydroxyl, methoxy, or phenyl. For example, $R^{45}$ is hydrogen, methyl, ethyl, trifluomethyl, phenyl or cyano. In some embodiments, $R^{45}$ is hydrogen, methyl or ethyl.

$R^{81}$

In some embodiments of any one of the aspects described herein, $R^{81}$ is hydrogen, halogen, alkyl, perhaloalkyl, alkenyl, alkynyl, alkoxyl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{81}$ is hydrogen, halogen, alkyl, perhaloalkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{81}$ is hydrogen, halogen, alkoxyl, amino, alkylamino, dialkylamino, hydroxyl, carboxyl, cynao, nitro, thiol, alkylthio, or sulfonate. For example, $R^{81}$ is hydrogen, halogen, alkoxyl, amino, hydroxyl, carboxyl, cynao, nitro, or thiol. In some embodiments, $R^{81}$ is hydrogen.

$R^{82}$

In some embodiments of any one of the aspects described herein, $R^{82}$ is hydrogen, halogen, alkyl, perhaloalkyl, alkenyl, alkynyl, alkoxyl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{82}$ is hydrogen, halogen, alkyl, perhaloalkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{82}$ is hydrogen, halogen, alkoxyl, amino, alkylamino, dialkylamino, hydroxyl, carboxyl, cynao, nitro, thiol, alkylthio, or sulfonate. For example, $R^{82}$ is hydrogen, halogen, alkoxyl, amino, hydroxyl, carboxyl, cynao, nitro, or thiol. In some embodiments, $R^{82}$ is hydrogen.

$R^{83}$

In some embodiments of any one of the aspects described herein, $R^{83}$ is hydrogen, halogen, alkyl, perhaloalkyl, alkenyl, alkynyl, alkoxyl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{83}$ is hydrogen, halogen, alkyl, perhaloalkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{83}$ is hydrogen, halogen, alkoxyl, amino, alkylamino, dialkylamino, hydroxyl, carboxyl, cynao, nitro, thiol, alkylthio, or sulfonate. For example, $R^{83}$ is hydrogen, halogen, alkoxyl, amino, hydroxyl, carboxyl, cynao, nitro, or thiol. In some embodiments, $R^{83}$ is halogen or alkoxyl. For example, $R^{83}$ is F, Cl, Br, I, methoxy or ethoxy. In some embodiments, $R^{83}$ is fluoro or methoxy.

$R^{84}$

In some embodiments of any one of the aspects described herein, $R^{84}$ is hydrogen, halogen, alkyl, perhaloalkyl, alkenyl, alkynyl, alkoxyl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{84}$ is hydrogen, halogen, alkyl, perhaloalkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{84}$ is hydrogen, halogen, alkoxyl, amino, alkylamino, dialkylamino, hydroxyl, carboxyl, cynao, nitro, thiol, alkylthio, or sulfonate. For example, $R^{84}$ is hydrogen, halogen, alkoxyl, amino, hydroxyl, carboxyl, cynao, nitro, or thiol. In some embodiments, $R^{84}$ is hydrogen.

$R^{85}$

In some embodiments of any one of the aspects described herein, $R^{85}$ is hydrogen, halogen, alkyl, perhaloalkyl, alkenyl, alkynyl, alkoxyl, amino, alkylamino, dialkylamino, hydroxyl, acyl, acyloxy, carbonyl, carboxyl, ester, cynao, nitro, thiol, alkylthio, sulfonate, sulfinyl, sulfonyl, carbamoyl, isocyanato, thiocyanato, isothiocyanato, or ureido. For example, $R^{85}$ is hydrogen, halogen, alkyl, perhaloalkyl, alkoxyl, amino, alkylamino, dialkylamino, hydroxyl, carbonyl, carboxyl, ester, cynao, nitro, thiol, alkylthio, or sulfonate. In some embodiments of any one of the aspects described herein, $R^{85}$ is hydrogen, halogen, alkoxyl, amino, alkylamino, dialkylamino, hydroxyl, carboxyl, cynao, nitro, thiol, alkylthio, or sulfonate. For example, $R^{85}$ is hydrogen, halogen, alkoxyl, amino, hydroxyl, carboxyl, cynao, nitro, or thiol. In some embodiments, $R^{85}$ is hydrogen.

BOPIDY Amino Acid (Peptide, Polypeptide) Conjugates

In another aspect, provided herein is a compound of Formula (II):

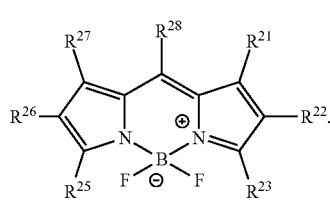

(Formula II)

In compounds of Formula (II), $R^{21}$, $R^{22}$, $R^{23}$, $R^{24}$, $R^{25}$, $R^{26}$, $R^{27}$ and $R^{28}$ are each independently selected from the group consisting of hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfonate, sulfinyl, sulfonyl, carbamoyl, isocyanato, thiocyanato, isothiocyanato, ureido, and an amino acid, optionally at least one of $R^{21}$, $R^{22}$, $R^{23}$, $R^{24}$, $R^{25}$, $R^{26}$, $R^{27}$ and $R^{28}$, is an amino acid. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

As used herein, the term "amino acid" refers to any organic molecule that contains at least one amino group and at least one carboxyl group. Typically, at least one amino group is at the a position relative to a carboxyl group. As used herein, the term "amino acid" includes naturally occurring amino acids, L-amino acids, D-amino acids, synthetic amino acids, modified amino acids (such as hydroxyproline, γ-carboxyglutamate and O-phosphoserine), as well as amino acid analogs and amino acid mimetics that function in a similar manner as naturally occurring amino acids. An amino acid analog refers to a compound having the same basic chemical structure as a naturally occurring amino acid, such as an a carbon, a carboxyl group, an amino group and an R group bonded to hydrogen, such as homoserine, norleucine, methionine sulfoxide, methionine methylsulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of amino acids but that functions similarly to naturally occurring amino acids.

It is noted the amino acid can be a single amino acid or part of an oligopeptide (e.g., comprising 2-20 amino acids, such as a di-, tri-, tetra-, penta-, hexa-, hepta-, octa-, nona- or deca-peptide), a polypeptide (e.g., comprising 21 or more amino acids peptide). One of ordinary skill in the art is well aware that a polypeptide that contains more than approximately fifty amino acids is known as a protein. Thus, the term "polypeptide" as used herein includes proteins. Further, the amino acid can be linked to rest of Formula (II) by its a amino group, the carboxyl group or a functional group in the side chain. In some preferred embodiments, the amino acid is linked to rest of Formula (II) by its a amino group.

In some embodiments of any one of the aspects described herein, only one of $R^{21}$, $R^{22}$, $R^{23}$, $R^{24}$, $R^{25}$, $R^{26}$, $R^{27}$ and $R^{28}$ is an amino acid.

In some embodiments of any one of the aspects described herein, $R^{21}$, $R^{22}$, $R^{23}$, $R^{24}$, $R^{25}$, $R^{26}$ and $R^{27}$ each independently selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, and ureido; and $R^{28}$ is an amino acid.

$R^{28}$

In some embodiments of any one of the aspects described herein, $R^{28}$ is an amino acid. For example, $R^{28}$ is —NHCH($R^{AS}$)C(O)—$OR^{AC}$ or —OC(O)CH($R^{AS}$)NHR$^{AN}$, where each $R^{AC}$ is H, an amino acid, a peptide, a polypeptide or a hydroxyl protecting group; $R^{AS}$ is side chain of amino acid; and $R^{AN}$ is H, an amino acid, a peptide a polypeptide or an amino protecting group.

In some embodiments, $R^{28}$ is —NHCH($R^{AS}$)C(O)—$OR^{AC}$, where $R^{AC}$ is H, an amino acid, a peptide, a polypeptide or a hydroxyl protecting group; and $R^{AS}$ is side chain of amino acid. For example, $R^{AC}$ is H or a hydroxyl protecting group. Preferably, $R^{AC}$ is H.

In some embodiments, $R^{28}$ is or —OC(O)CH($R^{AS}$)NHR$^{AN}$, where $R^{AS}$ is side chain of amino acid; and $R^{AN}$ is H, an amino acid, a peptide a polypeptide or an amino protecting group. For example, $R^{AN}$ is H or an amino protecting group. Preferably, $R^{AN}$ is H.

In some embodiments of any one of the aspects described herein, the compound of Formula (II) is of Formula (II-a) or (II-b)

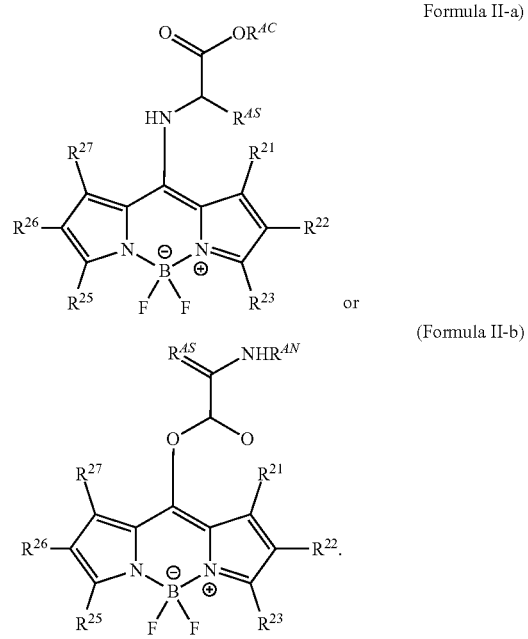

In compounds of Formulae (II-a) and (II-b), each $R^{AC}$ is H, an amino acid, a peptide, a polypeptide or a hydroxyl protecting group; $R^{AS}$ is side chain of amino acid; and $R^{AN}$ is H, an amino acid, a peptide a polypeptide or an amino protecting group.

$R^{21}$

In compounds of Formula (II), $R^{21}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or an amino acid. For example, $R^{21}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^{21}$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, carboxyl, hydroxyl, isocyanato, thiocyanato, isothiocyanato, sulfonate, and sulfonyl. For example, $R^{21}$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^{21}$ is H, halogen, or optionally substituted optionally substituted alkyl. For example, $R^{21}$ is H. In some other non-limiting examples, $R^{21}$ is an optionally substituted $C_1$-$C_6$alkyl. Exemplary alkyls for $R^{21}$ include, but are not limited to methyl, ethyl, propyl, i-propyl, n-butyl, t-butyl, n-pentyl and hexyl.

In some embodiments of any one of the aspects described herein, $R^{21}$ is H or methyl.

In some embodiments of any one of the aspects described herein, $R^{21}$ is an amino acid.

$R^{22}$

In compounds of Formula (II), $R^{22}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or an amino acid. For example, $R^{22}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^{22}$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, optionally substituted acyl, carboxyl, hydroxyl, isocyanato, thiocyanato, isothiocyanato, sulfonate, and sulfonyl. For example, $R^{22}$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^{22}$ is H, halogen, optionally substituted alkyl, perhaloalkyl, carbonyl, carboxyl, optionally substituted acyl, sulfonate, or sulfonyl. For example, $R^{22}$ can be H, halogen, optionally substituted $C_1$-$C_6$ alkyl, —C(O)H, or —SO$_3$H.

In some embodiments of any one of the aspects described herein, $R^{22}$ is H, Br, Cl, —C(O)H, or —SO$_3$H.

In some embodiments of any one of the aspects described herein, $R^{22}$ is an amino acid.

$R^{23}$

In compounds of Formula (II), $R^{23}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or an amino acid. For example, $R^{23}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^{23}$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, optionally substituted acyl, carboxyl, hydroxyl, isocyanato, thiocyanato, isothiocyanato, sulfonate, and sulfonyl. For example, $R^{23}$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^{23}$ is H, halogen, optionally substituted alkyl, perhaloalkyl, optionally substituted alkenyl, or optionally substituted aryl. For example, $R^{23}$ is H, halogen, optionally substituted C1-C6alkyl, C1-C6perhaloalkyl $C_1$-$C_6$ optionally substituted alkenyl, or optionally substituted aryl.

In some embodiments of any one of the aspects described herein, $R^{23}$ is H.

In some embodiments of any one of the aspects described herein, $R^{23}$ is an optionally substituted $C_1$-$C_6$alkyl. Exemplary alkyls for $R^{23}$ include, but are not limited to methyl, ethyl, propyl, i-propyl, n-butyl, t-butyl, n-pentyl and hexyl. For example, $R^{23}$ is methyl.

In some embodiments of any one of the aspects described herein, $R^{23}$ is an optionally substituted $C_2$-$C_6$alkenyl. For example, $R^{23}$ is —CH=CH—$R^{29}$, where $R^{29}$ is an optionally substituted aryl, optionally substituted heteroaryl, optionally substituted cycloalkyl or optionally substituted hetero cyclyl.

In some embodiments of any one of the aspects described herein, $R^{23}$ is —CH=CH—$R^{29A}$ where $R^{29A}$ is an optionally substituted aryl or optionally substituted heteroaryl. For example, $R^{23}$ is —CH=CH—$R^{29A}$, where $R^{29A}$ is an optionally substituted aryl. Exemplary aryls for the $R^{29A}$ group include, but are not limited to, phenyl, naphthyl, anthryl, and phenanthryl, each of which can be optionally substituted with one or more substituents independently selected from the group consisting of halogen, hydroxy, caboxy, oxo, nitro, haloalkyl, alkyl, perhaloalkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, $R^{23}$ is —CH=CH—$R^{29A}$ where $R^{29A}$ is an optionally substituted phenyl. For example, $R^{23}$ is —CH=CH—$R^{29A}$, where $R^{29A}$ is phenyl or phenyl substituted with a substituent (e.g., 1, 2 or 3 substituents) selected from the group consisting of nitro, cyano, halogen, amino, alkylamino, dialkylamino, carboxyl, C1-C6alkyl, C1-C6perhaloalkyl and $C_1$-$C_6$haloalkyl. In some embodiments, $R^{23}$ is —CH=CH—$R^{29A}$, where $R^{29A}$ is 4-fluoropheyl, 4-trifluoromethylphenyl or 4-cyanophenyl.

In some embodiments of any one of the aspects described herein, $R^{23}$ is halogen. For example, $R^{23}$ is Br, Cl or F. In some embodiments, $R^{23}$ is Br or Cl.

In some embodiments of any one of the aspects described herein, $R^{23}$ is an optionally substituted aryl or optionally substituted heteroaryl. For example, $R^{23}$ is an optionally substituted aryl. Exemplary aryls for the $R^{23}$ group include, but are not limited to, phenyl, naphthyl, anthryl, and phenanthryl, each of which can be optionally substituted with one or more substituents independently selected from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments, $R^{23}$ is phenyl or naphthyl, each of which can be optionally substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl or aryl. For example, $R^{23}$ is phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthtyl.

In some embodiments of any one of the aspects described herein, $R^{23}$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthtyl.

In some embodiments of any one of the aspects described herein, $R^{23}$ is an amino acid.

$R^{25}$

In compounds of Formula (II), $R^{25}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or an amino acid. For example, $R^{25}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^{25}$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, optionally substituted acyl, carboxyl, hydroxyl, isocyanato, thiocyanato, isothiocyanato, sulfonate, and sulfonyl. For example, $R^{25}$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^{25}$ is H, halogen, optionally substituted alkyl, perhaloalkyl, optionally substituted alkenyl, or optionally substituted aryl. For example, $R^{25}$ is H, halogen, optionally substituted C1-C6alkyl, C1-C6perhaloalkyl $C_1$-$C_6$ optionally substituted alkenyl, or optionally substituted aryl.

In some embodiments of any one of the aspects described herein, $R^{25}$ is H.

In some embodiments of any one of the aspects described herein, $R^{25}$ is an optionally substituted $C_1$-$C_6$alkyl. Exemplary alkyls for $R^{25}$ include, but are not limited to methyl, ethyl, propyl, i-propyl, n-butyl, t-butyl, n-pentyl and hexyl. For example, $R^{25}$ is methyl.

In some embodiments of any one of the aspects described herein, $R^{25}$ is an optionally substituted $C_2$-$C_6$alkenyl. For example, $R^{25}$ is —CH=CH—$R^{29B}$, where $R^{29B}$ is an optionally substituted aryl, optionally substituted heteroaryl, optionally substituted cycloalkyl or optionally substituted hetero cyclyl.

In some embodiments of any one of the aspects described herein, $R^{25}$ is —CH=CH—$R^{29B}$, where $R^{29B}$ is an optionally substituted aryl or optionally substituted heteroaryl. For example, $R^{25}$ is —CH=CH—$R^{29B}$, where $R^{29B}$ is an optionally substituted aryl. Exemplary aryls for the $R^{29B}$ group include, but are not limited to, phenyl, naphthyl, anthryl, and phenanthryl, each of which can be optionally substituted with one or more substituents independently selected from the group consisting of halogen, hydroxy, caboxy, oxo, nitro, haloalkyl, alkyl, perhaloalkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, $R^{25}$ is —CH=CH—$R^{29B}$, where $R^{29B}$ is an optionally substituted phenyl. For example, $R^{25}$ is —CH=CH—$R^{29B}$, where $R^{29B}$ is phenyl or phenyl substituted with a substituent (e.g., 1, 2 or 3 substituents) selected from the group consisting of nitro, cyano, halogen, amino, alkylamino, dialkylamino, carboxyl, C1-C6alkyl, C1-C6perhaloalkyl and $C_1$-$C_6$haloalkyl. In some embodiments, $R^{25}$ is —CH=CH—$R^{29B}$, where $R^{29B}$ is 4-fluoropheyl, 4-trifluoromethylphenyl or 4-cyanophenyl.

In some embodiments of any one of the aspects described herein, $R^{25}$ is halogen. For example, $R^{25}$ is Br, Cl or F. In some embodiments, $R^{25}$ is Br or Cl.

In some embodiments of any one of the aspects described herein, $R^{25}$ is an optionally substituted aryl or optionally substituted heteroaryl. For example, $R^{25}$ is an optionally substituted aryl. Exemplary aryls for the $R^{25}$ group include, but are not limited to, phenyl, naphthyl, anthryl, and phenanthryl, each of which can be optionally substituted with one or more substituents independently selected from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments, $R^{25}$ is phenyl or naphthyl, each of which can be optionally substituted with a substituent selected from the group consisting of nitro, cyano, halogen, amino, alkylamino, dialkylamino, carboxyl, C1-C6alkyl, C1-C6perhaloalkyl C1-C6haloalkyl or aryl. For example, $R^{25}$ is phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthtyl.

In some embodiments of any one of the aspects described herein, $R^{25}$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthtyl.

It is noted $R^{23}$ and $R^{25}$ can be same or different. Accordingly, in some embodiments of any one of the aspects described herein, $R^{23}$ and $R^{25}$ are same. In some other embodiments of any one of the aspects described herein, $R^{23}$ and $R^{25}$ are different.

In some embodiments of any one of the aspects described herein, $R^{25}$ is an amino acid.

$R^{26}$

In compounds of Formula (II), $R^{26}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or an amino acid. For example, $R^{26}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^{26}$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, optionally substituted acyl, carboxyl, hydroxyl, isocyanato, thiocyanato, isothiocyanato, sulfonate, and sulfonyl. For example, $R^{26}$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^{26}$ is H, halogen, optionally substituted alkyl, perhaloalkyl, carbonyl, carboxyl, optionally substituted acyl, sulfonate, or sulfonyl. For example, $R^{26}$ can be H, halogen, optionally substituted $C_1$-$C_6$ alkyl, —C(O)H, or —$SO_3H$.

In some embodiments of any one of the aspects described herein, $R^{26}$ is H, Br, Cl, —C(O)H, or —$SO_3H$.

It is noted that $R^{22}$ and $R^{26}$ can be same or different. Accordingly, in some embodiments of any one of the aspects described herein, $R^{22}$ and $R^{26}$ are the same. In some other embodiments of any one of the aspects described herein, $R^{22}$ and $R^{26}$ are different.

In some embodiments of any one of the aspects described herein, $R^{26}$ is an amino acid.

$R^{27}$

In compounds of Formula (II), $R^{27}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, optionally substituted arylamino, optionally substituted heteroarylamino, hydroxyl, optionally substituted acyl, optionally substituted acyloxy, carbonyl, carboxyl, optionally substituted ester, optionally substituted alkoxyl, cynao, nitro, thiol, optionally substituted alkylthio, sulfonate, sulfinyl, sulfonyl, carbamoyl, isocyanato, thiocyanato, isothiocyanato, ureido or an amino acid. For example, $R^{27}$ can be hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, amino, optionally substituted alkylamino, optionally substituted dialkylamino, hydroxyl, optionally substituted acyl, carbonyl, carboxyl, optionally substituted ester, optionally substituted alkoxyl, cynao, thiol, optionally substituted alkylthio, sulfonate, sulfinyl or sulfonyl.

In some embodiments of any one of the aspects described herein, $R^{27}$ is selected from the group consisting of hydrogen, halogen, optionally substituted alkyl, perhaloalkyl, optionally substituted alkenyl, optionally substituted alkynyl, optionally substituted alkoxyl, optionally substituted aryl, optionally substituted heteroaryl, optionally substituted cycloalkyl, optionally substituted heterocyclyl, cyano, amino, alkylamino, dialkylamino, nitro, carbonyl, carboxyl, hydroxyl, isocyanato, thiocyanato, isothiocyanato, sulfonate, and sulfonyl. For example, $R^{27}$ is H, halogen, optionally substituted optionally substituted alkyl, perhaloalkyl, optionally substituted alkenyl, optionally substituted alkynyl, optionally substituted alkoxyl, carbonyl, optionally substituted acyl, carboxyl, hydroxyl, cyano, amino, nitro, sulfonate, or sulfonyl.

In some embodiments of any one of the aspects described herein, $R^{27}$ is H, halogen, or optionally substituted optionally substituted alkyl. For example, $R^{27}$ is H. In some other non-limiting examples, $R^{27}$ is an optionally substituted $C_1$-$C_6$alkyl. Exemplary alkyls for $R^{27}$ include, but are not limited to methyl, ethyl, propyl, i-propyl, n-butyl, t-butyl, n-pentyl and hexyl.

In some embodiments of any one of the aspects described herein, $R^{27}$ is H or methyl.

In some embodiments of any one of the aspects described herein, $R^{27}$ is an amino acid.

It is noted that $R^{21}$ and $R^{27}$ can be same or different. Accordingly, in some embodiments of any one of the aspects described herein, $R^{21}$ and $R^{27}$ are the same. In some other embodiments of any one of the aspects described herein, $R^{21}$ and $R^{27}$ are different.

In some embodiments of any one of the aspects described herein, at least one of $R^{21}$, $R^{22}$, $R^{23}$, $R^{25}$, $R^{26}$ and $R^{27}$ is not H. In some non-limiting examples, $R^{21}$ is not H. In some other non-limiting examples, $R^{22}$ is not H. In yet other non-limiting examples, $R^{23}$ is not H. In still some other non-limiting examples, $R^{25}$ is not H. In yet some other none-limiting example, $R^{26}$ is not H. In still some other non-limiting examples, $R^{27}$ is not H.

In some embodiments of any one of the aspects described herein, at least one of $R^{21}$, $R^{22}$, $R^{23}$, $R^{25}$, $R^{26}$ and $R^{27}$ is an electron-withdrawing group (EWG). In some non-limiting examples, $R^{21}$ is an EWG. In some other non-limiting examples, $R^{22}$ is an EWG. In yet some other non-limiting examples, $R^{23}$ is an EWG. In still some other non-limiting examples, $R^{25}$ is an EWG. In yet some other none-limiting example, $R^{26}$ is an EWG. In still some other non-limiting examples, $R^{27}$ is an EWG.

In some embodiments of any one of the aspects described herein, at least one of $R^{21}$, $R^{22}$, $R^{23}$, $R^{25}$, $R^{26}$ and $R^{27}$ is an electron donating group (EDG).

In some non-limiting examples, $R^{21}$ is an EDG. In some other non-limiting examples, $R^{22}$ is an EDG. In yet some other non-limiting examples, $R^{23}$ is an EDG. In still some other non-limiting examples, $R^{25}$ is an EDG. In yet some other none-limiting example, $R^{26}$ is an EDG. In still some other non-limiting examples, $R^{27}$ is an EDG.

In some embodiments of any one of the aspects described herein, at least two of $R^{21}$, $R^{22}$ and $R^{23}$ are same. For example, $R^{21}$ and $R^{22}$ are same. In some other examples, $R^{21}$ and $R^{23}$ are same. In yet some other example, $R^{22}$ and $R^{23}$ are same. In some embodiments, $R^{21}$, $R^{22}$ and $R^{23}$ are same.

In yet some other embodiments, $R^{21}$, $R^{22}$ and $R^{23}$ are different.

In some embodiments of any one of the aspects described herein, at least two of $R^{25}$, $R^{26}$ and $R^{27}$ are same. For example, $R^{25}$ and $R^{26}$ are same. In some other examples, $R^{25}$ and $R^{27}$ are same. In yet some other example, $R^{26}$ and $R^{27}$ are same. In some embodiments, $R^{25}$, $R^{26}$ and $R^{27}$ are same.

In yet some other embodiments, $R^{25}$, $R^{26}$ and $R^{27}$ are different.

In some embodiments of any one of the aspects described herein, $R^{21}$ and $R^{27}$ are different, or $R^{22}$ and $R^{26}$ are different, or $R^{23}$ and $R^{25}$ are different.

In some embodiments of any one of the aspects described herein, $R^{21}$ and $R^{27}$ are same, $R^{22}$ and $R^{26}$ are same, and $R^{23}$ and $R^{25}$ are same.

In some embodiments of any one of the aspects described herein, $R^{21}$, $R^{22}$, $R^{23}$, $R^{25}$, $R^{26}$ and $R^{27}$ are same. For example, $R^{21}$, $R^{22}$, $R^{23}$, $R^{25}$, $R^{26}$ and $R^{27}$ are H.

In some embodiments of any one of the aspects described herein, a compound of Formula (II) is of Formula (II-C) or Formula (II-D):

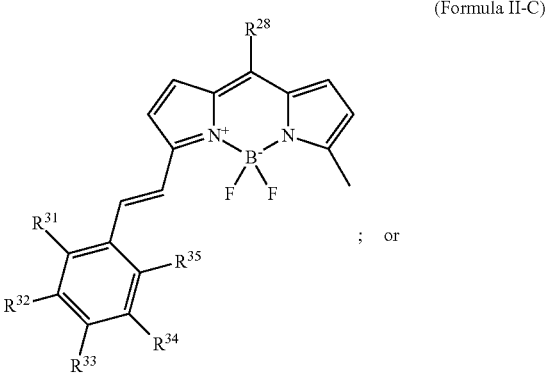

(Formula II-C)

; or

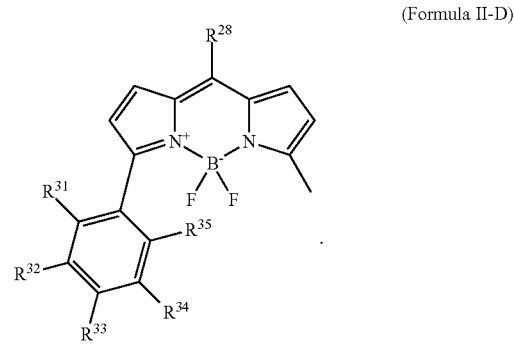

(Formula II-D)

In compounds of Formula (II-C) and (II-D), $R^{28}$ is an amino acid; each of $R^{31}$, $R^{32}$, $R^{33}$, $R^{34}$ and $R^{35}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{31}$, $R^{32}$, $R^{33}$, $R^{34}$ and $R^{35}$, together with the carbon atoms they are attached to form an optionally substituted aryl; and $R^{8S}$ is optionally substituted alkyl, optionally substituted alkenyl, optionally cycloalkyl, optionally substituted heterocyclyl, optionally substituted aryl or optionally substituted heteroaryl. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

In some embodiments of any one of the aspects described herein, a compound of Formula (II) is of Formula (II-E) or Formula (II-F):

(Formula II-E)

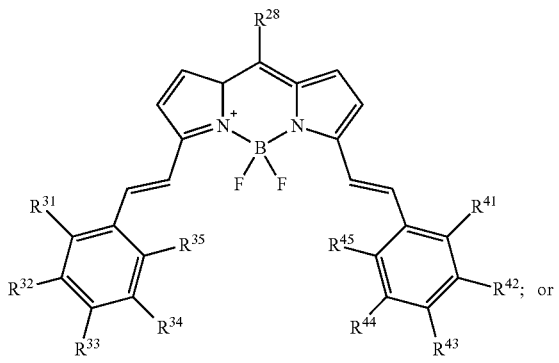

(Formula II-F)

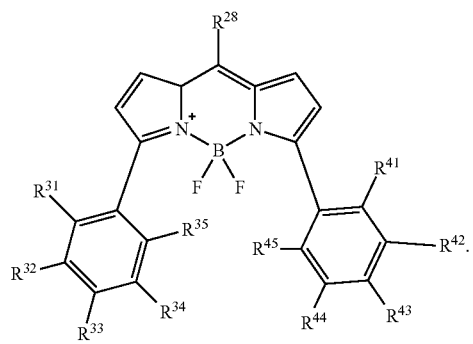

In compounds of Formula (I-G) and (I-H), $R^{28}$ is an amino acid; each of $R^{31}$, $R^{32}$, $R^{33}$, $R^{34}$ and $R^{35}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{31}$, $R^{32}$, $R^{33}$, $R^{34}$ and $R^{35}$, together with the carbon atoms they are attached to form an optionally substituted aryl; each of $R^{41}$, $R^{42}$, $R^{34}$, $R^{44}$ and $R^{45}$ can be independently hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfinyl, sulfonyl, sulfonate, carbamoyl, isocyanato, thiocyanato, isothiocyanato, and ureido, optionally, a vicinal pair of $R^{41}$, $R^{42}$, $R^{34}$, $R^{44}$ and $R^{45}$, together with the carbon atoms they are attached to form an optionally substituted aryl; and $R^{8S}$ is optionally substituted alkyl, optionally substituted alkenyl, optionally cycloalkyl, optionally substituted heterocyclyl, optionally substituted aryl or optionally substituted heteroaryl. It is noted that any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

Spectral Properties

As used herein, the term "spectral properties" refers to a detectable change in the emission intensity, polarity/anisotropy or lifetime at a single wavelength or at a plurality of wavelengths of a probe conjugated to an amino acid relative to one or more different amino acids. Exemplary spectral properties include, but are not limited to, spectral shape or peak intensity and/or polarity. In some embodiments of any one of the aspects described herein, the spectral property is a fluorescence spectral property. As shown in FIGS. 7-22, the fluorescent spectra of exemplary BODIPY probes conjugated to different amino acids exhibited distinctive spectral properties. Comparing the spectra of can therefore be used to identify/detect the amino acid to which the probe is conjugated.

In some embodiments of any one of the aspects described herein, the step of measuring or detecting a spectral property comprises measuring or detecting one or more fluorescent spectral properties of the probe. For example, the step of measuring or detecting a spectral property comprises measuring or detecting fluorescence intensity, polarity/anisotropy or lifetime.

Embodiments of the various aspects described herein include comparing the spectral properties of a conjugated probe to a plurality of reference spectral properties. In some embodiments of any one of the aspects described herein, each reference spectral property is representative of the probe conjugated to a different amino acid. In some embodiments of any one of the aspects described herein, comparing the spectral properties of the conjugated probe to the plurality of reference spectral properties comprises comparing the spectra of the conjugated probe to a plurality of reference spectra. In some embodiments of any one of the aspects described herein, the reference spectra are spectra of the probe bound to known amino acids, such as the spectra shown in FIGS. 7-22. In some embodiments of any one of the aspects described herein, the method comprises identifying the closest match between the spectra of the conjugated probe and the reference spectra, thereby identifying the amino acid. Various statistical methods known in the art can be used to compare the spectra of the conjugated probe and reference spectra in order to identify the closest match and the amino acid conjugated with the probe.

In some embodiments of any one of the aspects described herein, suitable methods generate a quantitative measure of similarity or difference between the spectra and the reference spectra. In some embodiments of any one of the aspects described herein, the methods described herein amino acid conjugated to the probe. In some embodiments of any one of the aspects described herein, the methods used herein for comparing the spectral properties of minal amino acid-probe conjugate and a reference/control conjugate use one or more probabilistic algorithms. For example, a probabilistic algorithm can be trained to identify different amino acids conjugated to probes described herein using the spectral data provided in FIGS. 7-22 associating specific spectra with specific amino acids. In some embodiments of any one of the aspects described herein, machine learning, genetic algorithms, or principle component analysis (PCA) can be used for comparing spectra and reference spectra.

Detection of Spectral Properties

Embodiments of the various aspects described herein include detecting or measuring spectral properties of a probe conjugated to an amino acid. Methods and systems for measuring/detecting spectral properties of molecule are well known in the art. Exemplary such methods include, but are not limited to, confocal laser (scanning) microscopy, widefield microscopy, near-field microscopy, fluorescence lifetime imaging microscopy, fluorescence correlation spectroscopy, fluorescence intensity distribution analysis, measuring brightness changes induced by quenching/dequenching of fluorescence, or fluorescence energy transfer.

In some embodiments of any one of the aspects described herein, the detecting the spectral properties of a conjugated probe comprises optical detection. Exemplary optical detection systems include, but are not limited to, a charge-coupled device (CCD), electron multiplying CCD (EMCCD), near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, total internal reflection fluorescence (TIRF) microscopy, super-resolution fluorescence microscopy, single-molecule localization microscopy, and single-molecule spectroscopy.

In some embodiments of any one of the aspects described herein, the method comprises detection of laser-activated fluorescence using a microscope equipped with a camera, sometimes referred to as high-efficiency photon detection system. Suitable photon detection systems include, but are not limited to, photodiodes and intensified CCD cameras.

It is noted that different techniques known in the art can be used to detect spectral properties of different conjugated probes at spatially resolved locations. For example, super resolution microscopy can be used to detect one or more spectral properties of a conjugated probe conjugated at a particular location within a sample. In some embodiments of any one of the aspects described herein, the methods described herein use stochastic optical reconstruction microscopy (STORM).

In some embodiments of any one of the aspects described herein, the detecting the spectral properties of a conjugated probe includes ultrasensitive detection systems that are able to repeatedly detect signals from precisely the same coordinates in a sample, thereby assigning the detected spectral information to a unique molecule, e.g., a polypeptide.

Embodiments of the various aspects described herein include detecting or measuring one or more spectral properties of a probe conjugated with an amino acid. In some embodiments of any one of the aspects described herein, detecting or measuring one or more spectral properties of a probe conjugated with an amino acid comprises measuring or detecting fluorescence of the conjugated probe.

In some embodiments, the method comprises detecting/identifying one or more spectral properties for each probe conjugated to the terminal amino acid of each of the plurality of polypeptides at spatially resolved locations in a sample comprising the plurality of polypeptides.

In an embodiment, detection of one or more spectral properties comprises detecting fluorescence of the conjugated probe. In an embodiment, detecting one or more spectral properties of the conjugated probe comprises detecting fluorescence emission intensity, polarity/anisotropy or lifetime. In another embodiment, detecting the emission intensity, polarity/anisotropy or lifetime is at a single wavelength. In a further embodiment, detecting the emission intensity, polarity/anisotropy or lifetime is at a plurality of wavelengths.

In some embodiments of any one of the aspects described herein, detection of one or more spectral properties of the conjugated probe comprises super resolution microscopy. In some further embodiments, the super resolution microscopy comprises stochastic optical reconstruction microscopy (STORM).

Polypeptides

The amino acid to be identified/detected can be part of a polypeptide. When the amino acid is part of a polypeptide, the amino acid can be present anywhere in the polypeptide. For example, the amino acid can be at the N-terminus of the polypeptide. In some other non-limiting example, the amino acid can be at the C-terminus of the polypeptide. In yet some other non-limiting example, the amino acid can be at an internal, i.e., a non-terminal positon of the polypeptide. It is noted that the terminal amino acid may be modified or derivatized prior to conjugating with the probe.

In some embodiments, the method further comprises immobilizing the polypeptide on a substrate prior to conjugation with a probe. For example, the C-terminal end of the polypeptide can be conjugated to a substrate, optionally through a linker.

Sequencing

The methods for detecting/identifying a terminal amino acid of polypeptide can be used for sequencing, at least a part of, a polypeptide. Generally, the method comprises: (a) conjugating a probe to a terminal amino acid, e.g., N-terminal amino acid, of the polypeptide wherein the probe comprises a dipyrromethane-BF2 derivative that exhibits different fluorescent spectral properties when conjugated to different terminal amino acids; (b) detecting one or more fluorescent spectral properties of the probe conjugated to the terminal amino acid by detecting fluorescence of the probe bound to the terminal amino acid of the polypeptide; (c) identifying the corresponding terminal amino acid of the polypeptide by comparing the fluorescent spectral properties of the probe to a plurality of reference fluorescent spectral properties, wherein each reference fluorescent spectral property is representative of the probe conjugated to a different terminal amino acid; (d) cleaving the terminal amino acid of the polypeptide; and (e) sequentially repeating steps (a) to (d) one or more times to determine the sequence of at least a portion of the polypeptide.

Methods for cleaving a terminal amino acid while leaving the remainder of the polypeptide are known in the art. For example, the N-terminal amino acid of a polypeptide can be cleaved using Edman, or related, chemical degradation. Alternatively, the N-terminal amino acid of a polypeptide can be cleaved enzymatically with a protease, such as an aminopeptidase. Similarly, the C-terminal amino acid of a polypeptide can be cleaved enzymatically with a protease such as a carboxypeptidase.

In some embodiments, the method described herein for sequencing a polypeptide comprises comparing the sequence obtained for the polypeptide to a reference protein sequence database. Without wishing to be bound by a theory, small fragments comprising 10-20, or fewer, sequenced amino acid residues, consecutive or with gaps, can be useful for detecting the identity of a polypeptide in a sample.

The methods and probes described herein are useful for labeling and sequencing a plurality of polypeptides in parallel. Accordingly, in another aspect, provided herein is a multiplex method of sequencing a plurality of polypeptides. The method comprises: comprising: (a) conjugating plurality of probes to a terminal amino acid of each of the plurality of polypeptides, wherein each probe in the plurality of the probes exhibits different fluorescent spectral properties when conjugated to different terminal amino acids; (b) detecting one or more fluorescent spectral properties of each probe conjugated to the terminal amino acid of each of the plurality of polypeptides; (c) identifying the corresponding terminal amino acid of each of the plurality of the polypeptides by comparing the fluorescent spectral properties of the probe to a plurality of reference fluorescent spectral properties, wherein each reference fluorescent spectral property is representative of the probe conjugated to a different terminal amino acid; (d) cleaving the terminal amino acid of each of the plurality of polypeptides; and (e) sequentially repeating steps (a) to (d) one or more times to determine the sequence of at least a portion of each of the plurality of polypeptides.

The methods described herein can be used to sequence a polypeptide in situ. For example, the method described herein can be used to sequence a polypeptide present in or on a biological sample, such as a tissue, cell, lipid membrane or intracellular organelle, or sample thereof Sample The amino acid or polypeptide can be present in a sample. As used herein the term "sample" includes any material that contains the amino acid to be detected/identified or the polypeptide comprising said amino acid. The sample can be a biological sample, such as animal or plant tissues, biopsies, organs, cells, membrane vesicles, plasma membranes, organelles, cell extracts, secretions, urine or mucous, tissue extracts or other biological specimens both natural or synthetic in origin. The term sample also includes single cells, organelles or intracellular materials isolated from a biological specimen, or viruses, bacteria, fungus or isolates therefrom. The sample can also be an environmental sample, such as a water sample or soil sample, or a sample of any artificial or natural material that contains the amino acid to be detected/identified or the polypeptide comprising said amino acid.

Kits

In another aspect, the disclosure provides a kit comprising one or more compounds described herein. Accordingly, in some embodiments, the kit comprises a compound of Formula (I). In some embodiments, the kit comprises a compound of Formula (II). In some embodiments, the kit comprises a compound of Formula (I) and a compound of Formula (II).

In certain embodiments, such kits are intended for therapeutic and/or diagnostic applications. In certain embodiments, such kits are intended for research use. The kit can be useful in the methods described herein.

A kit described herein can further comprise one or more reagents/components for conjugating a compound Formula (I) with an amino acid, a peptide or a polypeptide.

In some embodiments of any of the aspects, the kit further comprises instructions for use.

In some embodiments of any one of the aspects described herein, the kit further comprises one or more reagents for conjugating a compound Formula (I) with an amino acid.

In some embodiments of any of the aspects, the kit further comprises reagents for isolating, or at least partially isolating, amino acids, peptides or polypeptides from a sample, e.g., a biological sample.

The components described herein can be provided singularly or in any combination as a kit. Such a kit includes the components described herein and packaging materials thereof. In addition, a kit optionally comprises informational material. The informational material can be descriptive, instructional, marketing or other material that relates to the methods described herein and/or the use of the aggregates for the methods described herein. For example, the informational material can describe methods for using the kits provided herein to perform an assay for detection of an amino acid, a peptide or a polypeptide. The kit can also include an empty container and/or a delivery device, e.g., which can be used to deliver or prepare a test sample to a test container.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments, the kit can contain separate containers, dividers or compartments for each component and informational material. For example, each different component can be contained in a bottle, vial, or syringe, and the informational material can be contained in a plastic sleeve or packet. In other embodiments, the separate elements of the kit are contained within a single, undivided container. For example, a collection of the magnetic particles is contained in a bottle, vial or syringe that has attached thereto the informational material in the form of a label.

In some embodiments the kit includes a carrier for organizing and protecting the components in the kit during transport or storage. The carrier can be in any form including a bag, a box or a case, including handles, straps and wheels for convenient movement or storage.

Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%, ±1.5%, ±2%, ±2.5%, ±3%, ±3.5%, ±4%, ±4.5%, or ±5%.

The singular terms "a," "an," and "the" include plural referents unless context clearly indicates otherwise. Similarly, the word "of" is intended to include "and" unless the context clearly indicates otherwise.

As used herein the terms "comprising" or "comprises" means "including" or "includes" and are used in reference to compositions, methods, systems, and respective component (s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The singular terms "a," "an," and "the" include plural referents unless context clearly indicates otherwise. Similarly, the word "of" is intended to include "and" unless the context clearly indicates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The abbreviation, "e.g." is derived from the Latin exempli gratia, and is used herein to indicate a non-limiting example. Thus, the abbreviation "e.g." is synonymous with the term "for example."

The terms "significantly different than,", "statistically significant," and similar phrases refer to comparisons between data or other measurements, wherein the differences between two compared data or other measurements are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

The term "statistically significant" or "significantly" refers to statistical significance and generally means a two standard deviation (2SD) or greater difference.

As used herein, "polypeptide" refers to two or more amino acids linked together by a peptide bond. The term "polypeptide" includes proteins, or protein digests, that have a C-terminal end and an N-terminal end as generally known in the art and may be synthetic in origin or naturally occurring. As used herein "at least a portion of the polypeptide" refers to 2 or more amino acids of the polypeptide. Optionally, a portion of the polypeptide includes at least: 5, 10, 20, 30, or 50 amino acids, either consecutive or with gaps, of the complete amino acid sequence of the polypeptide, or the full amino acid sequence of the polypeptide.

The phrase "N-terminal amino acid" refers to an amino acid that has a free amine group and is only linked to one other amino acid by a peptide amide bond in the polypeptide. Optionally, the "N-terminal amino acid" may be an "N-terminal amino acid derivative". As used herein, an "N-terminal amino acid derivative" refers to a N-terminal amino acid residue that has been chemically modified, for example by an Edman reagent or other chemical in vitro or inside a cell via a natural post-translational modification (e.g. phosphorylation) mechanism.

The phrase "C-terminal amino acid" refers to an amino acid that has a free carboxylic group and is only linked to one other amino acid by a peptide amide bond in the polypeptide. Optionally, the "C-terminal amino acid" may be an "C-terminal amino acid derivative". As used herein, an "C-terminal amino acid derivative" refers to a C-terminal amino acid residue that has been chemically modified in vitro or inside a cell via a natural post-translational modification (e.g. phosphorylation) mechanism.

As used herein, "sequencing a polypeptide" refers to determining the amino acid sequence of a polypeptide. The term also refers to determining the sequence of a segment of a polypeptide or determining partial sequence information for a polypeptide.

As used herein, the term "alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. "Branched" refers to an alkyl group in which a lower alkyl group, such as methyl, ethyl or propyl, is attached to a linear alkyl chain. Exemplary alkyl groups include methyl, ethyl, propyl, i-propyl, n-butyl, t-butyl, n-pentyl, hexyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

A "heteroalkyl" group substitutes any one of the carbons of the alkyl group with a heteroatom having the appropriate number of hydrogen atoms attached (e.g., a $CH_2$ group to an NH group or an O group). The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. In some embodiments, up to two heteroatoms are consecutive, such as, by way of example, —$CH_2$—NH—O$CH_3$ and —$CH_2$—O—Si($CH_3$)$_3$ As used herein, the term "alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

As used herein, the term "alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

As used herein, the term "cycloalkyl" refers to a nonaromatic mono- or multicyclic ring system of about 3 to about 12 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl and cycloheptyl. Useful multicyclic cycloalkyl rings include adamantyl, octahydronaphthyl, decalin, camphor, camphane, and noradamantyl.

"Heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Aryl" refers to an aromatic carbocyclic radical containing about 3 to about 13 carbon atoms. The aryl group can be optionally substituted with one or more aryl group substituents, which can be the same or different, where "aryl group substituent" includes alkyl, perhaloalkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, rylthio, alkylthio, alkylene and —NRR', where R and R' are each independently hydrogen, alkyl, perhaloalkyl, aryl and aralkyl. Exemplary aryl groups include substituted or unsubstituted phenyl and substituted or unsubstituted naphthyl.

"Heteroaryl" refers to an aromatic 3-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively.

Exemplary aryl and heteroaryls include, but are not limited to, phenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, naphthyl, anthracenyl, azulenyl, fluorenyl, indanyl, indenyl, naphthyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application.

The term "haloalkyl" as used herein refers to alkyl and alkoxy structures structure with at least one substituent of fluorine, chorine, bromine or iodine, or with combinations thereof. In embodiments, where more than one halogen is included in the group, the halogens are the same or they are different. The terms "fluoroalkyl" and "fluoroalkoxy" include haloalkyl and haloalkoxy groups, respectively, in which the halo is fluorine. Exemplary halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl ($CF_3$), perfluoroethyl, 2,2,2-trifluoroethyl, 2,2,2-trifluoro-1,1-dichloroethyl, and the like).

The term "perhalo alkyl" means, unless otherwise stated, alkyl substituted with (2n+1) halogen atoms, where n is the total number of carbon atoms in the alkyl group. For example, the term "perhalo($C_1$-$C_4$)alkyl" or "$C_1$-$C_4$perhaloalkyl" includes trifluoromethyl, pentachloroethyl, 1,1,1-trifluoro-2-bromo-2-chloroethyl, and the like.

The terms "fluoroalkyl" and "fluoroalkoxy" include haloalkyl and haloalkoxy groups, respectively, in which the halo is fluorine. Exemplary halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl ($CF_3$), perfluoroethyl, 2,2,2-trifluoroethyl, 2,2,2-trifluoro-1,1-dichloroethyl, and the like).

As used herein, the term "amino" means —$NH_2$. The term "alkylamino" means a nitrogen moiety having one straight or branched unsaturated aliphatic, cyclyl, or heterocyclyl radicals attached to the nitrogen, e.g., —NH(alkyl). The term "dialkylamino" means a nitrogen moiety having at two straight or branched unsaturated aliphatic, cyclyl, or heterocyclyl radicals attached to the nitrogen, e.g., —N(alkyl)(alkyl). The term "alkylamino" includes "alkenylamino," "alkynylamino," "cyclylamino," and "heterocyclylamino." The term "arylamino" means a nitrogen moiety having at least one aryl radical attached to the nitrogen. For example, —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like. Exemplary alkylamino includes, but is not limited to, NH($C_1$-$C_{10}$alkyl), such as —$NHCH_3$, —$NHCH_2CH_3$, —$NHCH_2CH_2CH_3$, and —$NHCH(CH_3)_2$. Exemplary dialkylamino includes, but is not limited to, —N($C_1$-$C_{10}$alkyl)$_2$, such as N($CH_3$)$_2$, —N($CH_2CH_3$)$_2$, —N($CH_2CH_2CH_3$)$_2$, and —N($CH(CH_3)_2$)$_2$.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The terms "hydroxy" and "hydroxyl" mean the radical —OH.

The terms "alkoxyl" or "alkoxy" as used herein refers to an alkyl group, as defined above, having an oxygen radical attached thereto, and can be represented by one of —O-alkyl, —O-alkenyl, and —O-alkynyl. Aroxy can be represented by —O-aryl or O-heteroaryl, wherein aryl and heteroaryl are as defined herein. The alkoxy and aroxy groups can be substituted as described above for alkyl. Exemplary alkoxy groups include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

As used herein, the term "carbonyl" means the radical C(O)—. It is noted that the carbonyl radical can be further substituted with a variety of substituents to form different carbonyl groups including acids, acid halides, amides, esters, ketones, and the like.

As used herein, the term "oxo" means double bonded oxygen, i.e., =O.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. As used herein, a carboxy group includes —COOH, i.e., carboxyl group.

The term "ester" refers to a chemical moiety with formula —C(=O)OR, where R is selected from the group consisting of alkyl, cycloalkyl, aryl, heteroaryl and heterocycloalkyl.

The term "cyano" means the radical —CN.

The term "nitro" means the radical —$NO_2$.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —$NR^N$—, —$N^+(O^-)$=, —O—, —S— or —S(O)$_2$—, —OS(O)$_2$—, and —SS—, wherein $R^N$ is H or a further substituent.

The terms "alkylthio" and "thioalkoxy" refer to an alkoxy group, as defined above, where the oxygen atom is replaced with a sulfur. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

"Aroyl" means an aryl-CO— group, wherein aryl is as previously described. Exemplary aroyl groups include benzoyl and 1- and 2-naphthoyl.

"Arylthio" refers to an aryl-S— group, wherein the aryl group is as previously described. Exemplary arylthio groups include phenylthio and naphthylthio.

"Aralkyl" refers to an aryl-alkyl- group, wherein aryl and alkyl are as previously described. Exemplary aralkyl groups include benzyl, phenylethyl and naphthylmethyl.

"Aralkyloxy" refers to an aralkyl-O— group, wherein the aralkyl group is as previously described. An exemplary aralkyloxy group is benzyloxy.

"Aralkylthio" refers to an aralkyl-S— group, wherein the aralkyl group is as previously described. An exemplary aralkylthio group is benzylthio.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

"Acyloxy" refers to an acyl-O— group, wherein acyl is as previously described. "Acylamino" refers to an acyl-NH— group, wherein acyl is as previously described. "Aroylamino" refers to an aroyl-NH— group, wherein aroyl is as previously described.

The term "optionally substituted" means that the specified group or moiety is unsubstituted or is substituted with one or more (typically 1, 2, 3, 4, 5 or 6 substituents) independently selected from the group of substituents listed below in the definition for "substituents" or otherwise specified. The term "substituents" refers to a group "substituted" on a substituted group at any atom of the substituted group. Suitable substituents include, without limitation, halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

For example, any alkyl, alkenyl, cycloalkyl, heterocyclyl, heteroaryl or aryl is optionally substituted with 1, 2, 3, 4 or 5 groups selected from OH, CN, —SC(O)Ph, oxo (=O), SH, $SO_2NH_2$, $SO_2(C_1$-$C_4)$alkyl, $SO_2NH(C_1$-$C_4)$alkyl, halogen, carbonyl, thiol, cyano, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$ alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)-alkyl, C(O)—alkyl, alkylcarbonylaminyl, $CH_2$—[CH(OH)]$_m$—$(CH_2)_p$—OH, $CH_2$—[CH(OH)]$_m$ $(CH_2)_p$—$NH_2$ or $CH_2$-aryl-alkoxy; "m" and "p" are independently 1, 2, 3, 4, 5 or 6.

In some embodiments, an optionally substituted group is substituted with 1 substituent. In some other embodiments, an optionally substituted group is substituted with 2 independently selected substituents, which can be same or different. In some other embodiments, an optionally substituted group is substituted with 3 independently selected substituents, which can be same, different or any combination of same and different. In still some other embodiments, an optionally substituted group is substituted with 4 independently selected substituents, which can be same, different or any combination of same and different. In yet some other embodiments, an optionally substituted group is substituted with 5 independently selected substituents, which can be same, different or any combination of same and different.

An "isocyanato" group refers to a NCO group.
A "thiocyanato" group refers to a CNS group.
An "isothiocyanato" group refers to a NCS group.
"Alkoyloxy" refers to a RC(=O)O— group.
"Alkoyl" refers to a RC(=O)— group.

All structures of any of the compounds are provided herein for illustrative purpose and disclose a particular isomer. However, one of ordinary skill in the art will recognize all possible isomers of the structures of any of the compounds described herein. Therefore, other isomers such as enantiomers of any of Formula (I) and (II) are considered to fall within the scope of the invention. As used herein, the term "isomer" refers to a compound having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. The designations "R" and "S" are used to denote the absolute configuration of the molecule about its chiral center. The designations may appear as a prefix or as a suffix; they may or may not be separated from the isomer by a hyphen; they may or may not be hyphenated; and they may or may not be surrounded by parentheses. The designations "(+)" and "(−)" are employed to designate the sign of rotation of plane-polarized light by the compound, with (−) meaning that the compound is levorotatory (rotates to the left). A compound prefixed with (+) is dextrorotatory (rotates to the right). Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

In various embodiments, compounds of Formula (I) or (II) include enantiomers, derivatives, prodrugs, and pharmaceutically acceptable salts thereof.

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Aspects of the present technology can be defined in any of the following numbered embodiments:

Embodiment 1: A method of identifying an amino acid, the method comprising: (a) conjugating a probe to an amino acid, wherein the probe comprises a dipyrromethane-BF2 derivative that exhibits different fluorescent spectral properties when conjugated to the amino acid; (b) detecting one or more fluorescent spectral properties of the probe conjugated to the amino acid; and (c) identifying the amino acid by comparing the fluorescent spectral properties of the probe to a plurality of reference fluorescent spectral properties, wherein each reference fluorescent spectral property is representative of the probe conjugated to a different amino acid.

Embodiment 2: A multiplex method of identifying a plurality of amino acids, the method comprising: (a) conjugating a plurality of probes to an amino, a carboxylic, a hydroxyl or a thiol group of a plurality of amino acids, wherein each probe in the plurality of the probes comprises a dipyrromethane-BF2 derivative that exhibits different fluorescent spectral properties when conjugated to different amino acids; (b) detecting one or more fluorescent spectral properties for each probe conjugated to the plurality of the amino acids; and (c) identifying the amino acid by comparing the plurality of the fluorescent spectral properties of the probes to a plurality of reference fluorescent spectral properties, wherein each reference fluorescent spectral property is representative of the probe conjugated to a different amino acid.

Embodiment 3: The method of Embodiment 2 or Embodiment 3, wherein the probe is covalently conjugated to the amino acid.

Embodiment 4: The method of any one of Embodiments 1-3, wherein the probe is conjugate to an amino, a carboxylic, a hydroxyl or a thiol group of the amino acid.

Embodiment 5: The method of any one of Embodiments 1-4, wherein the probe is conjugated to an amino group of the amino acid.

Embodiment 6: The method of any one of Embodiments 1-4, wherein the probe is conjugated to a carboxylic group of the amino acid.

Embodiment 7: The method of any one of Embodiment 1-6, wherein the amino acid is in a sample.

Embodiment 8: The method of any one of Embodiments 1-7, wherein the amino acid is in a polypeptide.

Embodiment 9: The method of Embodiment 8, wherein the amino acid is at an N-terminal of the polypeptide.

Embodiment 10: The method of Embodiment 8, wherein the amino acid is at a C-terminal of the polypeptide.

Embodiment 11: A method of sequencing a polypeptide comprising: (a) conjugating a probe to a terminal amino acid of the polypeptide wherein the probe comprises a dipyrromethane-BF2 derivative that exhibits different fluorescent spectral properties when conjugated to different terminal amino acids; (b) detecting one or more fluorescent spectral properties of the probe conjugated to the terminal amino acid by detecting fluorescence of the probe bound to the terminal amino acid of the polypeptide; (c) identifying the corresponding terminal amino acid of the polypeptide by comparing the fluorescent spectral properties of the probe to a plurality of reference fluorescent spectral properties, wherein each reference fluorescent spectral property is representative of the probe conjugated to a different terminal amino acid; (d) cleaving the terminal amino acid of the polypeptide; and (e) sequentially repeating steps (a) to (d) one or more times to determine the sequence of at least a portion of the polypeptide.

Embodiment 12: A multiplex method of sequencing a plurality of polypeptides comprising: (a) conjugating plurality of probes to a terminal amino acid of each of the plurality of polypeptides, wherein each probe in the plurality of the probes comprises a dipyrromethane-BF2 derivative that exhibits different fluorescent spectral properties when conjugated to different terminal amino acids; (b) detecting one or more fluorescent spectral properties of each probe conjugated to the terminal amino acid of each of the plurality of polypeptides; (c) identifying the corresponding terminal amino acid of each of the plurality of the polypeptides by comparing the fluorescent spectral properties of the probe to a plurality of reference fluorescent spectral properties, wherein each reference fluorescent spectral property is representative of the probe conjugated to a different terminal amino acid; (d) cleaving the terminal amino acid of each of the plurality of polypeptides; and (e) sequentially repeating steps (a) to (d) one or more times to determine the sequence of at least a portion of each of the plurality of polypeptides.

Embodiment 13: The method of Embodiment 2 or 12, wherein the probes in the plurality of the probes are the same.

Embodiment 14: The method of Embodiment 2 or 12, wherein at least two probes in the plurality of the probes are different.

Embodiment 15: The method of any one of Embodiments 11-14, wherein the terminal amino acid is at an N-terminal of the polypeptide.

Embodiment 16: The method of any one of Embodiments 11-14, wherein the terminal amino acid is at a C-terminal of the polypeptide.

Embodiment 17: The method any one of Embodiments 11-16, wherein the step of cleaving the terminal amino acid comprises enzymatic cleavage.

Embodiment 18: The method of any one of Embodiments 11-16, wherein the step of cleaving the terminal amino acid comprises chemical cleavage.

Embodiment 19: The method of any one of Embodiments 11-15, wherein polypeptide is in a sample.

Embodiment 20: The method of Embodiment 19, wherein the method comprises detecting one or more spectral properties for each probe conjugated to the terminal amino acid of each of the plurality of polypeptides at spatially resolved locations in the sample comprising the plurality of polypeptides.

Embodiment 21: The method of any one of Embodiments 7, 19 or 20, wherein the sample is a biological sample.

Embodiment 22: The method of Embodiment 21, wherein the biological sample is a biological fluid, a tissue, an organ, a cell.

Embodiment 23: The method of any one of Embodiments 1-22, wherein said detecting one or more spectral properties of the conjugated probe comprises super resolution microscopy.

Embodiment 24: The method of Embodiment 23, wherein the super resolution microscopy comprises stochastic optical reconstruction microscopy (STORM).

Embodiment 25: The method of any one of Embodiments 1-25, wherein detecting one or more spectral properties comprises detecting fluorescence of the conjugated probe.

Embodiment 26: The method of any one of Embodiments 1-26, wherein detecting one or more spectral properties of the conjugated probe comprises detecting fluorescence emission intensity, polarity/anisotropy or lifetime.

Embodiment 27: The method of Embodiment 26, wherein said detecting the emission intensity, polarity/anisotropy or lifetime is at a single wavelength.

Embodiment 28: The method of Embodiment 26, comprising said detecting the emission intensity, polarity/anisotropy or lifetime is at a plurality of wavelengths.

Embodiment 29: The method of any one of Embodiments 1-28, wherein the dipyrromethane-BF2 derivative comprises a labile or reactive group.

Embodiment 30: The method of any one of Embodiments 1-29, wherein the dipyrromethane-BF2 derivative comprises a 4,4-difluoro-4-bora-3a,4a-diaza-s-indacene derivative.

Embodiment 31: The method of Embodiment 30, wherein the probe is conjugated via position 8 (meso position) of the 4,4-difluoro-4-bora-3a,4a-diaza-s-indacene derivative.

Embodiment 32: The method of Embodiment 31, wherein the 4,4-difluoro-4-bora-3a,4a-diaza-s-indacene derivative comprises a labile or reactive group at position 8 (meso position).

Embodiment 33: The method of any one of Embodiments 1-30, wherein the probe is of Formula (I), wherein $R^1$, $R^2$, $R^3$, $R^4$, $R^5$, $R^6$, $R^7$ and $R^8$ are each independently selected from the group consisting of hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfonate, sulfinyl, sulfonyl, carbamoyl, isocyanato, thiocyanato, isothiocyanato, ureido, and a labile or leaving group, optionally at least one of $R^1$, $R^2$, $R^3$, $R^4$, $R^5$, $R^6$, $R^7$ and $R^8$ is a labile or leaving group, and any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

Embodiment 34: The method of Embodiment 33, wherein $R^8$ is a labile or leaving group.

Embodiment 35: The method of Embodiment 33 or 34, wherein $R^8$ is optionally substituted alkylthio, halogen, optionally substituted alkoxyl, hydxoryl, optionally substituted acyloxy, tosylate, triflate, mesylate, nitrile, azide, carbamate, disulfide, thioester, and diazonium.

Embodiment 36: The method of Embodiment 35, wherein $R^8$ is —$SR^{8S}$ or halogen, wherein $R^{8S}$ is optionally substituted alkyl, perhaloalkyl, optionally substituted alkenyl, optionally cycloalkyl, optionally substituted heterocyclyl, optionally substituted aryl or optionally substituted heteroaryl.

Embodiment 37: The method of Embodiment 36, wherein $R^{8S}$ is optionally substituted C1-C6alkyl, C1-C6perhaloalkyl optionally substituted $C_2$-$C_6$alkenyl, optionally substituted aryl or optionally substituted heteroaryl.

Embodiment 38: The method of Embodiment 37, wherein $R^{8S}$ is methyl, allyl, phenyl, 4-methoxyphenyl, 4-nitrophenyl, benzyl, or 4-methoxybenzyl, optionally, $R^{8S}$ is methyl.

Embodiment 39: The method of any one of Embodiments 33-38, wherein at least one of $R^1$, $R^2$, $R^3$, $R^5$, $R^6$ and $R^7$ is not H.

Embodiment 40: The method of any one of Embodiments 33-39, wherein at least one of $R^1$, $R^2$, $R^3$, $R^5$, $R^6$ and $R^7$ is an electron withdrawing group (EWG).

Embodiment 41: The method of any one of Embodiments 33-39, wherein at least one of $R^1$, $R^2$, $R^3$, $R^5$, $R^6$ and $R^7$ is an electron donating group (EDG).

Embodiment 42: The method of any one of Embodiments 33-41, wherein at least two of $R^1$, $R^2$ and $R^3$ are same.

Embodiment 43: The method of any one of Embodiments 33-41, wherein at least two of $R^1$, $R^2$ and $R^3$ are different.

Embodiment 44: The method of any one of Embodiments 33-43, wherein $R^1$ and $R^7$ are different, or $R^2$ and $R^6$ are different, or $R^3$ and $R^5$ are different.

Embodiment 45: The method of any one of Embodiments 33-43, wherein $R^1$ and $R^7$ are same, $R^2$ and $R^6$ are same, and $R^3$ and $R^5$ are same.

Embodiment 46: The method of any one of Embodiments 33-45, wherein $R^1$ is H or optionally substituted $C_1$-$C_6$alkyl.

Embodiment 47: The method of Embodiment 46, wherein $R^1$ is H or methyl.

Embodiment 48: The method of any one of Embodiments 33-47, wherein $R^2$ is H, halogen, optionally substituted $C_1$-$C_6$ alkyl, —C(O)H, or —$SO_3H$.

Embodiment 49: The method of Embodiment 48, wherein $R^2$ is H, Br, Cl, —C(O)H, or —$SO_3H$.

Embodiment 50: The method of any one of Embodiments 33-49, wherein $R^3$ is H, halogen, optionally substituted C1-C6alkyl, C1-C6perhaloalkyl optionally substituted $C_1$-$C_6$alkenyl, optionally substituted phenyl or optionally substituted napthelene.

Embodiment 51: The method of any one of Embodiments 33-50, wherein $R^3$ is H, Br, Cl, methyl, —CH=CH—$R^{9A}$, phenyl, bisphenyl (4phenylphenyl), napthelene, or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl, where $R^{9A}$ is optionally substituted aryl or heteroaryl.

Embodiment 52: The method of any one of Embodiments 33-51, wherein $R^3$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthelene.

Embodiment 53: The method of any one of Embodiments 33-51, wherein $R^3$ is H, methyl or —CH═CH—$R^{9A}$, where $R^{9A}$ is optionally substituted phenyl.

Embodiment 54: The method of Embodiment 53, wherein $R^{9A}$ is phenyl or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl.

Embodiment 55: The method of Embodiment 54, wherein $R^{9A}$ is 4-fluoropheyl, 4-trifluoromethylphenyl or 4-cyanophenyl.

Embodiment 56: The method of any one of Embodiments 33-55, wherein $R^5$ is H, halogen, optionally substituted C1-C6alkyl, C1-C6perhaloalkyl optionally substituted $C_1$-$C_6$alkenyl, optionally substituted phenyl or optionally substituted napthelene.

Embodiment 57: The method of any one of Embodiments 33-56, wherein $R^5$ is H, Br, Cl, methyl, —CH═CH—$R^{9B}$, phenyl, bisphenyl (4phenylphenyl), napthelene, or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl, where $R^{9B}$ is optionally substituted aryl or heteroaryl.

Embodiment 58: The method of any one of Embodiments 33-57, wherein $R^5$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthelene.

Embodiment 59: The method of any one of Embodiments 33-57, wherein $R^5$ is H, methyl or —CH═CH—$R^{9B}$, where $R^{9B}$ is optionally substituted phenyl.

Embodiment 60: The method of Embodiment 59, wherein $R^{9B}$ is phenyl or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl.

Embodiment 61: The method of Embodiment 60, wherein $R^{9B}$ is 4-fluoropheyl, 4-trifluoromethylphenyl or 4-cyanophenyl.

Embodiment 62: The method of any one of Embodiments 33-61, wherein $R^6$ is H, halogen, optionally substituted $C_1$-$C_6$ alkyl, —C(O)H, or —SO$_3$H.

Embodiment 63: The method of Embodiment 62, wherein $R^6$ is H, Br, Cl, —C(O)H, or —SO$_3$H.

Embodiment 64: The method of any one of Embodiments 33-63, wherein $R^7$ is H or optionally substituted $C_1$-$C_6$alkyl.

Embodiment 65: The method of Embodiment 64, wherein $R^7$ is H or methyl.

Embodiment 66: The method of any one of Embodiments 33-65, wherein $R^1$, $R^2$, $R^3$, $R^5$, $R^6$ and $R^7$ are H.

Embodiment 67: A compound of Formula (I), wherein: $R^1$, $R^2$, $R^3$, $R^4$, $R^5$, $R^6$, $R^7$ and $R^8$ are each independently selected from the group consisting of hydrogen, halogen, alkyl, perhaloalkyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfonate, sulfinyl, sulfonyl, carbamoyl, isocyanato, thiocyanato, isothiocyanato, ureido, and a labile or leaving group, optionally at least one of $R^1$, $R^2$, $R^3$, $R^4$, $R^5$, $R^6$, $R^7$ and $R^8$ is a labile or leaving group, and any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido; and optionally provided that: (i) when $R^{8S}$ is methyl then: (a) $R^1$, $R^2$, $R^3$, $R^5$, $R^6$ and $R^7$ are not H; (b) $R^1$, $R^2$, $R^6$ and $R^7$ are not H, and $R^3$ and $R^5$ are not methyl, ethyl or p-nitrophenyl; (c) $R^1$, $R^3$, $R^5$ and $R^7$ are not methyl, and $R^2$ and $R^6$ are not H; (d) $R^1$ and $R^7$ are not H, and $R^2$, $R^3$, $R^5$ and $R^6$ are not Cl or Br; (e) $R^1$, $R^3$, $R^5$, $R^6$ and $R^7$ are not H, and $R^2$ is not —C(O)H; (f) $R^1$ is not p-nitrophenyl, $R^2$, $R^6$ are not H, and $R^3$ and $R^5$ are not methyl; and (g) $R^1$, $R^2$, $R^5$, $R^6$ and $R^7$ are not H, and $R^3$ is not phenyl, p-nitrophenyl, p-iodophenyl, p-carboxylicphenyl or p-methoxyphenyl, and/or (ii) when $R^{8S}$ is allyl, ethyl, propyl, butyl, t-butyl, n-dodecyl, phenyl, 2,6-dimethylphenyl, p-methylphenyl, p-methoxyphenyl, p-nitrophenyl or benzyl (—CH$_2$PH) then $R^1$, $R^2$, $R^3$, $R^5$, $R^6$ and $R^7$ are not H, and/or (iii) when $R^8$ is Cl then: (a) $R^1$, $R^2$, $R^3$, $R^5$, $R^6$ and $R^7$ are not H; (b) $R^1$, $R^3$, $R^5$, $R^6$ and $R^7$ are not H, and $R^2$ is not Cl; (c) $R^1$, $R^3$, $R^5$ and $R^7$ are not H, and $R^2$ and $R^5$ are not Cl; (d) $R^1$, $R^5$ and $R^7$ are not H, and $R^2$, $R^3$ and $R^5$ are not Cl; and (e) $R^1$, $R^2$, $R^3$, $R^5$, $R^6$ and $R^7$ are not Cl.

Embodiment 68: The compound of Embodiment 67, wherein $R^8$ is a labile or leaving group.

Embodiment 69: The compound of Embodiment 67 or 68, wherein $R^8$ is optionally substituted alkylthio, halogen, optionally substituted alkoxyl, hydroxyl, optionally substituted acyloxy, tosylate, triflate, mesylate, nitrile, azide, carbamate, disulfide, thioester, and diazonium.

Embodiment 70: The compound of any one of Embodiments 67-69, wherein $R^8$ is —SR$^{8S}$ or halogen, wherein $R^{8S}$ is optionally substituted alkyl, perhaloalkyl, optionally substituted alkenyl, optionally cycloalkyl, optionally substituted heterocyclyl, optionally substituted aryl or optionally substituted heteroaryl.

Embodiment 71: The compound of Embodiment 71, wherein $R^{8S}$ is optionally substituted C1-C6alkyl, C1-C6perhaloalkyl optionally substituted $C_2$-$C_6$alkenyl, optionally substituted aryl or optionally substituted heteroaryl.

Embodiment 72: The compound of Embodiment 72, wherein $R^{8S}$ is methyl, allyl, phenyl, 4-methoxyphenyl, 4-nitrophenyl, benzyl, or 4-methoxybenzyl, optionally, $R^{8S}$ is methyl.

Embodiment 73: The compound of any one of Embodiments 67-72, wherein at least one of $R^1$, $R^2$, $R^3$, $R^5$, $R^6$ and $R^7$ is not H.

Embodiment 74: The compound of any one of Embodiments 67-73, wherein at least one of $R^1$, $R^2$, $R^3$, $R^5$, $R^6$ and $R^7$ is an electron withdrawing group (EWG).

Embodiment 75: The compound of any one of Embodiments 67-73, wherein at least one of $R^1$, $R^2$, $R^3$, $R^5$, $R^6$ and $R^7$ is an electron donating group (EDG).

Embodiment 76: The compound of any one of Embodiments 67-75, wherein at least two of $R^1$, $R^2$ and $R^3$ are same.

Embodiment 77: The compound of any one of Embodiments 67-75, wherein at least two of $R^1$, $R^2$ and $R^3$ are different.

Embodiment 78: The compound of any one of Embodiments 66-77, wherein $R^1$ and $R^7$ are different, or $R^2$ and $R^6$ are different, or $R^3$ and $R^5$ are different.

Embodiment 79: The compound of any one of Embodiments 67-78, wherein $R^1$ and $R^7$ are same, $R^2$ and $R^6$ are same, and $R^3$ and $R^5$ are same.

Embodiment 80: The compound of any one of Embodiments 67-79, wherein $R^1$ is H or optionally substituted $C_1$-$C_6$alkyl.

Embodiment 81: The compound of Embodiment 80, wherein $R^1$ is H or methyl.

Embodiment 82: The compound of any one of Embodiments 67-81, wherein $R^2$ is H, halogen, optionally substituted $C_1$-$C_6$ alkyl, —C(O)H, or —SO$_3$H.

Embodiment 83: The compound of Embodiment 82, wherein $R^2$ is H, Br, Cl, —C(O)H, or —SO$_3$H.

Embodiment 84: The compound of any one of Embodiments 67-83, wherein $R^3$ is H, halogen, optionally substituted C1-C6alkyl, C1-C6perhaloalkyl optionally substituted $C_1$-$C_6$alkenyl, optionally substituted phenyl or optionally substituted napthelene.

Embodiment 85: The compound of any one of Embodiments 67-84, wherein $R^3$ is H, Br, Cl, methyl, —CH=CH—$R^9$, phenyl, bisphenyl (4phenylphenyl), napthelene, or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl, where $R^9$ is optionally substituted aryl or heteroaryl.

Embodiment 86: The compound of any one of Embodiments 67-85, wherein $R^3$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthelene.

Embodiment 87: The compound of any one of Embodiments 67-86, wherein $R^3$ is H, methyl or —CH=CH—$R^{9A}$, where $R^9$ is optionally substituted phenyl.

Embodiment 88: The compound of Embodiment 87, wherein $R^{9A}$ is phenyl or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$halo a nitro, cyano, halogen, amino, alkylamino, dialkylamino, carboxyl, C1-C6alkyl, C1-C6perhaloalkyl $C_1$-$C_6$haloalkyl.

Embodiment 89: The compound of Embodiment 88, wherein $R^{9A}$ is 4-fluoropheyl, 4-trifluoromethylphenyl or 4-cyanophenyl.

Embodiment 90: The compound of any one of Embodiments 67-89, wherein $R^5$ is H, halogen, optionally substituted C1-C6alkyl, C1-C6perhaloalkyl optionally substituted $C_1$-$C_6$alkenyl, optionally substituted phenyl or optionally substituted napthelene.

Embodiment 91: The compound of any one of Embodiments 67-90, wherein $R^5$ is H, Br, Cl, methyl, —CH=CH—$R^{9B}$, phenyl, bisphenyl (4phenylphenyl), napthelene, or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$halo nitro, cyano, halogen, amino, alkylamino, dialkylamino, carboxyl, C1-C6alkyl, C1-C6perhaloalkyl $C_1$-$C_6$haloalkyl, where $R^{9B}$ is optionally substituted aryl or heteroaryl.

Embodiment 92: The compound of any one of Embodiments 67-91, wherein $R^5$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthelene.

Embodiment 93: The compound of any one of Embodiments 67-91, wherein $R^5$ is H, methyl or —CH=CH—$R^{9B}$, where $R^{9B}$ is optionally substituted phenyl.

Embodiment 94: The compound of Embodiment 93, wherein $R^{9B}$ is phenyl or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$halo a nitro, cyano, halogen, amino, alkylamino, dialkylamino, carboxyl, C1-C6alkyl, C1-C6perhaloalkyl $C_1$-$C_6$haloalkyl.

Embodiment 95: The compound of Embodiment 94, wherein $R^{9B}$ is 4-fluoropheyl, 4-trifluoromethylphenyl or 4-cyanophenyl.

Embodiment 96: The compound of any one of Embodiments 67-95, wherein $R^6$ is H, halogen, optionally substituted $C_1$-$C_6$ alkyl, —C(O)H, or —SO$_3$H.

Embodiment 97: The compound of Embodiment 96, wherein $R^6$ is H, Br, Cl, —C(O)H, or —SO$_3$H.

Embodiment 98: The compound of any one of Embodiments 67-97, wherein $R^7$ is H or optionally substituted $C_1$-$C_6$alkyl.

Embodiment 99: A compound of Formula (II), wherein $R^{21}$, $R^{22}$, $R^{23}$, $R^{24}$, $R^{25}$, $R^{26}$, $R^{27}$ and $R^{28}$ are each independently selected from the group consisting of hydrogen, halogen, alkyl, perhaloalkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cynao, nitro, thiol, alkylthio, sulfonate, sulfinyl, sulfonyl, carbamoyl, isocyanato, thiocyanato, isothiocyanato, ureido, and amino acid, optionally at least one of $R^{21}$, $R^{22}$, $R^{23}$, $R^{24}$, $R^{25}$, $R^{26}$, $R^{27}$ and $R^{28}$ is an amino acid, and any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

Embodiment 100: The compound of Embodiment 99, wherein $R^{28}$ is an amino acid.

Embodiment 101: The compound of any one of Embodiments 99-100, wherein at least one of $R^{21}$, $R^{22}$, $R^{23}$, $R^{25}$, $R^{26}$ and $R^{27}$ is not H.

Embodiment 102: The compound of any one of Embodiments 99-101, wherein at least one of $R^{21}$, $R^{22}$, $R^{23}$, $R^{25}$, $R^{26}$ and $R^{27}$ is an electron withdrawing group (EWG).

Embodiment 103: The compound of any one of Embodiments 99-102, wherein at least one of $R^{21}$, $R^{22}$, $R^{23}$, $R^{25}$, $R^{26}$ and $R^{27}$ is an electron donating group (EDG).

Embodiment 104: The compound of any one of Embodiments 99-103, wherein at least two of $R^{21}$, $R^{22}$ and $R^{23}$ are same.

Embodiment 105: The compound of any one of Embodiments 99-103, wherein at least two of $R^{21}$, $R^{22}$ and $R^{23}$ are different.

Embodiment 106: The compound of any one of Embodiments 99-105, wherein $R^{21}$ and $R^{27}$ are different, or $R^{22}$ and $R^{26}$ are different, or $R^{23}$ and $R^{25}$ are different.

Embodiment 107: The compound of any one of Embodiments 99-105, wherein $R^{21}$ and $R^{27}$ are same, $R^{22}$ and $R^{26}$ are same, and $R^{23}$ and $R^{25}$ are same.

Embodiment 108: The compound of any one of Embodiments 99-107, wherein $R^{21}$ is H or optionally substituted $C_1$-$C_6$alkyl.

Embodiment 109: The compound of Embodiment 108, wherein $R^{21}$ is H or methyl.

Embodiment 110: The compound of any one of Embodiments 99-109, wherein $R^{22}$ is H, halogen, optionally substituted $C_1$-$C_6$ alkyl, —C(O)H, or —SO$_3$H.

Embodiment 111: The compound of Embodiment 110, wherein $R^{22}$ is H, Br, Cl, —C(O)H, or —SO$_3$H.

Embodiment 112: The compound of any one of Embodiments 99-111, wherein $R^{23}$ is H, halogen, optionally substituted C1-C6alkyl, C1-C6perhaloalkyl optionally substituted $C_1$-$C_6$alkenyl, optionally substituted phenyl or optionally substituted napthelene.

Embodiment 113: The compound of any one of Embodiments 99-113, wherein $R^{23}$ is H, Br, Cl, methyl, —CH=CH—$R^{29A}$, phenyl, bisphenyl (4phenylphenyl), napthelene, or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloalkyl, where $R^{29A}$ is optionally substituted aryl or heteroaryl.

Embodiment 114: The compound of any one of Embodiments 99-113, wherein $R^{23}$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylpehnyl, 2-ethylphenyl, 2,4,6-trimethylphenyl, bisphenyl or napthelene.

Embodiment 115: The compound of any one of Embodiments 99-113, wherein $R^{23}$ is H, methyl or —CH=CH—$R^{29A}$, where $R^{29A}$ is optionally substituted phenyl.

Embodiment 116: The compound of Embodiment 115, wherein $R^{29A}$ is phenyl or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloa nitro, cyano, halogen, amino, alkylamino, dialkylamino, carboxyl, C1-C6alkyl, C1-C6perhaloalkyl $C_1$-$C_6$haloalkyl.

Embodiment 117: The compound of Embodiment 116, wherein $R^{29A}$ is 4-fluoropheyl, 4-trifluoromethylphenyl or 4-cyanophenyl.

Embodiment 118: The compound of any one of Embodiments 99-117, wherein $R^{25}$ is H, halogen, optionally substituted C1-C6alkyl, C1-C6perhaloalkyl optionally substituted $C_1$-$C_6$alkenyl, optionally substituted phenyl or optionally substituted napthelene.

Embodiment 119: The compound of any one of Embodiments 99-118, wherein $R^{25}$ is H, Br, Cl, methyl, —CH=CH—$R^{29B}$, phenyl, bisphenyl (4phenylphenyl), napthelene, or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloa nitro, cyano, halogen, amino, alkylamino, dialkylamino, carboxyl, C1-C6alkyl, C1-C6perhaloalkyl $C_1$-$C_6$haloalkyl, where $R^{29B}$ is optionally substituted aryl or heteroaryl.

Embodiment 120: The compound of any one of Embodiments 99-119, wherein $R^{25}$ is H, methyl, phenyl, 4-nitrophenyl, 4-cyanophenyl, 2-trifluoromethylphenyl, 3-trifluoromethylphenyl, 4-trifluoromethylphenyl, 2-methylphenyl, 3-methylphenyl, 4-methylphenyl, 2-ethylphenyl, 2,4,6-trimethylphenyl, bisphenyl or napthelene.

Embodiment 121: The compound of any one of Embodiments 99-119, wherein $R^{25}$ is H, methyl or —CH=CH—$R^{29B}$, where $R^{29B}$ is optionally substituted phenyl.

Embodiment 122: The compound of Embodiment 121, wherein $R^{29B}$ is phenyl or phenyl substituted with a substituent selected from the group consisting of nitro, cyano, halogen, amino, alkylamino, dialkylamino, carboxyl, C1-C6alkyl, C1-C6perhaloalkyl $C_1$-$C_6$haloa nitro, cyano, halogen, amino, alkylamino, dialkylamino, carboxyl, C1-C6alkyl, C1-C6perhaloalkyl $C_1$-$C_6$haloalkyl.

Embodiment 123: The compound of Embodiment 122, wherein $R^{29B}$ is 4-fluoropheyl, 4-trifluoromethylphenyl or 4-cyanophenyl.

Embodiment 124: The compound of any one of Embodiments 99-123, wherein $R^{26}$ is H, halogen, optionally substituted $C_1$-$C_6$ alkyl, —C(O)H, or —SO$_3$H.

Embodiment 125: The compound of Embodiment 124, wherein $R^{26}$ is H, Br, Cl, —C(O)H, or —SO$_3$H.

Embodiment 126: The compound of any one of Embodiments 99-125, wherein $R^{27}$ is H or optionally substituted $C_1$-$C_6$alkyl.

Embodiment 127: The compound of Embodiment 126, wherein $R^7$ is H or methyl.

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims. The invention is further illustrated by the following examples, which should not be construed as further limiting.

EXAMPLES

The following examples illustrate embodiments of the invention and are not intended to limit the scope of the invention.

Example 1: Synthesis of Exemplary Compounds BOPIDYs

Figure 6:
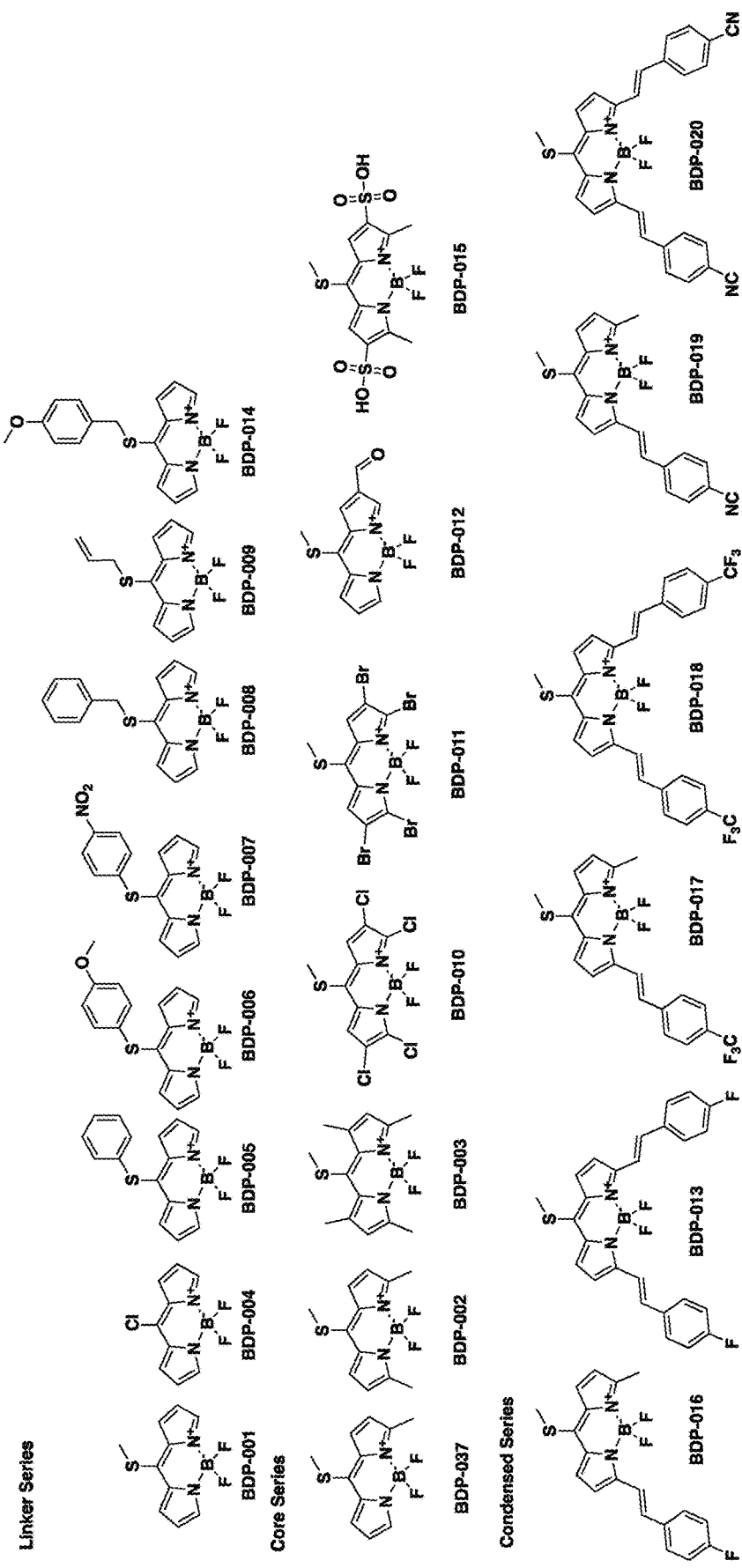

In one aspect, the inventors have developed the use of boron-dipyrromethane dyes (BODIPY) (FIG. 1) that can be directly conjugated to N-terminal amino acids. This conjugation influences the photophysical properties of the dye which in turn leads to different spectral signals depending on the amino acid. As outline in (FIG. 6), the BODIPY dye can differentiate nearly every amino acid, by fluorescent emission in this example.

Figure 7:
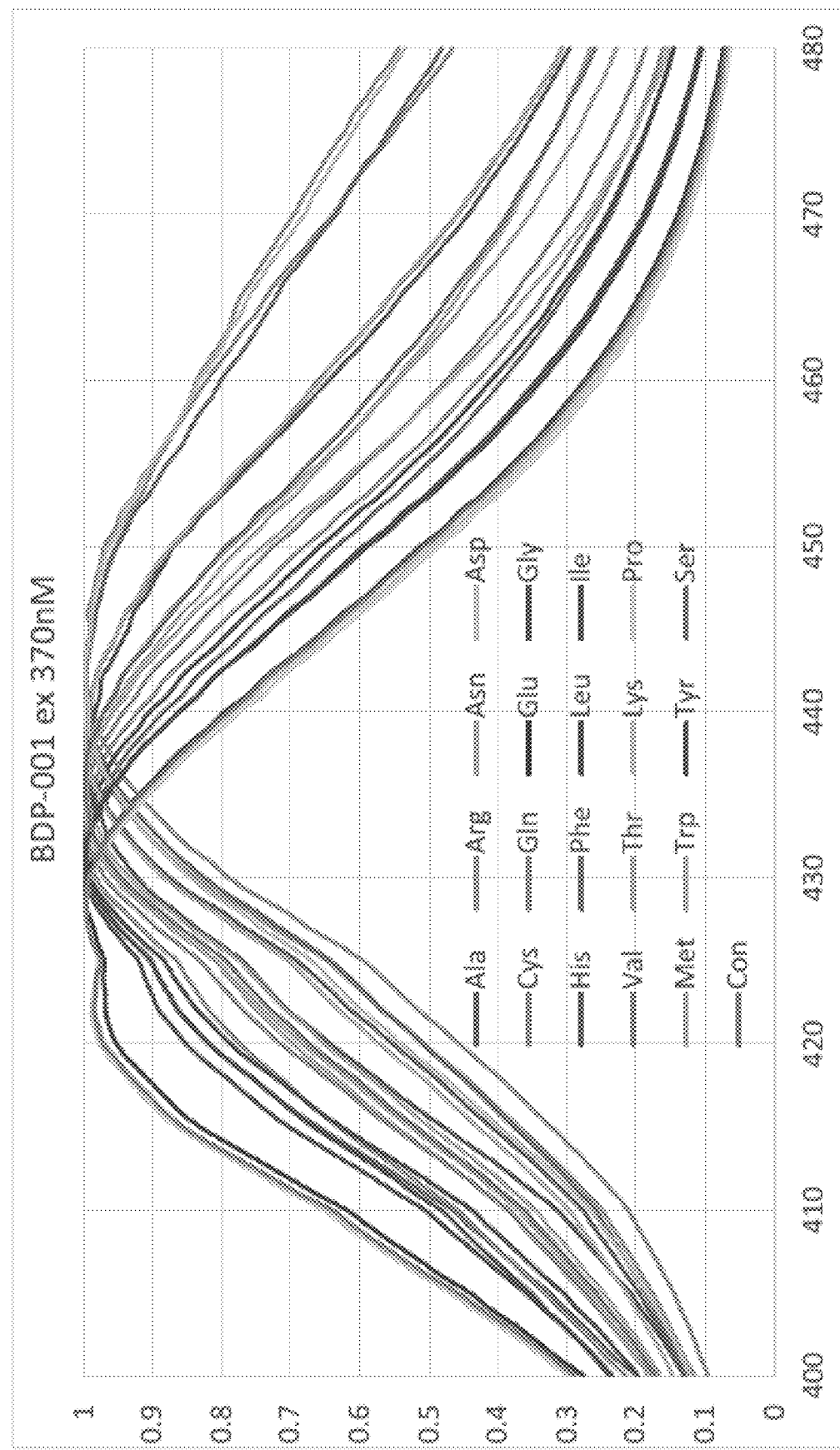
FIGS. 7-22 show fluorescence of exemplary BODIPY dyes BDP-001 (FIG. 7), BDP-002 (FIG. 8), BDP-003 (FIG. 9), Bodipy-004 (FIG. 10), Bodipy-005 (FIG. 11), Bodipy-006 (FIG. 12), Bodipy-007 (FIG. 13), BDP-008 (FIG. 14), BDP-009 (FIG. 15), BDP-010 (FIG. 16), BDP-011 (FIG. 17), BDP-012 (FIG. 18), Bodipy-013 (FIG. 19), Bodipy-014 (FIG. 20), BDP-015 (FIG. 21), and Bodipy-016 (FIG. 22) conjugated with different amino acids.
Figure 8:
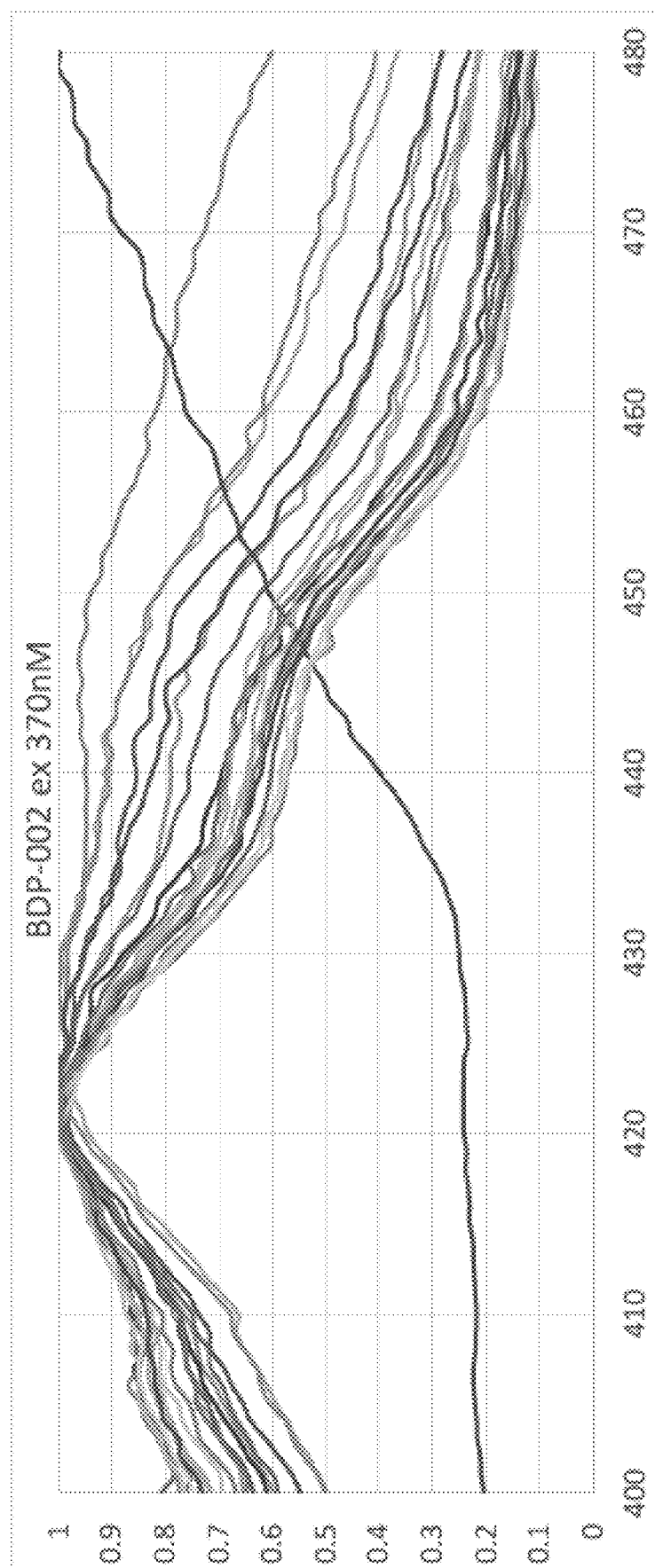
Figure 9:
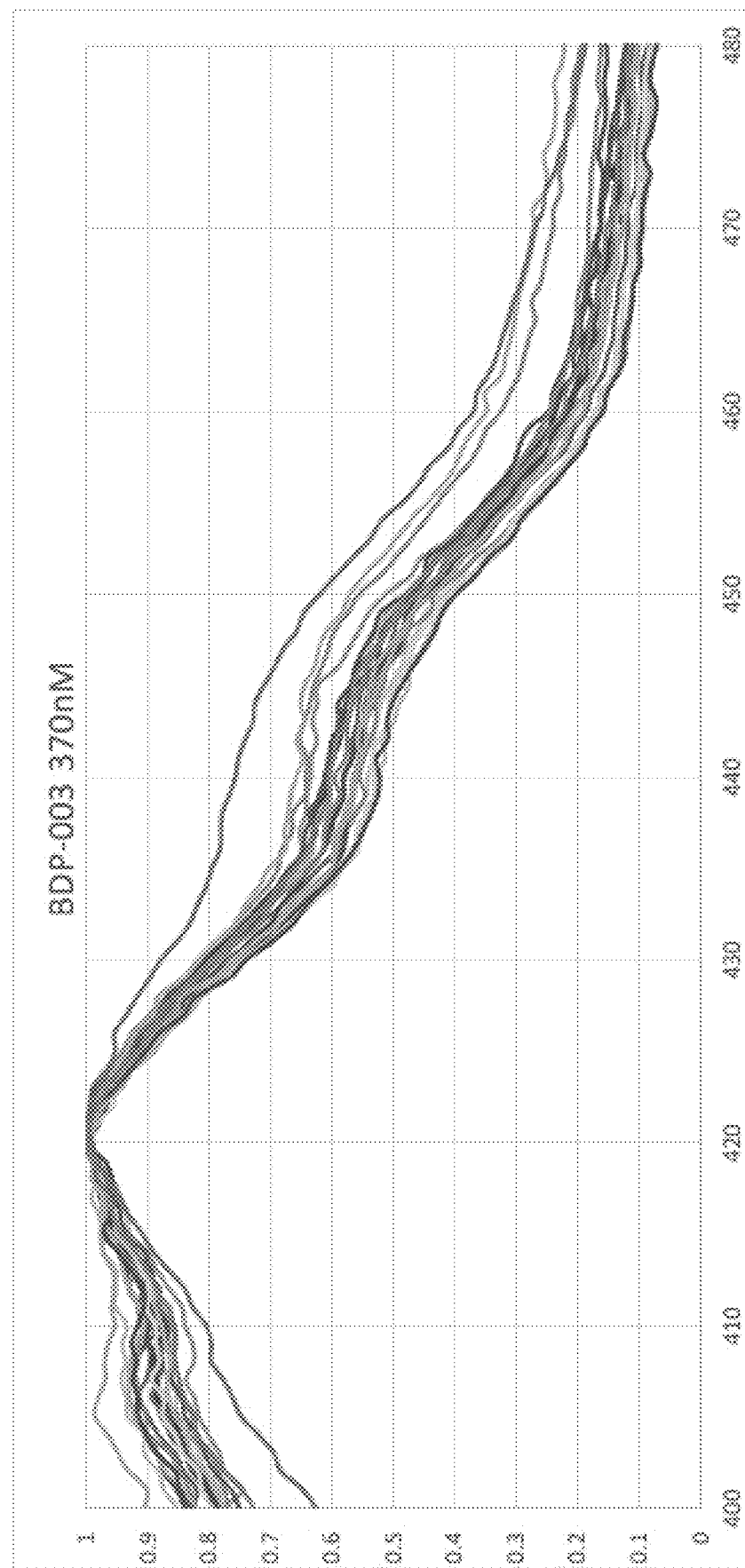
Figure 10:
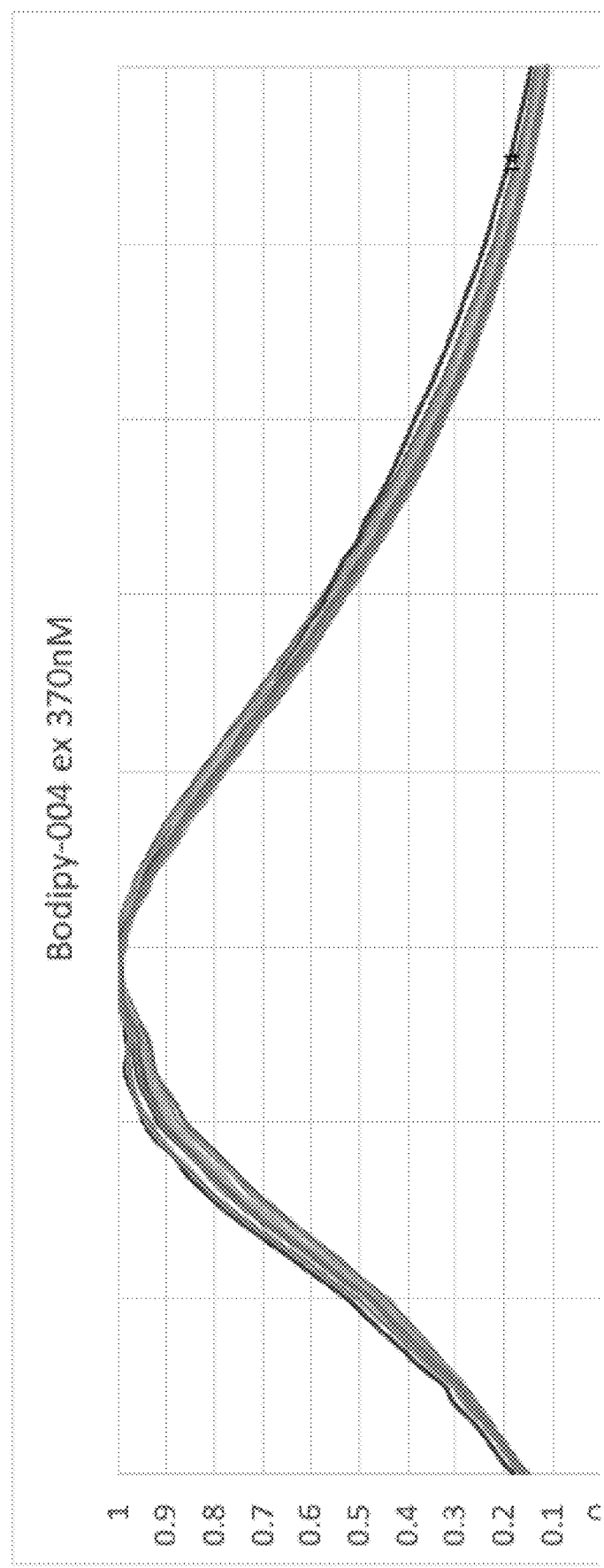
Figure 11:
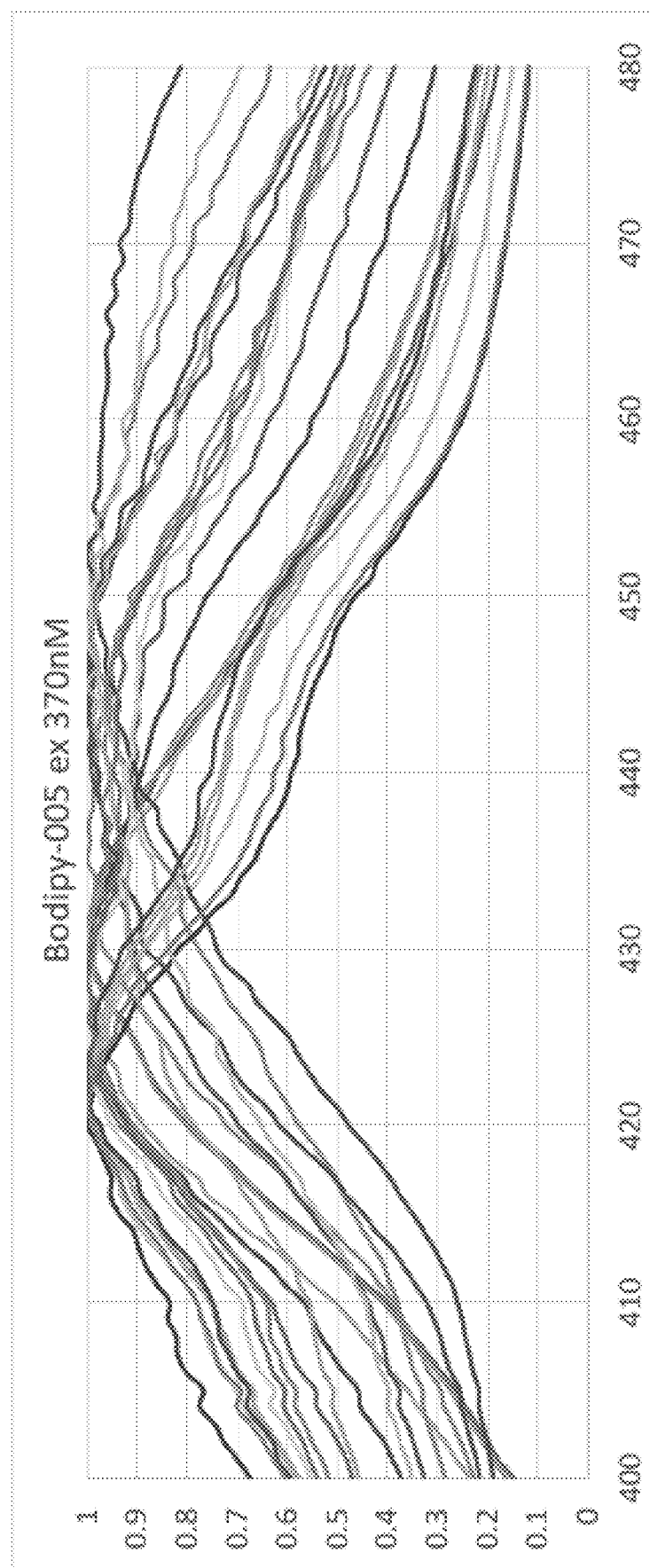
Figure 12:
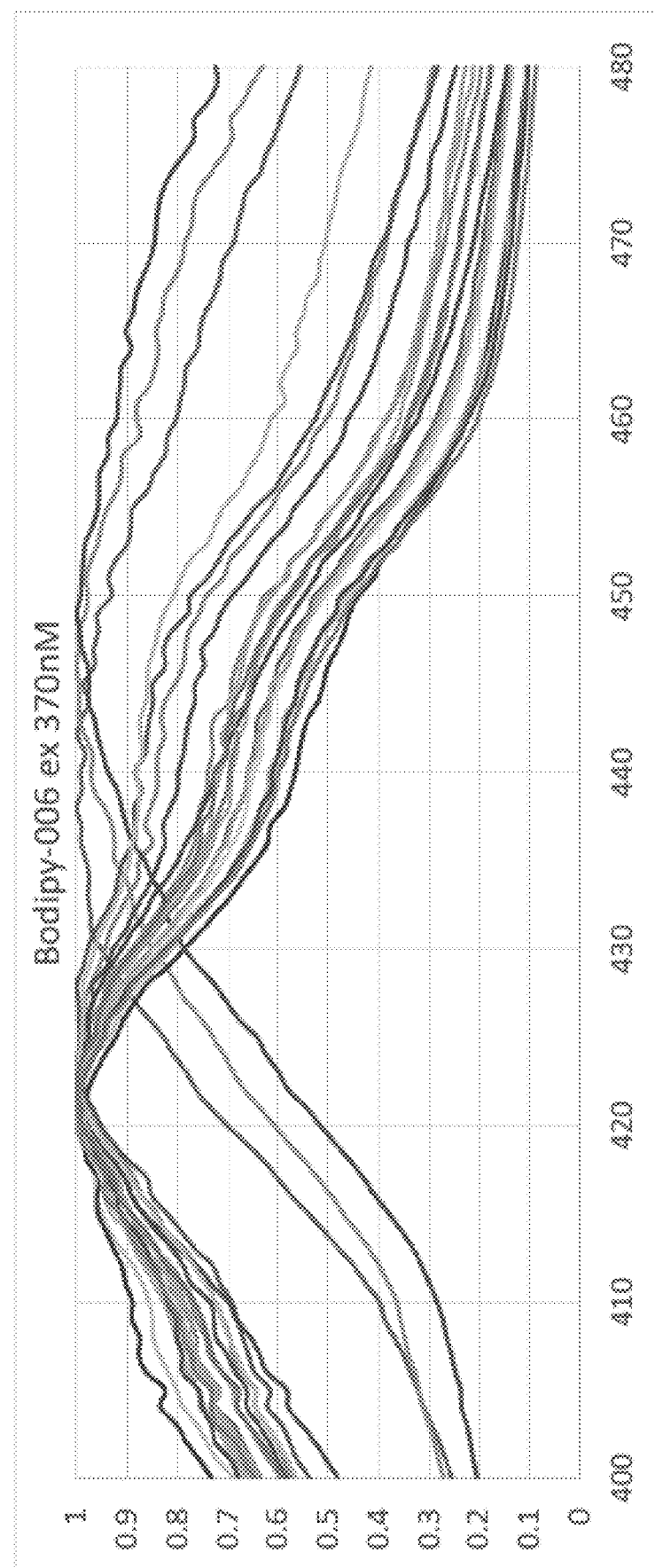
Figure 13:
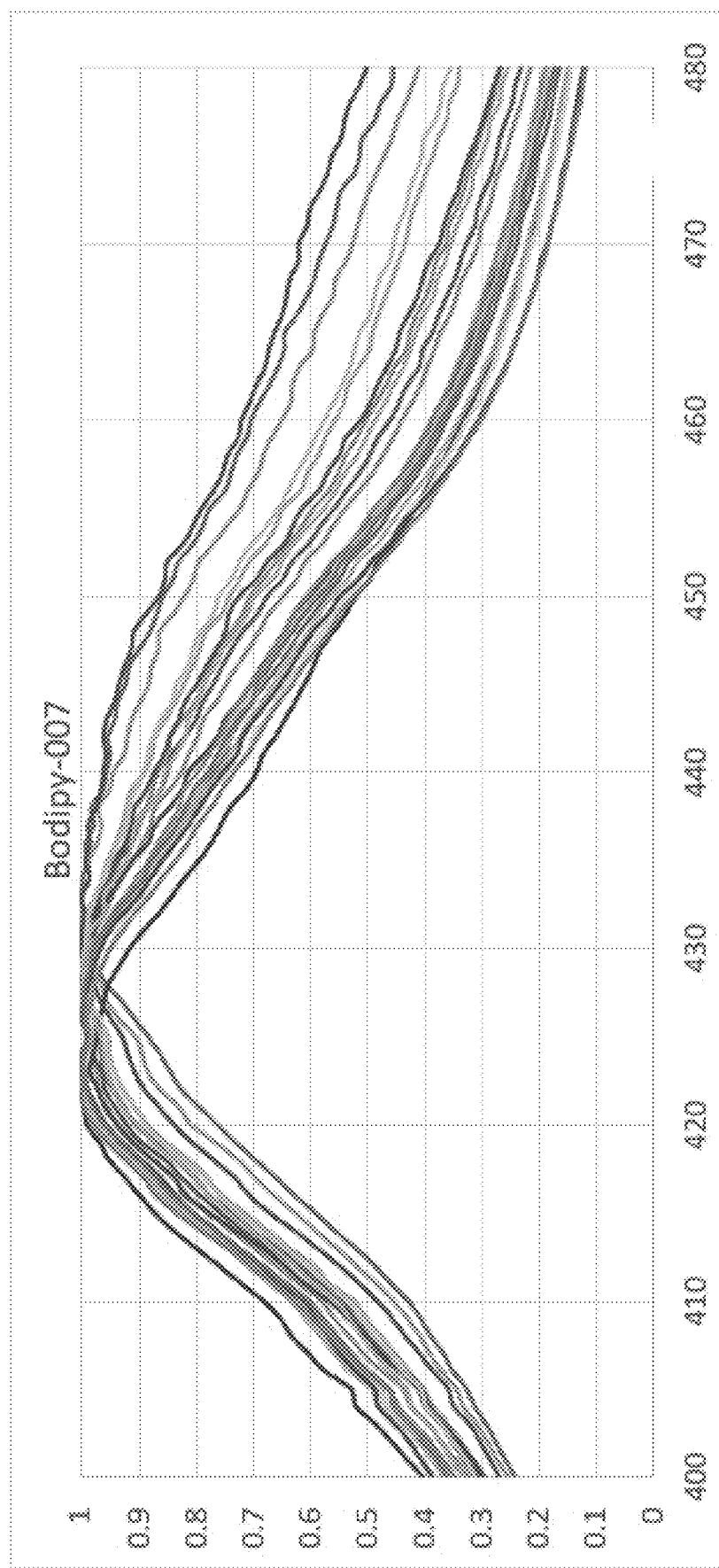
Figure 14:
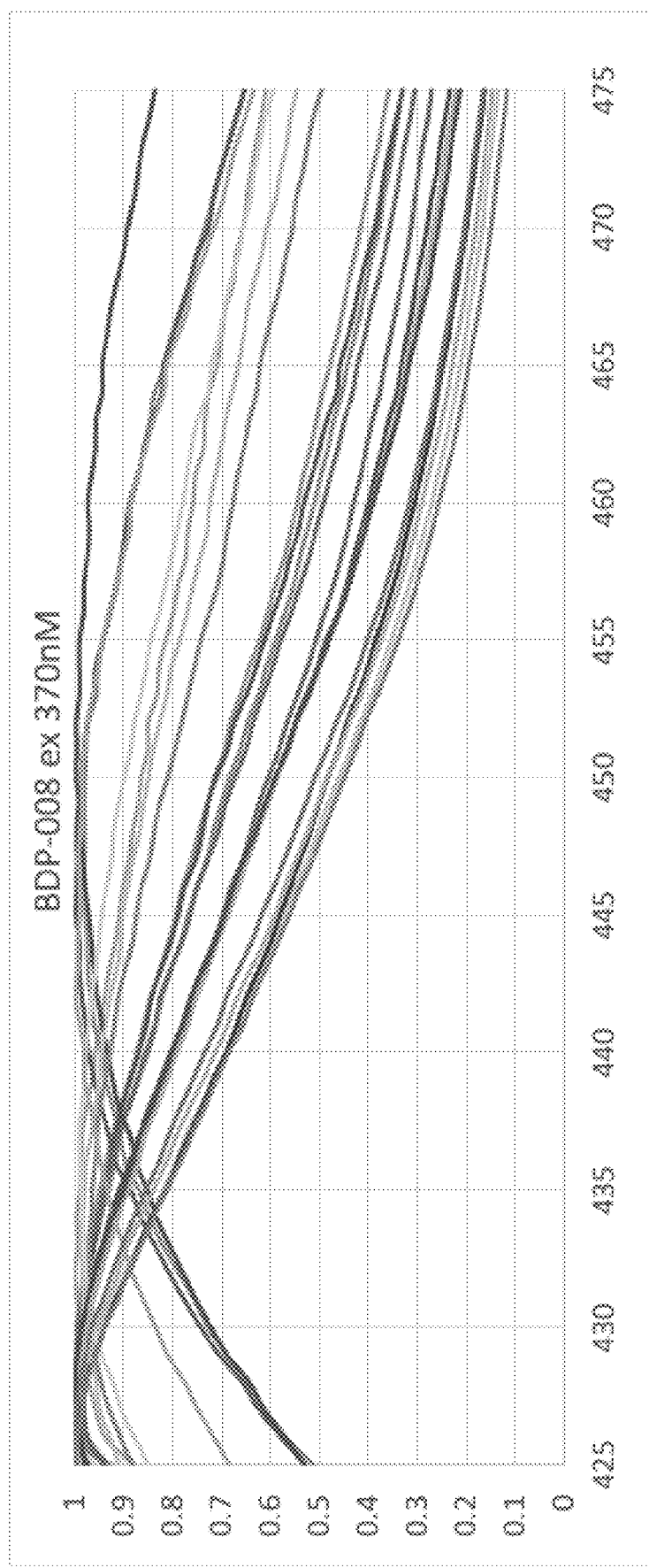
Figure 15:
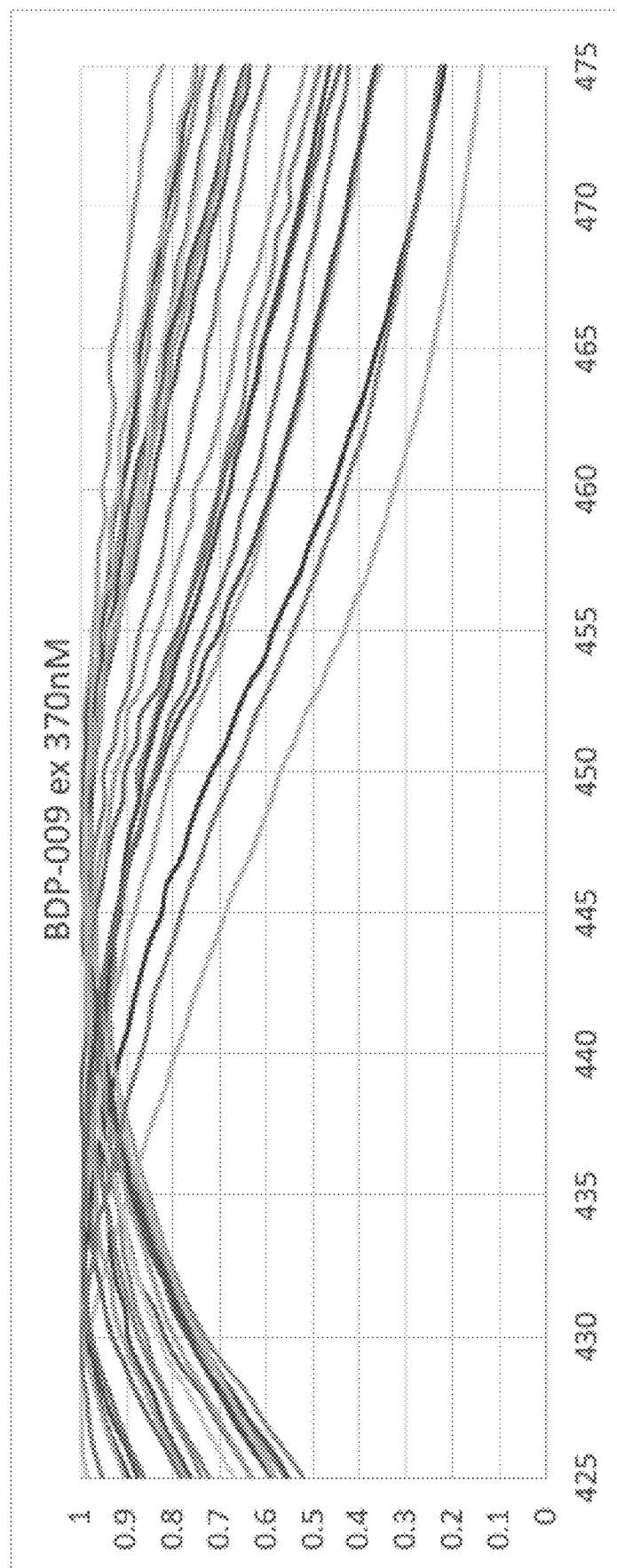
Figure 16:
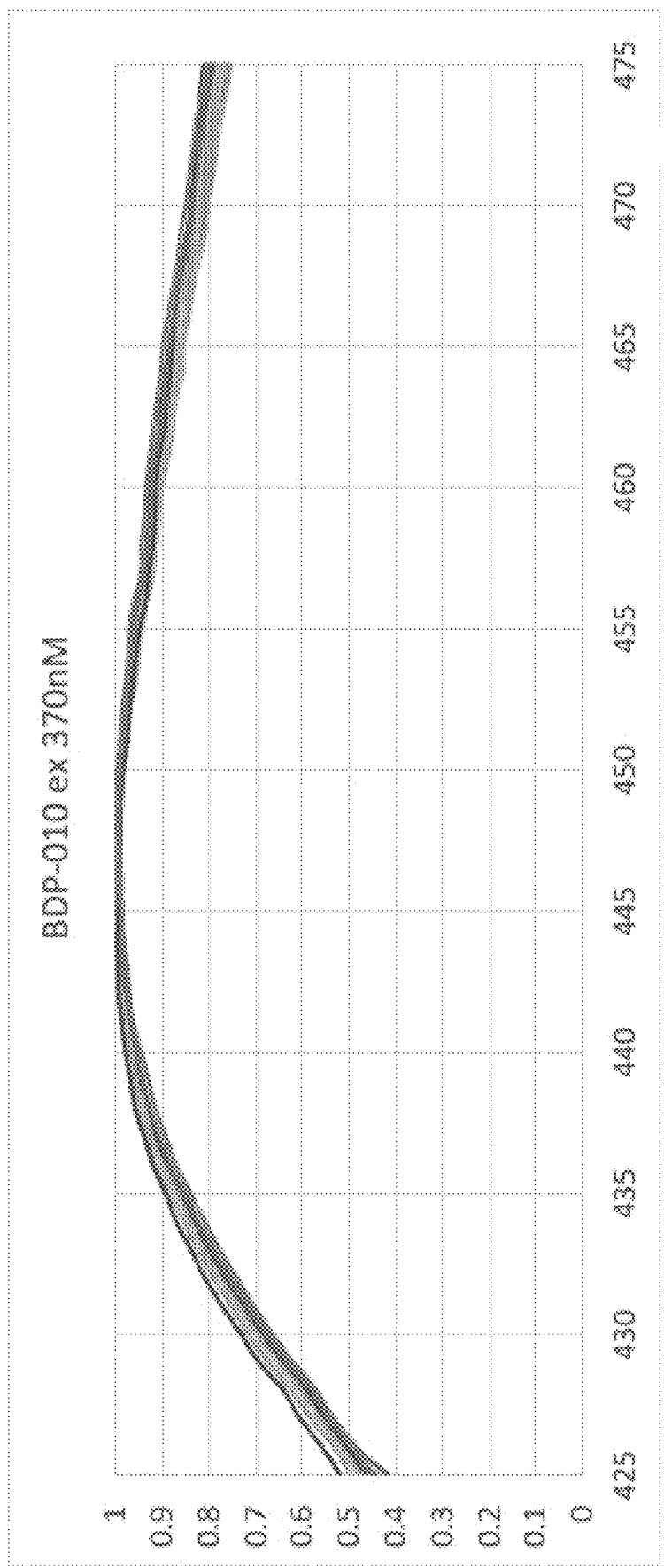
Figure 17:
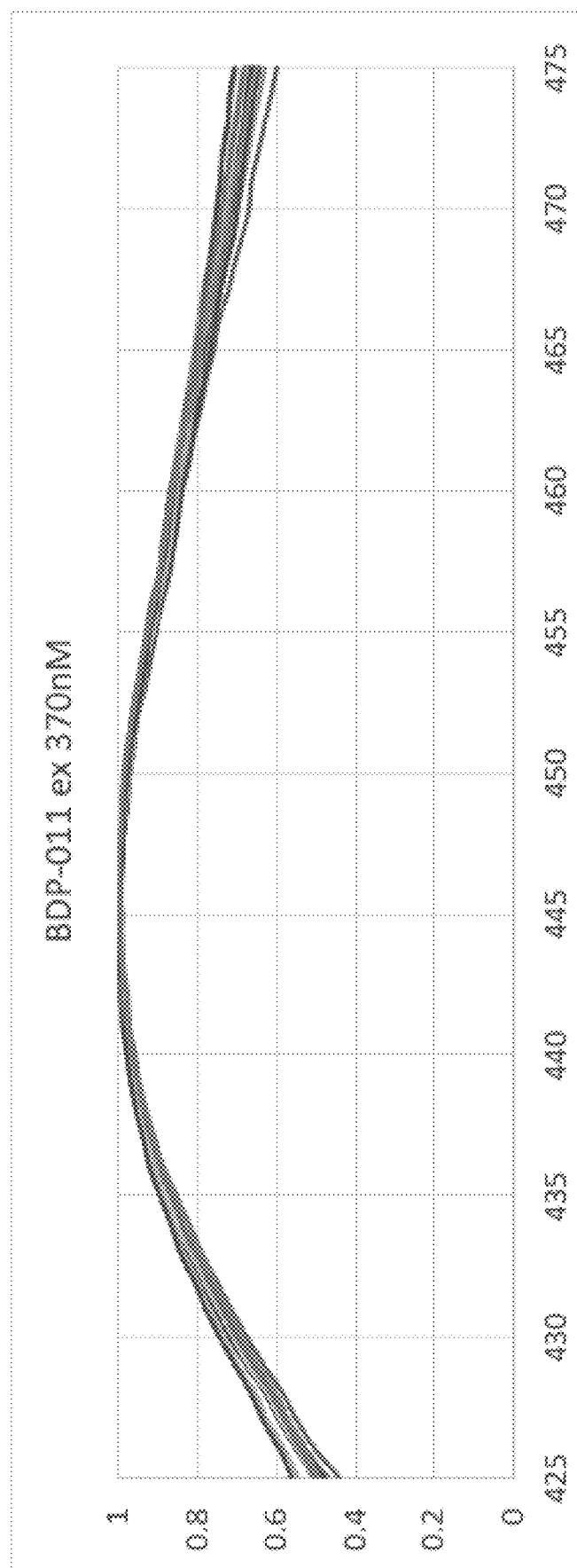
Figure 18:
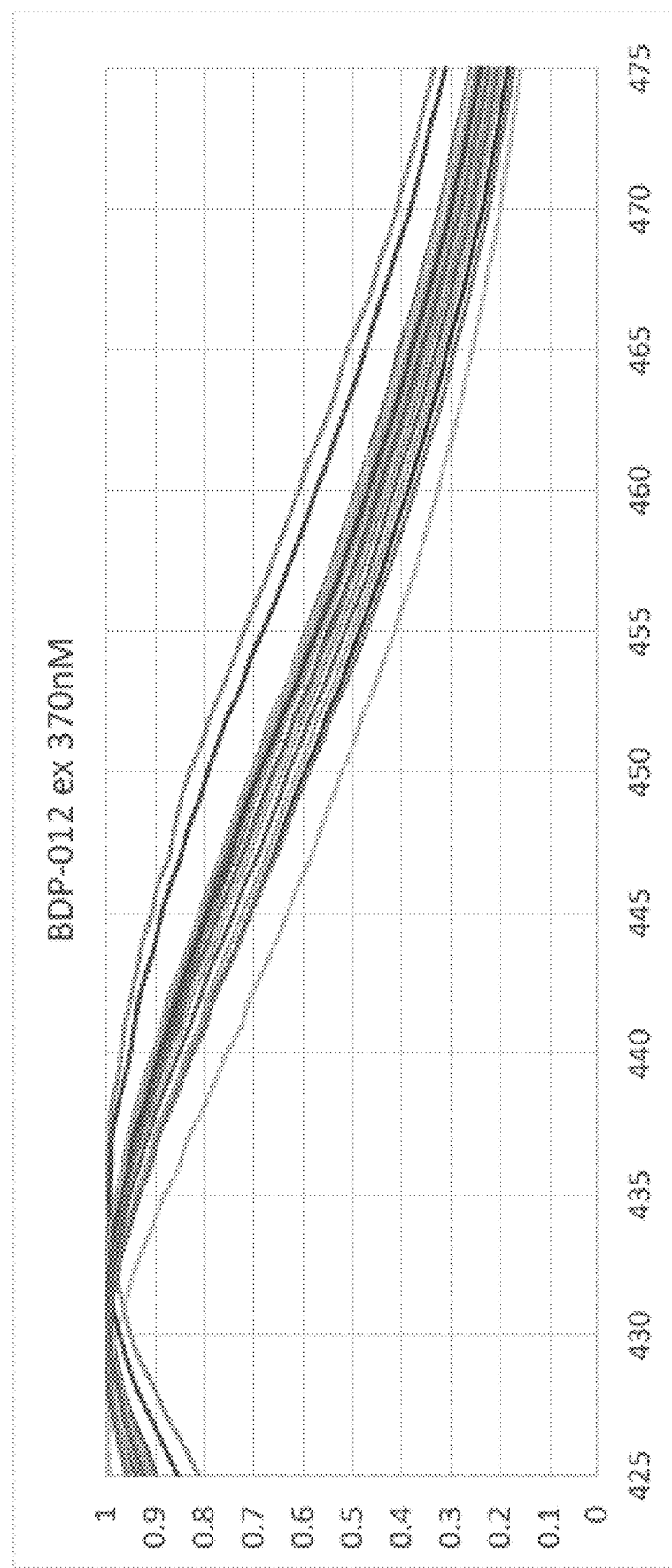
Figure 19:
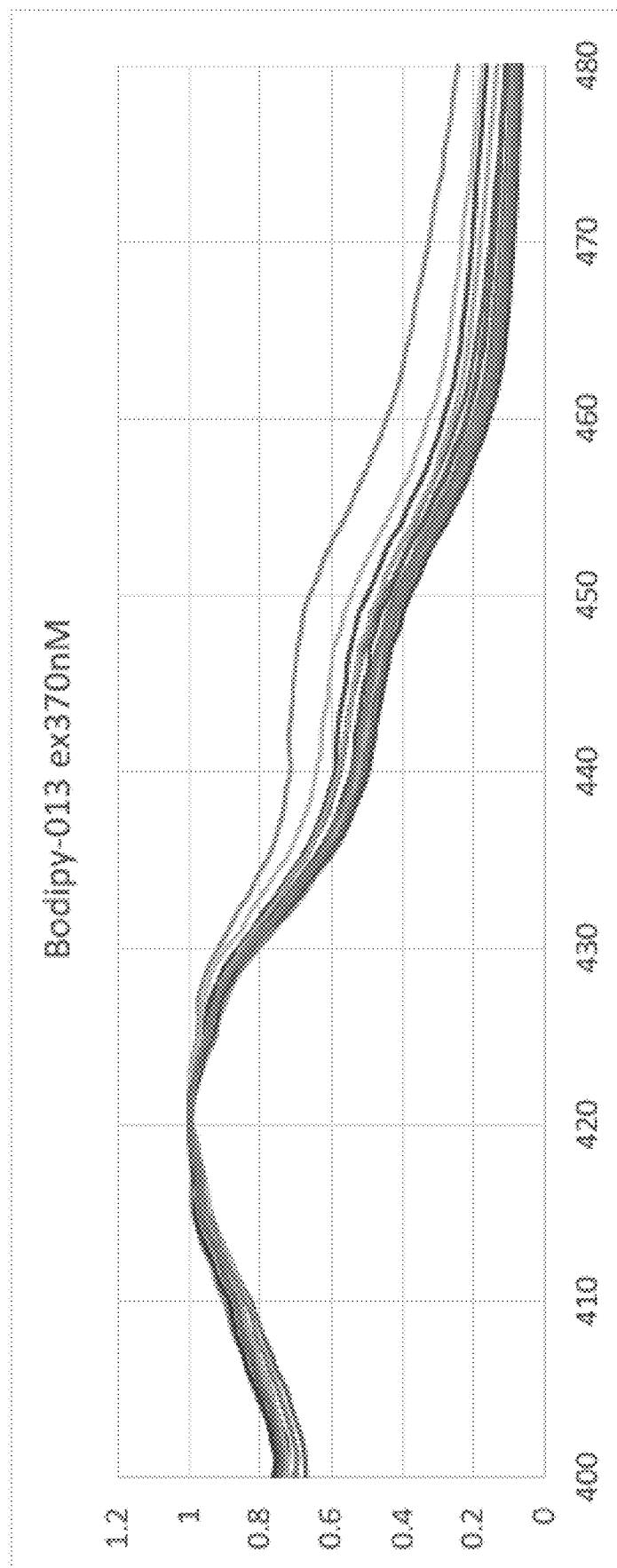
Figure 20:
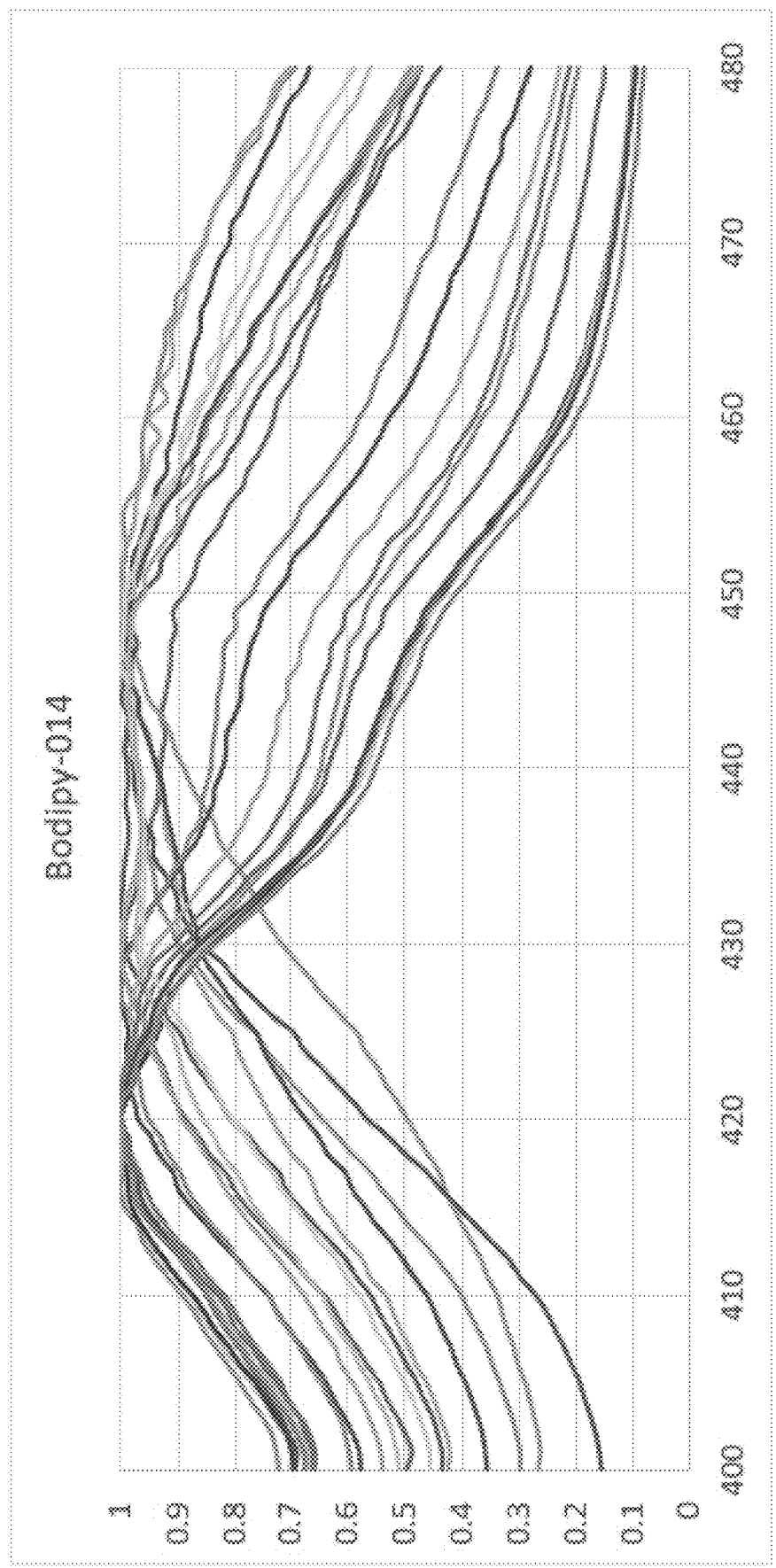
Figure 21:
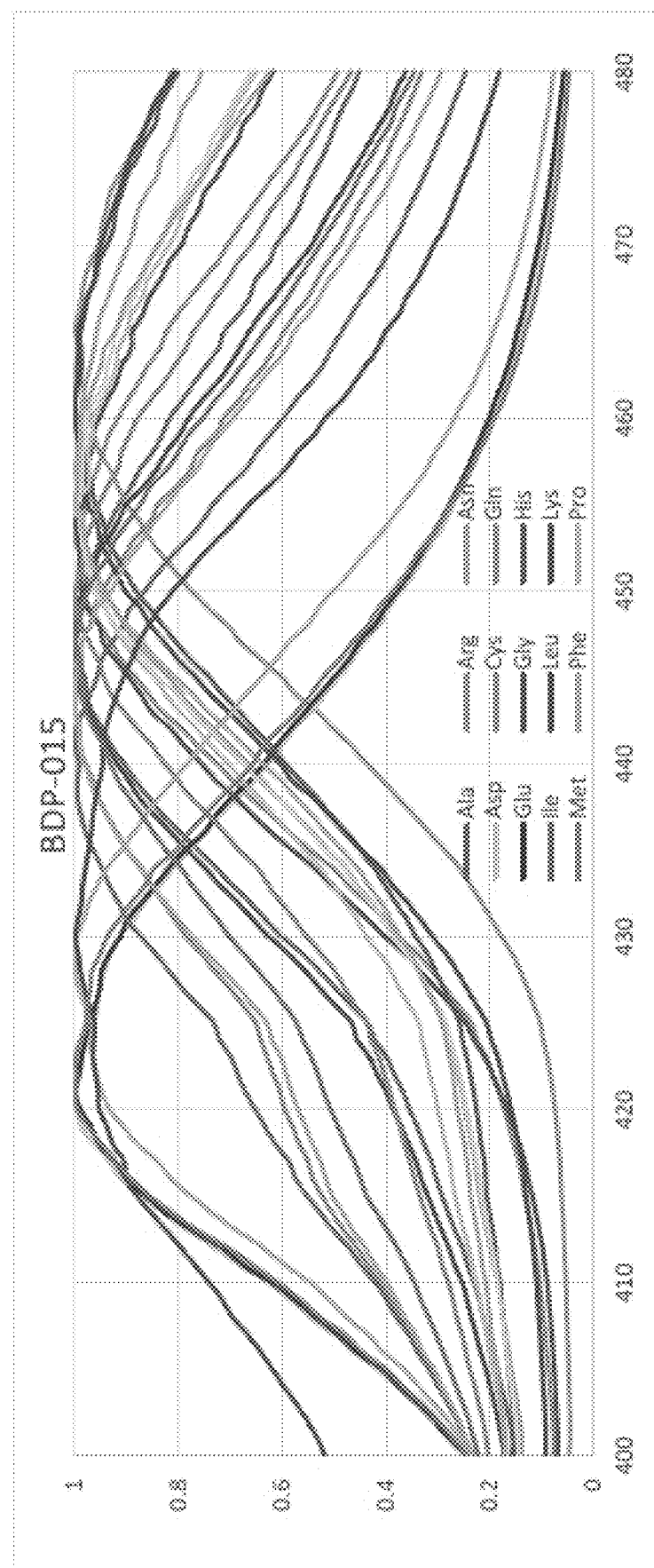
Figure 22:
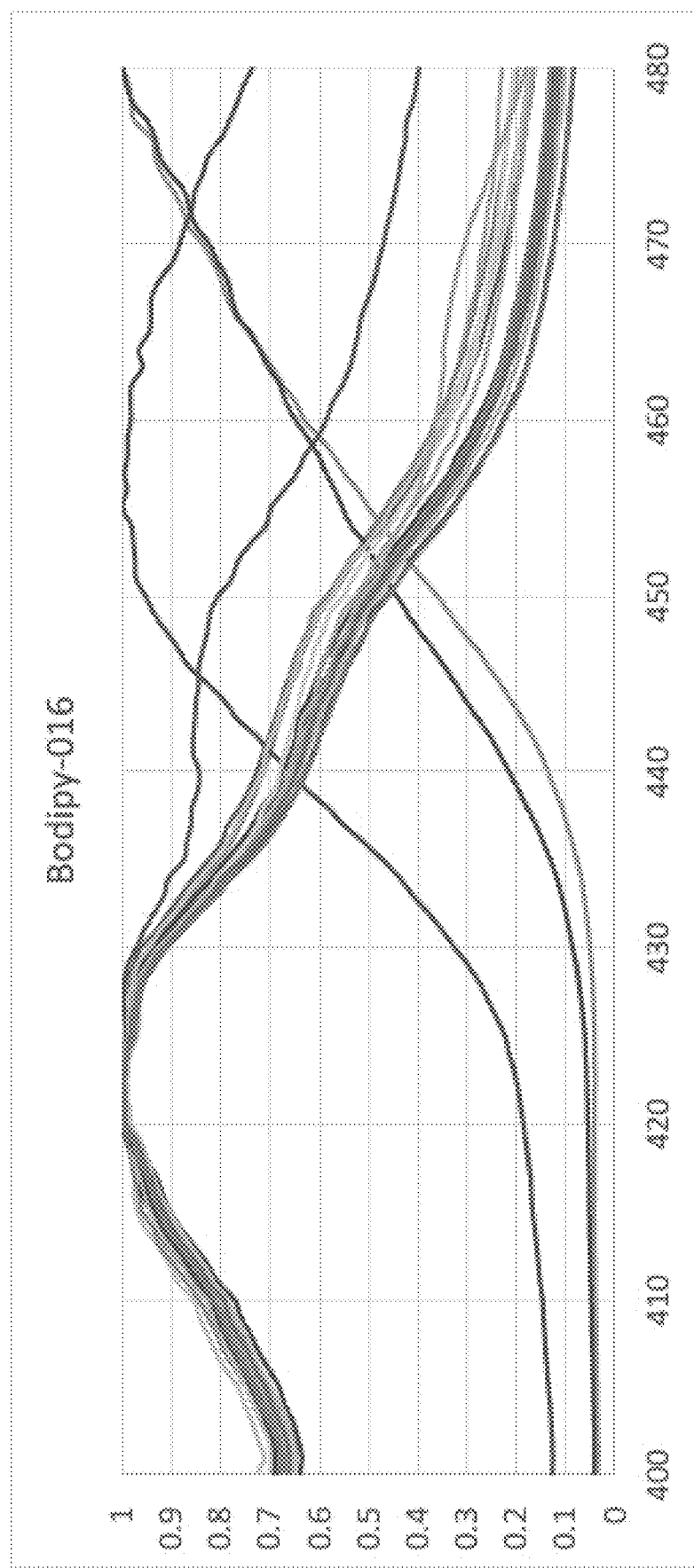

Novel BODIPY derivatives are synthesized using known synthetic methods from readily available starting materials (Scheme 1 and Scheme 2). The dye can be subjected to amino acids or polypeptides in solution, on a microarray, or in fix cells under normal PBS or similar buffered conditions resulting in conjugation to the amino acid nitrogen (FIG. 1). The spectral properties are measured and the information is used to determine the identity of the directly conjugated amino acid (FIG. 7).

Method 1: 8-Thioether BODIPY Core Synthesis

Exemplary 8-thioether BODIPY dyes were synthesized using the method shown in Scheme 1.

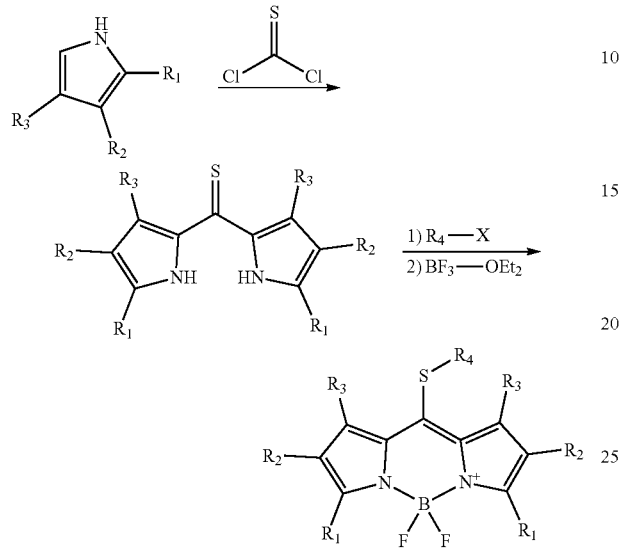

Scheme 1: General synthesis of 8-thioehter BODIPY dye core

The synthesis began with the formation of a thioketone. In anhydrous THF under inert atmosphere, pyrrole derivative (2 equivalents) was added and cooled to 0° C. using an ice-water bath. Thiophosgene (1 equivalent) was then added, and the reaction was allowed to stir for 15 minutes at 0 C. The reaction was quenched with methanol, concentrated, and purified via flash chromatography (5-20% ethyl acetate/hexanes).

Figure 2:
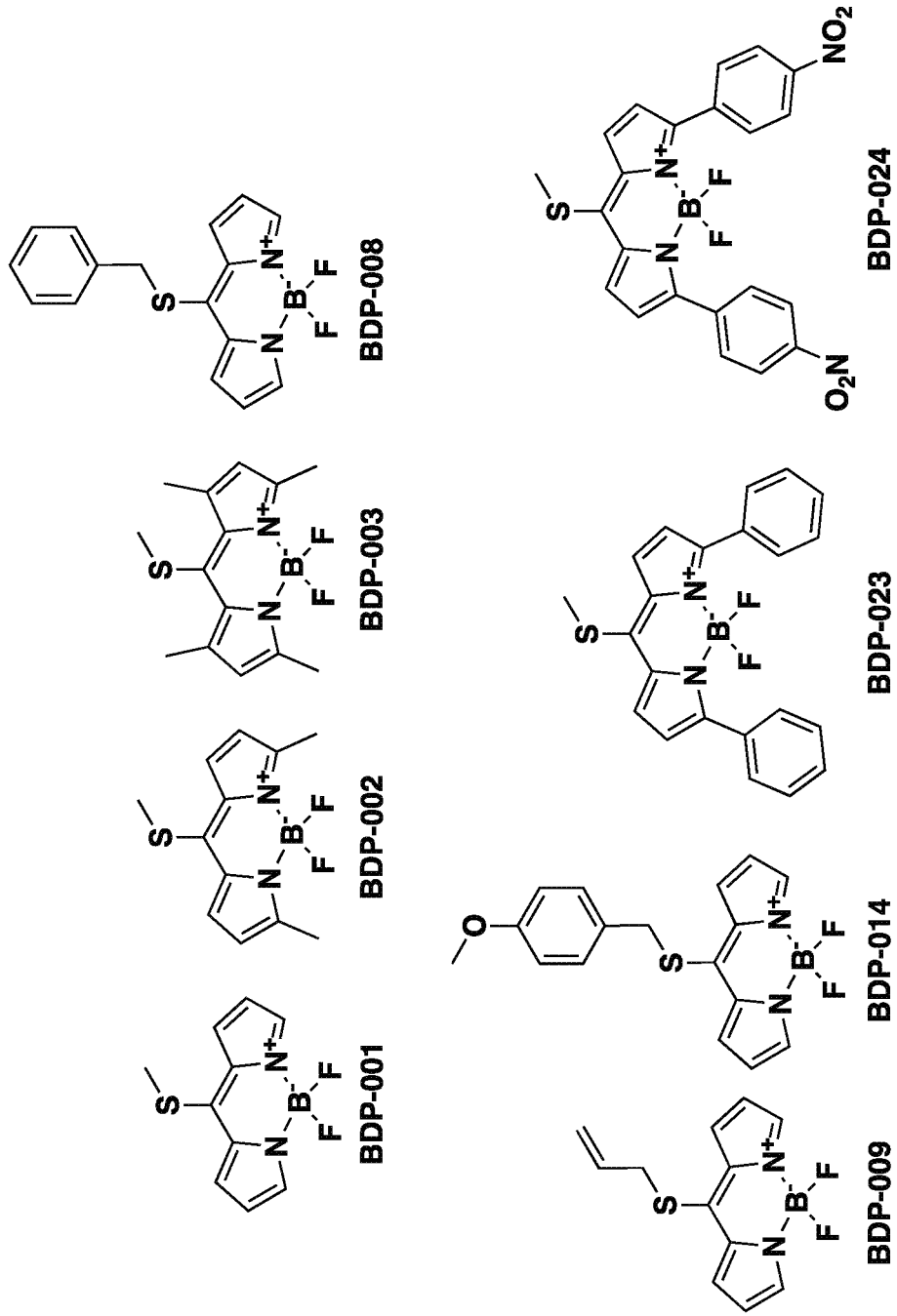
FIGS. 2-6 depict some exemplary compounds (probes) synthesized using exemplary synthesis methods described herein.

The thioketone was then taken up in anhydrous DCM under inert atmosphere and an alkyl halide (10 equivalents) was added. The reaction was monitored by TLC. Once complete the crude mixture was concentrated to dryness under reduced pressure to remove excess alkyl halide, and resuspended in anhydrous DCM. To the solution was added trimethylamine (5 equivalents). The solution was allowed to stirred at room temperature under inert atmosphere for 30 minutes. After 30 minutes, $BF_3 \cdot OEt_2$ was added and the solution stirs until starting material is consumed by TLC. The reaction is concentrated and purified via flash chromatography (5-20% ethyl acetate/hexanes) to produce the 8-thioether BODIPY. Exemplary BODIPY dyes made by this method are shown in FIG. 2.

Method 2: 8-chloro and 8-arylthioether BODIPY Synthesis

Exemplary 8-chloro and 8-arylthioether BODIPYs were synthesized as shown in Scheme 2.

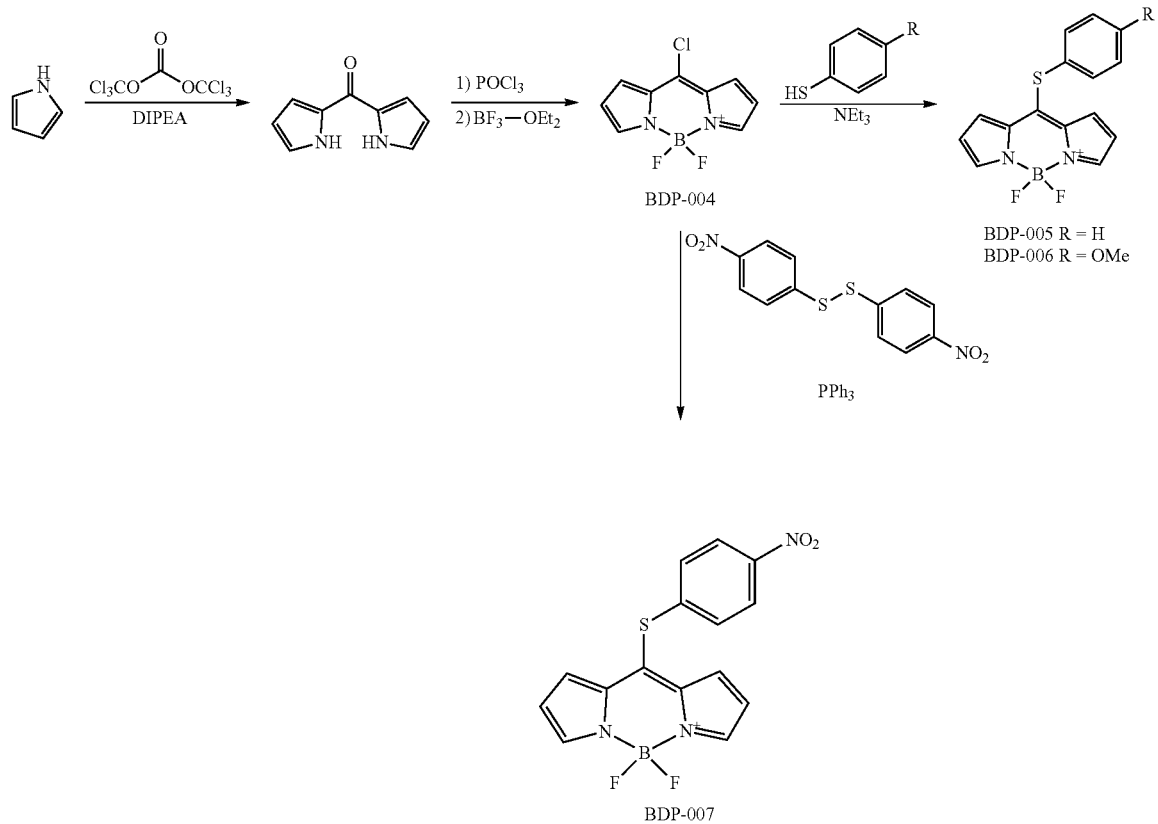

Scheme 2: General synthesis of 8-chloro BODIPY and 8-arylthioether BODIPYs

In anhydrous DCE under inert atmosphere, pyrrole (1 equivalent) and diisopropylethylamine (0.5 equivalent) were added and the solution cooled to 0 C using an ice-water bath. To the solution was added triphosgene (0.33 equivalents), and was allowed to stir at 0 C until full conversion by TLC. Once consumed, another equivalent of pyrrole was added, and the solution was then refluxed until full conversion to the ketone. The solution was then cooled, diluted with diethyl ether, and washed with water. The organic layer was dried, concentrated and purified by flash chromatography (20% ethyl acetate/DCM).

8-chloro BODIPY was then substituted to form the 8-aryl-thioether BODIPY. This was achieved by two different methods:

1. 8-chloro BODIPY (1 equivalent), aryl thiol (1 equivalent), and trimethylamine (1 equivalent) were added to anhydrous DCM. The reaction stirred under ambient condition until completion by TLC. Reaction was concentrated and purified by flash chromatography.

2. 8-chloro BODIPY (1 equivalent), aryl disulfide (1 equivalent), and triphenylphosphine (1 equivalent) were added to anhydrous DCM. The reaction stirred under ambient condition until completion by TLC. Reaction was concentrated and purified by flash chromatography.

Method 3: Tetrahalogentation of 8-thioether BODIPY

Tetrahalogenated 8-thioether BODIPYs were synthesized using the method shown in Scheme 3.

Scheme 3: Synthesis of tetrahalogenated 8-thioether BODIPYs

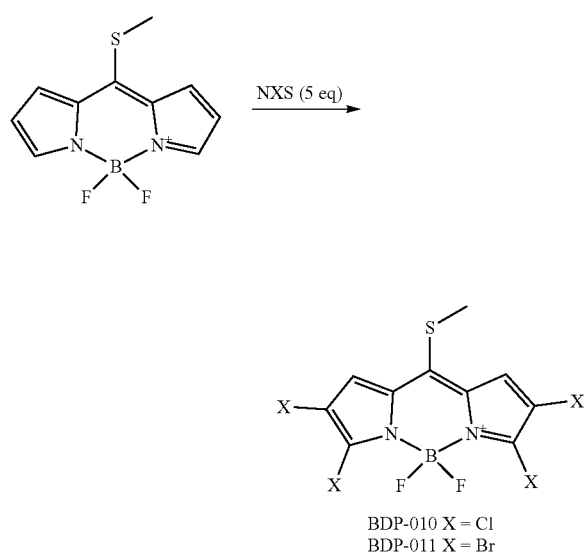

BDP-010 X = Cl
BDP-011 X = Br

Unsubstituted BODIPY (BDP-001) was added to THF and cooled to −40 C. N-halosuccinimide (5 equivalents) was added slowly to the solution, and was monitored by TLC. Once complete, reaction was warmed to room temperature, concentrated, and purified via flash chromatography (10% ethyl acetate/hexanes).

Method 4: Aldehyde Addition to 8-Thioehter BODIPY Through Vilsmeier-Haack

β-formyl-8-thioehter BODIPYs were synthesized as shown in Scheme 4.

Scheme 4: Synthesis of beta-formyl substituted 8-thioether BODIPYs

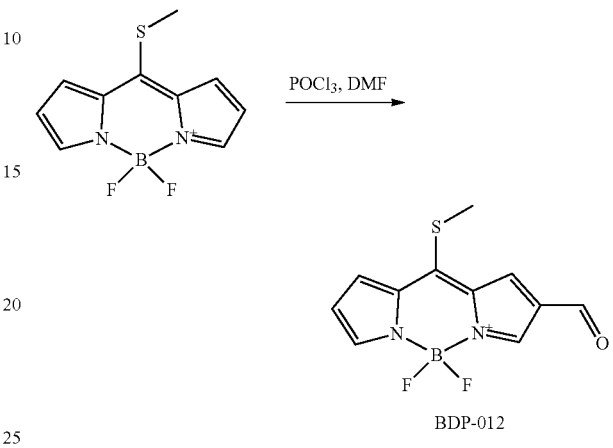

BDP-012

DMF was added an equal portion of POCl2, and stirred in an ice bath for 5 min under inert atmosphere. After 5 minutes, the solution was allowed to warm to room temperature, and was stirred for an additional 30 minutes. To this reaction mixture was added unsubstituted BODIPY (BDP-001) in DCE, the temperature was raced to 50° C., and the mixture was stirred for an additional 2 hours. After 2 hours, the solution was poured into ice water, an was extracted with DCM. The organic layer was dried, filtered, concentrated, and purified by flash chromatography to produce β-formyl substituted 8-thioether BODIPY.

Method 5: Extended Conjugation Dyes Through Knoevenagel Condensation

Extending the conjugation through mono- and bis-styryl BODIPYs was achieved through Knoevenagel condensation as shown in Scheme 5.

Scheme 5: General synthesis of condensed 8-thioether BODIPy dyes

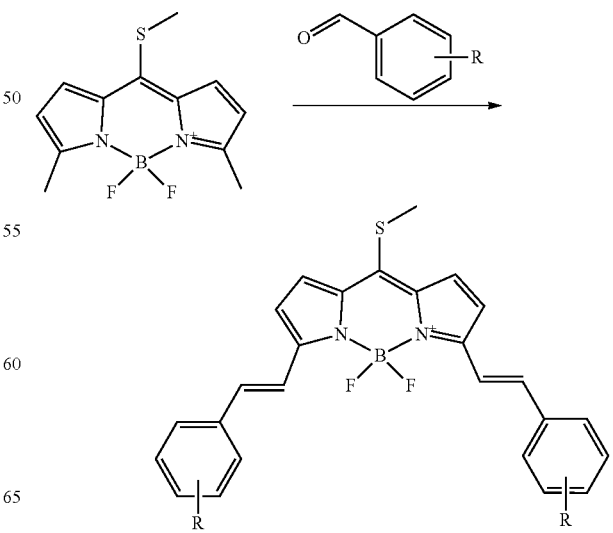

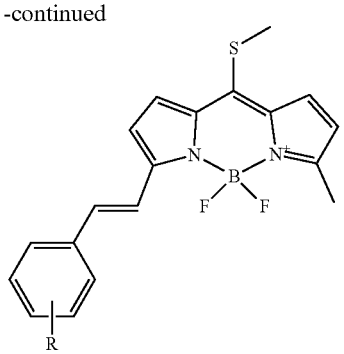

α, α'-dimethyl 8-thioester BODIPY (BDP-002) (1 equivalent) was mixed with aryl aldehyde (10 equivalents), anhydrous toluene, and 4-Å molecular sieves. Acetic acid (0.1 equivalent) and piperidine (0.1 equivalent) were added and the solution was refluxed. Once starting material was consumed, the reaction was filtered, concentrated, and purified by flash chromatography to obtain the mono-styryl and bis-styrl 8-thioether BODIPY dyes.

Figure 3:
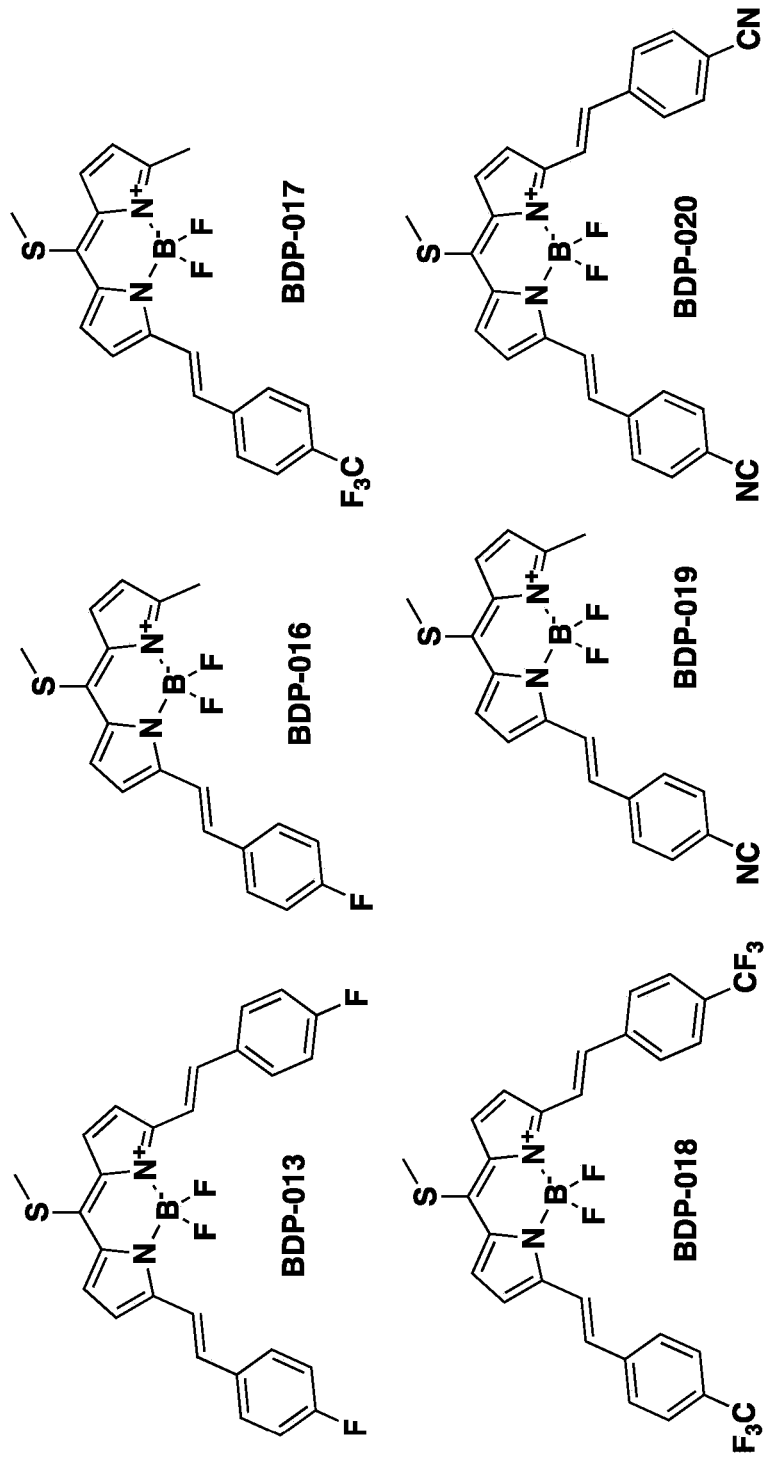

Exemplary BODIPY dyes made by this method are shown in FIG. 3.

Method 6: Sulfonation of 8-Thioether BODIPY Dyes Through Electrophilic Aromatic Substitution Electrophilic aromatic substitution of the 8-thioether BODIPY was performed to introduce β-sulfonates as shown in Scheme 6.

Scheme 6: General synthesis of condensed 8-thioether BODIPy dyes

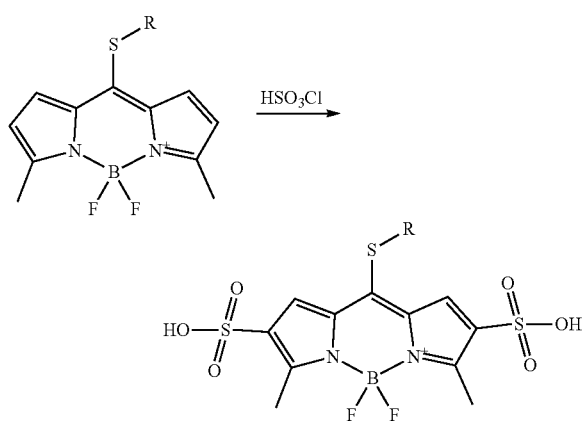

α, α'-dimethyl 8-thioester BODIPY (BDP-002) (1 equivalent) was added to anhydrous DCM under inert conditions and cooled to −40 C. Chlorosulfonic acid (3.7 equivalents) in anhydrous DCM was added dropwise to the reaction, and was allowed to stir for 20 minutes at −40 C. The reaction was then warmed to −15 C for 30 minutes, and followed by warmed to room temperature. The solution was allowed to stir for another hour at room temperature. The precipitate formed was triturated with DCM several times. The solid was dried under reduced pressure to give the β-β'-sulfonated 8-thioether BODIPY.

Figure 4:
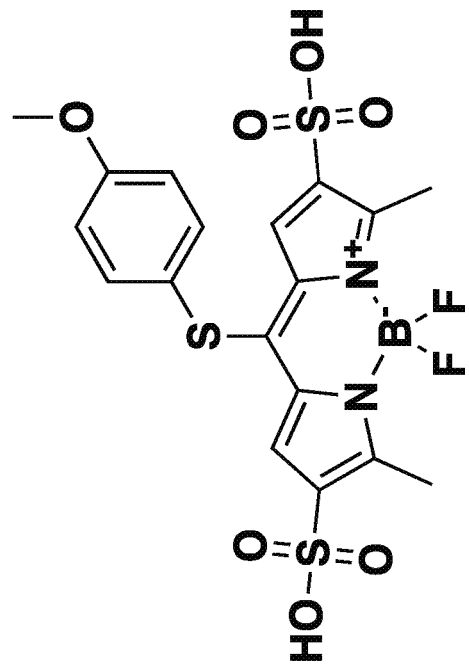
Figure 4:
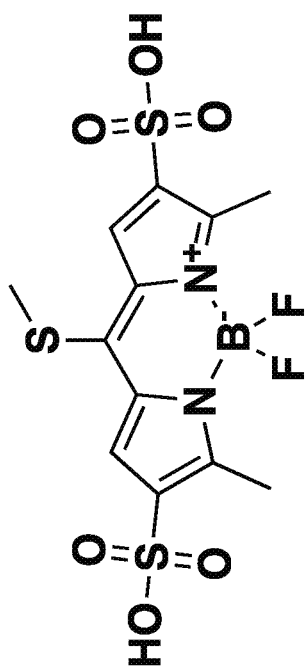

Exemplary BODIPY dyes made by this method are shown in FIG. 4.

Method 7: Pyrrole Biaryl Synthesis Via Suzuki Coupling

To create bis-biaryl 8-thioether BODIPYs, Suzuki coupling (Scheme 7) can be used to form the biaryl pyrroles that can be then be used as the starting material in Method 1 above.

Scheme 7: General synthesis of pyrrole biaryls

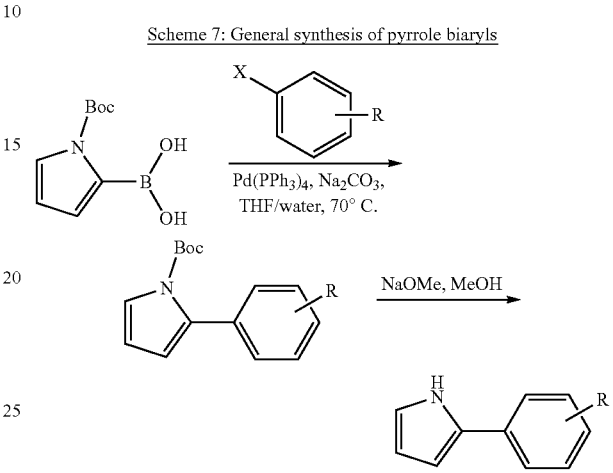

Bo-pyrrole-2-boronic acid (1 equivalent) was added to water/THF with aryl halide (1.1 equivalents), sodium carbonate (2 equivalents), and palladium tetrakis triphenylphosphine (0.2 equivalents). The solution was degassed with nitrogen, and heated to 70 C until full conversion was observed by TLC. The reaction was diluted with water and extracted with DCM. The organic layers were dried, filtered, concentrated, and purified via flash chromatography.

The Boc-biaryl (1 equivalent) was then taken up in methanol and sodium methoxide (10 equivalents) was added, and heated to 50 C. The reaction was monitored by TLC. Once product was fully formed, the reaction was quenched with aqueous saturated ammonium chloride, and washed with DCM. The organic layers were dried, filtered, concentrated, and purified via flash chromatography to create the biaryl that can be used as the starting material in Method 1.

Figure 5:
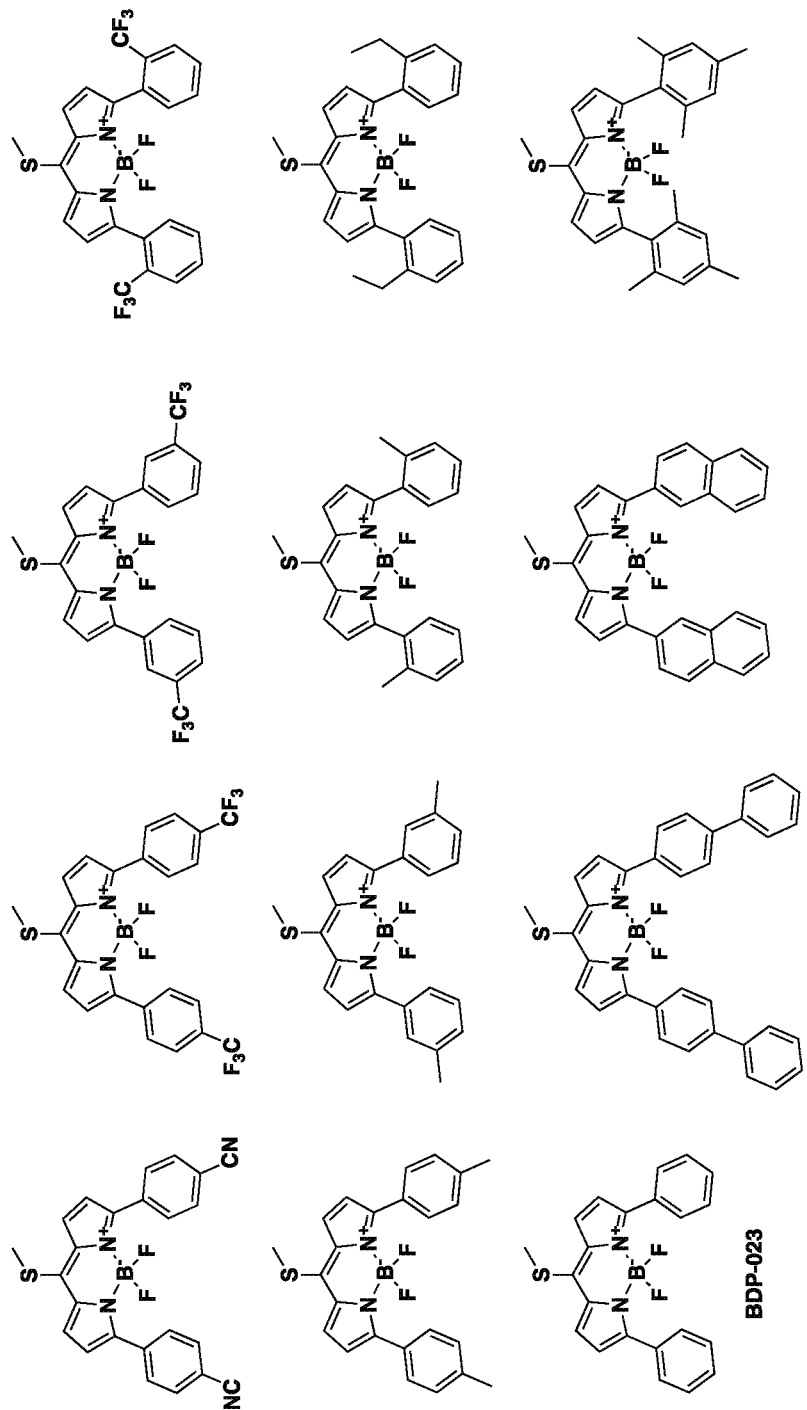

Exemplary BODIPY dyes using the biaryls produced by this method and as the starting material in Method 1 are shown in FIG. 5.

Method 8: Asymmetrical Biaryl Dye Synthesis Via Photo-Activation

Scheme 8: General synthesis of asymmetric pyrrole biaryls

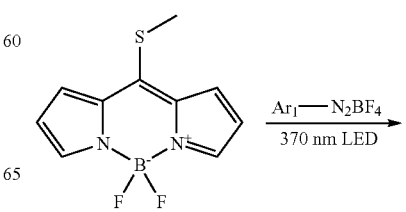

-continued

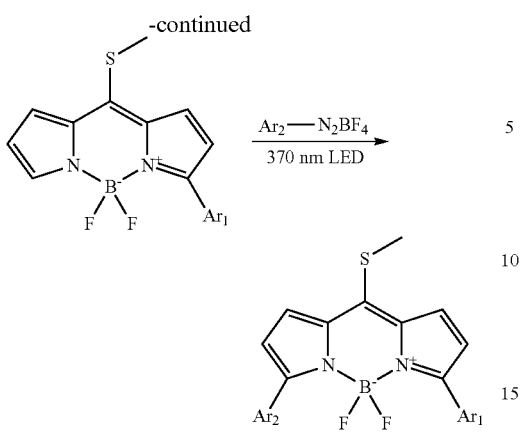

To create asymmetrical bis-biaryl 8-thioether BODIPYs, unsubstituted BODIPY (BDP-001) (1 equivalent) and aryl diazonium tetrafluoroborate salt (1-2 equivalents) were mixed in anhydrous acetone, and were spared with nitrogen gas for 15 minutes (Scheme 8). The solution was sealed and exposed to a 370 nm LED until complete conversion to the mono-biaryl. The mono-biaryl is purified via flash chromatography (30-50% toluene/hexanes). The mono-biaryl is then mixed with a different aryl diazonium tetrafluoroborate salt (1-2 equivalents) in anhydrous acetone. The solution was sparged with nitrogen gas for 15 minutes, sealed, and exposed to a 370 nm LED until complete conversion to the asymmetrical biaryl 8-thioether BODIPY. The bis-biaryl was purified via flash chromatography (20-50% DCM/hexanes).

Method 9: Asymmetric Biaryl-Styryl Dye Synthesis Via Photo-Activation

Scheme 9: General synthesis of asymmetric biaryl-styryl BODPIY dyes

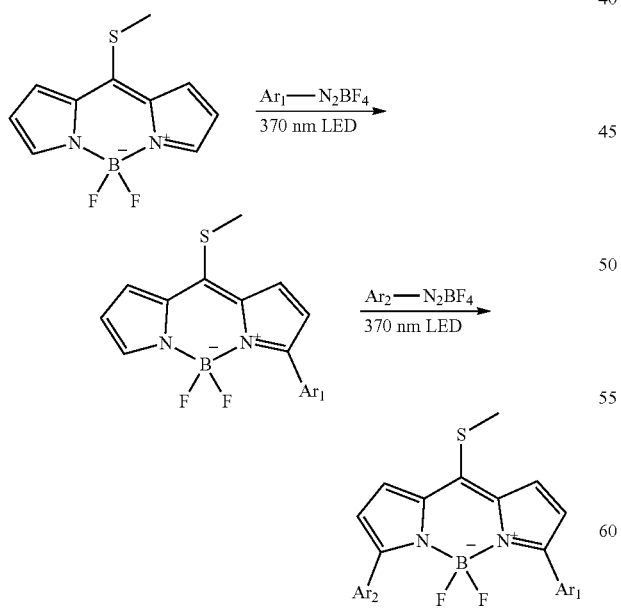

To create asymmetrical biaryl-styryl 8-thioether BODIPYs, an asymmetric a methyl 8-thioester BODIPY is first synthesized, e.g., via Method 1 using equal equivalents of pyrrole and 2-methylpyrrole for the thioketone formation. The mono-biaryl is then synthesized by Method 8. Following this, the asymmetrical biary-stryl is formed using the Knoevenagel condensation of Method 5.

Example 2: Conjugation of BODIPY Dyes to Amino Acids

Materials/Instrumentation:
  10 mM Stock solutions of the 20 natural amino acids are made in DMSO and stored in the −20° C. freezer.
  Stock solutions of dyes ranging from 10-100 mM are made in anhydrous DMSO and stored in the −20° C. freezer. This solution will be diluted out to 111 μM to be used in the testing step.
  Cellvis brand Black 384 well glass bottom black plate with #1.5 high performance cover glass (0.17±0.005 mm) part number: P384-1.5H-N (other 384 well plates will work the same these are just the ones we currently have on hand)
  Molecular Devices SpectraMax Gemini EM Microplate Reader
  Bioshaker Need part number or model Plate Pipetting Protocol:
  1. 384 well plate is opened and lid removed and oriented with A1 to the top left.
  2. The lights in this section of lab are dimmed to the minimal level required to safely complete the following steps (this is to minimize photobleaching from any overhead lights).
  3. The Dye and Amino acid solutions are taken out and allowed to thaw at room temperature.
  4. Then the necessary amount of Amino Acid solution (6 μl times the number of wells to be filled, i.e., 16 wells would need 96 1) is transferred into a multichannel pipette reservoir and 5 μl of this solution is deposited into the appropriate columns of 16 wells. This process is then repeated for the remaining 19 amino acids in new multichannel pipette reservoirs.
  5. In two of the remaining columns of 16 wells a control of 5 μl DMSO is pipetted into one and a control of 5 μl water is pipetted into another. The reaming two columns can be used for any other controls of interest but for these tests are left empty.
  6. The plate is then gently tapped to make sure all the solution is at the bottom of each well and they are checked to make sure none are empty.
  7. After this the appropriate amount of a 111 μM solution of the dye being tested is made from the dye stock solution and anhydrous DMSO in a falcon tube (the volume of solution to be made is around 50 μl times the number of wells to be filled).
  8. This 111 μM solution is then put into a multichannel pipette reservoir and 45 μl is added to the appropriate wells giving a total volume of 50 μl. There is also a 10-fold excess of amino acid molecules compared to dye molecules.
  9. This plate is then taken and wrapped in aluminum foil and placed on a bioshaker at 20° C. and 1500 RPM.
  10. The plate is allowed to stir for 2 hr under these conditions before being taken and measured (kinetics studies have shown that under these conditions the reaction is >95% complete at the 2 hr time point except for proline which due to steric factors reacts at a slower rate).

Results are shown in FIGS. 7-22.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of identifying amino acids in a plurality of amino acids, the method comprising:
    (a) conjugating a probe to amino acids in a plurality of amino acids, wherein the amino acids in the plurality of amino acids are different, wherein the probe comprises a dipyrromethane-$BF_2$ derivative, and wherein the dipyrromethane-$BF_2$ derivative comprises a labile or reactive group and exhibits different fluorescent spectral properties when conjugated to the amino acids in the plurality of the amino acids, wherein each amino acid in the plurality of amino acids is at the N- or C-terminal of a polypeptide;
    (b) detecting one or more fluorescent spectral properties of the probe conjugated to the different amino acids; and
    (c) identifying the amino acids in the plurality of the amino acids by comparing the fluorescent spectral properties of the conjugated probe to a plurality of reference fluorescent spectral properties, wherein each reference fluorescent spectral property is representative of the probe conjugated to a different amino acid.

2. The method of claim 1, wherein the probe is covalently conjugated to the amino acids.

3. The method of claim 1, wherein the probe is conjugate to an amino, a carboxylic, a hydroxyl or a thiol group of the amino acids.

4. The method of claim 1, wherein the plurality of the amino acids is in a sample, optionally, the sample is a biological sample, optionally the biological sample is a biological fluid, a tissue, an organ, or a cell.

5. The method of claim 1, wherein said detecting one or more fluorescent spectral properties of the conjugated probe comprises super resolution microscopy, optionally, the super resolution microscopy comprises stochastic optical reconstruction microscopy (STORM).

6. The method of claim 1, wherein detecting one or more fluorescent spectral properties comprises detecting fluorescence, fluorescence emission intensity, fluorescence polarity/anisotropy, or fluorescence lifetime of the conjugated probe.

7. The method of claim 6, wherein said detecting the fluorescence emission intensity, fluorescence polarity/anisotropy or fluorescence lifetime is at a single wavelength.

8. The method of claim 6, comprising said detecting the fluorescence emission intensity, fluorescence polarity/anisotropy or fluorescence lifetime is at a plurality of wavelengths.

9. The method of claim 1, wherein the each amino acid in the plurality of amino acids is at the N-terminal of the polypeptide.

10. The method of claim 1, wherein the dipyrromethane-$BF_2$ derivative comprises a 4,4-difluoro-4-bora-3a,4a-diaza-s-indacene derivative.

11. The method of claim 10, wherein the probe is conjugated via position 8 (meso position) of the 4,4-difluoro-4-bora-3a,4a-diaza-s-indacene derivative.

12. The method of claim 11, wherein the 4,4-difluoro-4-bora-3a,4a-diaza-s-indacene derivative comprises a labile or reactive group at position 8 (meso position).

13. The method of claim 1, wherein the probe is of Formula (I):

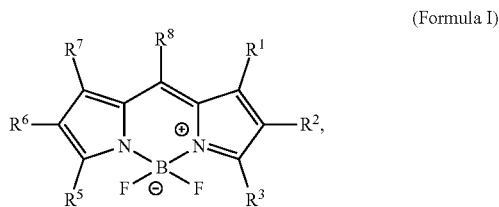

(Formula I)

wherein:
    $R^1$, $R^2$, $R^3$, $R^4$, $R^5$, $R^6$, $R^7$ and $R^8$ are each independently selected from the group consisting of hydrogen, halogen, alkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cyano, nitro, thiol, alkylthio, sulfinyl, sulfonyl, carbamoyl, isocyanato, thiocyanato, isothiocyanato, ureido, and a labile or leaving group, provided that at least one of $R^1$, $R^2$, $R^3$, $R^4$, $R^5$, $R^6$, $R^7$ and $R^8$ is a labile or leaving group, and
    any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more (e.g., 1, 2, 3, 4, 5 or 6) independently selected substituents from the group consisting of halogen, hydroxy, carboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

14. The method of claim 13, wherein $R^8$ is a labile or leaving group.

15. The method of claim 14, wherein $R^8$ is optionally substituted alkylthio, halogen, optionally substituted alkoxyl, hydroxyl, optionally substituted acyloxy, tosylate, triflate, mesylate, nitrile, azide, carbamate, disulfide, thioester, and diazonium.

16. The method of claim 15, wherein $R^8$ is —$SR^{8S}$ or halogen, wherein $R^{8S}$ is optionally substituted alkyl, optionally substituted alkenyl, optionally cycloalkyl, optionally substituted heterocyclyl, optionally substituted aryl or optionally substituted heteroaryl.

17. The method of claim 16, wherein $R^8$ is —$SR^{8S}$.

18. The method of claim 14, wherein at least one of $R^1$, $R^2$, $R^3$, $R^5$, $R^6$ and $R^7$ is an electron withdrawing group (EWG).

19. The method of claim 14, wherein at least one of $R^1$, $R^2$, $R^3$, $R^5$, $R^6$ and $R^7$ is an electron donating group (EDG).

20. The method of claim 14, wherein:
   a. at least two of $R^1$, $R^2$ and $R^3$ are same;
   b. at least two of $R^1$, $R^2$ and $R^3$ are different;
   c. $R^1$ and $R^7$ are different, or $R^2$ and $R^6$ are different, or $R^3$ and $R^5$ are different; or
   d. $R^1$ and $R^7$ are same, $R^2$ and $R^6$ are same, and $R^3$ and $R^5$ are same.

21. The method of claim 14, wherein:
   a. at least one of $R^1$, $R^2$, $R^3$, $R^5$, $R^6$ and $R^7$ is not H,
   b. $R^1$ is H or optionally substituted $C_1$-$C_6$alkyl;
   c. $R^3$ is H, halogen, optionally substituted $C_1$-$C_6$alkyl, optionally substituted $C_1$-$C_6$alkenyl, optionally substituted phenyl or optionally substituted naphthalene;
   d. $R^5$ is H, halogen, optionally substituted $C_1$-$C_6$, optionally substituted $C_1$-$C_6$alkenyl, optionally substituted phenyl or optionally substituted naphthalene;
   e. $R^6$ is H, halogen, optionally substituted $C_1$-$C_6$ alkyl, —C(O)H, or —$SO_3H$; or
   f. $R^7$ is H or optionally substituted $C_1$-$C_6$alkyl.

22. The method of claim 14, wherein $R^1$, $R^2$, $R^3$, $R^5$, $R^6$ and $R^7$ are H.

23. A method of sequencing a polypeptide, the method comprises:
   (a) conjugating a probe to a terminal amino acid of a polypeptide, wherein the probe comprises a dipyrromethane-$BF_2$ derivative, and wherein the dipyrromethane-$BF_2$ derivative comprises a labile or reactive group and exhibits different fluorescent spectral properties when conjugated to different amino acids;
   (b) detecting one or more fluorescent spectral properties of the probe conjugated to the amino acid; and
   (c) identifying the amino acid by comparing the fluorescent spectral properties of the conjugated probe to a plurality of reference fluorescent spectral properties, wherein each reference fluorescent spectral property is representative of the probe conjugated to a different amino acid;
   (d) cleaving the conjugated amino acid from the polypeptide; and
   (e) sequentially repeating steps (a) to (d) one or more times to determine the sequence of at least a portion of the polypeptide.

24. The method of claim 23, wherein the method comprises:
   in step (a) conjugating a probe to a terminal amino acid of a plurality of polypeptides, wherein the probe comprises a dipyrromethane-$BF_2$ derivative, and wherein the dipyrromethane-$BF_2$ derivative comprises a labile or reactive group and exhibits different fluorescent spectral properties when conjugated to different terminal amino acids, and the method further comprises, after step (c), steps:
   (d) cleaving the conjugated amino acid of each of the plurality of polypeptides; and
   (e) sequentially repeating steps (a) to (d) one or more times to determine the sequence of at least a portion of each of the plurality of polypeptides.

25. The method of claim 24, wherein the method comprises detecting one or more spectral properties for the probe conjugated to the terminal amino acid of each of the plurality of polypeptides at spatially resolved locations in a sample comprising the plurality of polypeptides, where the probe conjugated to the terminal amino acid of each of the plurality of polypeptides are from step (a) of claim 24.

26. The method of claim 23, wherein the dipyrromethane-$BF_2$ derivative comprises a 4,4-difluoro-4-bora-3a,4a-diaza-s-indacene derivative.

27. The method of claim 26, wherein the probe is conjugated via position 8 (meso position) of the 4,4-difluoro-4-bora-3a,4a-diaza-s-indacene derivative.

28. The method of claim 23, wherein the probe is of Formula (I):

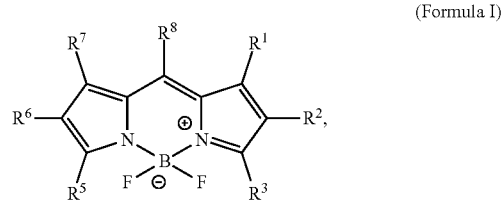

(Formula I)

wherein:
   $R^1$, $R^2$, $R^3$, $R^4$, $R^5$, $R^6$, $R^7$ and $R^8$ are each independently selected from the group consisting of hydrogen, halogen, alkyl, alkenyl, alkynyl, optionally substituted alkoxyl, aryl, heteroaryl, cycloalkyl, heterocyclyl, amino, alkylamino, dialkylamino, arylamino, heteroarylamino, hydroxyl, acyl, acyloxy, carbonyl, carboxyl, ester, alkoxyl, cyano, nitro, thiol, alkylthio, sulfinyl, sulfonyl, carbamoyl, isocyanato, thiocyanato, isothiocyanato, ureido, and a labile or leaving group, provided that at least one of $R^1$, $R^2$, $R^3$, $R^4$, $R^5$, $R^6$, $R^7$ and $R^8$ is a labile or leaving group, and any alkyl, alkenyl, alkynyl, alkoxyl, aryl, heteroaryl, cycloalkyl, heterocyclyl, alkylamino, dialkylamino, arylamino, heteroarylamino, acyl, acyloxy, ester, alkoxyl, and alkylthio, can be optionally substituted with one or more independently selected substituents from the group consisting of halogen, hydroxy, carboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carbonyl, carboxyl, hydroxyalkyl, alkanesulfonyl, arenesulfonyl, alkanesulfonamido, arenesulfonamido, aralkylsulfonamido, alkylcarbonyl, acyloxy, cyano or ureido.

* * * * *